US010426763B2

(12) United States Patent
Kahrs

(10) Patent No.: US 10,426,763 B2
(45) Date of Patent: *Oct. 1, 2019

(54) PHARMACEUTICAL COMPOSITIONS COMPRISING GLITAZONES AND NRF2 ACTIVATORS

(71) Applicant: Bjoern Colin Kahrs, Collonge-Bellerive (CH)

(72) Inventor: Bjoern Colin Kahrs, Collonge-Bellerive (CH)

(73) Assignee: Bjoern Colin Kahrs, Collonge-Bellerive (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/356,766

(22) Filed: Nov. 21, 2016

(65) Prior Publication Data

US 2017/0065571 A1 Mar. 9, 2017

Related U.S. Application Data

(63) Continuation of application No. 14/363,042, filed as application No. PCT/EP2012/074915 on Dec. 10, 2012, now Pat. No. 9,504,679, which is a continuation-in-part of application No. 13/654,632, filed on Oct. 18, 2012, now abandoned.

(60) Provisional application No. 61/663,761, filed on Jun. 25, 2012.

(30) Foreign Application Priority Data

Dec. 19, 2011 (EP) .................................... 11194292
Jun. 21, 2012 (EP) .................................... 12004652

(51) Int. Cl.
| | | |
|---|---|---|
| *A61K 31/225* | (2006.01) | |
| *A61K 31/05* | (2006.01) | |
| *A61K 31/12* | (2006.01) | |
| *A61K 31/16* | (2006.01) | |
| *A61K 31/19* | (2006.01) | |
| *A61K 31/216* | (2006.01) | |
| *A61K 31/385* | (2006.01) | |
| *A61K 31/47* | (2006.01) | |
| *A61K 31/426* | (2006.01) | |
| *A61K 31/26* | (2006.01) | |
| *A61K 9/00* | (2006.01) | |
| *A61K 31/4439* | (2006.01) | |

(52) U.S. Cl.
CPC ........ *A61K 31/4439* (2013.01); *A61K 9/0053* (2013.01); *A61K 31/05* (2013.01); *A61K 31/12* (2013.01); *A61K 31/16* (2013.01); *A61K 31/19* (2013.01); *A61K 31/216* (2013.01); *A61K 31/225* (2013.01); *A61K 31/26* (2013.01); *A61K 31/385* (2013.01); *A61K 31/426* (2013.01); *A61K 31/47* (2013.01); *Y02A 50/395* (2018.01); *Y02A 50/414* (2018.01)

(58) Field of Classification Search
CPC ...... A61K 31/225; A61K 31/05; A61K 31/12; A61K 31/16; A61K 31/19; A61K 31/216; A61K 31/385; A61K 31/47; A61K 31/426; A61K 31/26; A61K 9/00
See application file for complete search history.

(56) References Cited

U.S. PATENT DOCUMENTS

| | | |
|---|---|---|
| 4,687,777 A | 8/1987 | Meguro et al. |
| 4,959,389 A | 9/1990 | Speiser et al. |
| 5,002,953 A | 3/1991 | Hindley |
| 5,965,584 A | 10/1999 | Ikeda et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,403,121 B1 | 6/2002 | Adjei et al. |
| 6,436,992 B1 | 8/2002 | Joshi et al. |
| 6,509,376 B1 | 1/2003 | Joshi et al. |
| 6,607,751 B1 | 8/2003 | Odidi et al. |
| 6,858,750 B2 | 2/2005 | Joshi et al. |
| 7,157,423 B2 | 1/2007 | Joshi et al. |
| 7,320,999 B2 | 1/2008 | Joshi et al. |
| 7,435,755 B2 | 10/2008 | Konopleva et al. |
| 7,601,841 B2 | 10/2009 | McGee et al. |
| 7,619,001 B2 | 11/2009 | Joshi et al. |
| 7,803,840 B2 | 9/2010 | Joshi et al. |
| 7,976,853 B2 | 7/2011 | Ohkouchi et al. |
| 8,071,130 B2 | 12/2011 | Kiyoshima et al. |
| 8,129,429 B2 | 3/2012 | Sporn et al. |
| 8,399,514 B2 | 3/2013 | Lukashev et al. |
| 8,524,773 B2 | 9/2013 | Joshi et al. |
| 8,759,393 B2 | 6/2014 | Joshi et al. |

(Continued)

FOREIGN PATENT DOCUMENTS

| | | |
|---|---|---|
| AU | 2017225019 | 9/2017 |
| EP | 0 312 697 | 6/1988 |
| EP | 1 131 065 | 6/2003 |
| GB | 2373725 | 10/2002 |
| WO | WO 98/52549 | 11/1998 |
| WO | WO 99/49858 | 10/1999 |
| WO | WO 02/20517 | 3/2002 |
| WO | WO 02/055063 | 7/2002 |

(Continued)

OTHER PUBLICATIONS

Moharregh-Khiabani et al., PLOS 2010, vol. 5, Issue 7, 1-8.*

(Continued)

*Primary Examiner* — Sun Jae Yoo
(74) *Attorney, Agent, or Firm* — Saliwanchik, Lloyd & Eisenschenk

(57) ABSTRACT

The invention relates to pharmaceutical compositions comprising PPAR agonists and Nrf2 activators and methods of using combinations of PPAR agonists and Nrf2 activators for treating diseases such as psoriasis, asthma, multiple sclerosis, inflammatory bowel disease, and arthritis.

9 Claims, 7 Drawing Sheets

Specification includes a Sequence Listing.

(56) References Cited

U.S. PATENT DOCUMENTS

| | | | |
|---|---|---|---|
| 9,061,020 | B2 | 6/2015 | Weinstein |
| 9,539,249 | B2 | 1/2017 | Weinstein |
| 9,867,816 | B2 | 1/2018 | Weinstein |
| 2002/0164385 | A1 | 11/2002 | Dannenberg et al. |
| 2004/0013643 | A1 | 1/2004 | Mach |
| 2004/0219212 | A1 | 11/2004 | Castan et al. |
| 2005/0148664 | A1 | 7/2005 | Joshi et al. |
| 2006/0069161 | A1 | 3/2006 | Lee et al. |
| 2006/0205659 | A1 | 9/2006 | Joshi et al. |
| 2006/0264481 | A1 | 11/2006 | Chen |
| 2007/0027076 | A1 | 2/2007 | Joshi et al. |
| 2008/0004344 | A1 | 1/2008 | Nilsson et al. |
| 2008/0089861 | A1 | 4/2008 | Went et al. |
| 2008/0103165 | A1 | 5/2008 | Barlow et al. |
| 2008/0233185 | A1 | 9/2008 | Joshi et al. |
| 2008/0299196 | A1 | 12/2008 | Nilsson et al. |
| 2008/0300217 | A1 | 12/2008 | Nilsson |
| 2009/0060873 | A1 | 3/2009 | Sporn et al. |
| 2009/0082260 | A1 | 3/2009 | Lamb et al. |
| 2009/0304790 | A1 | 12/2009 | Nilsson et al. |
| 2010/0087481 | A1 | 4/2010 | Lee |
| 2010/0144651 | A1 | 6/2010 | Nilsson et al. |
| 2010/0184783 | A1 | 7/2010 | Raud et al. |
| 2011/0112097 | A1 | 5/2011 | Jaehne et al. |
| 2011/0281829 | A1 | 11/2011 | Chen |
| 2012/0022156 | A1 | 1/2012 | Zhang et al. |
| 2012/0196931 | A1 | 8/2012 | Lukashev et al. |
| 2013/0158077 | A1 | 6/2013 | Kahrs |
| 2013/0172391 | A1 | 7/2013 | Kahrs |
| 2014/0308244 | A1 | 10/2014 | Steinman et al. |

FOREIGN PATENT DOCUMENTS

| | | |
|---|---|---|
| WO | WO 03/087174 | 10/2003 |
| WO | WO 2004/098510 | 11/2004 |
| WO | WO 2005/023241 | 3/2005 |
| WO | WO 2005/027899 | 3/2005 |
| WO | WO 2005/033074 | 4/2005 |
| WO | WO 2005/055933 | 6/2005 |
| WO | WO 2005/086904 | 9/2005 |
| WO | WO 2006/033081 | 3/2006 |
| WO | WO 2006/037342 | 4/2006 |
| WO | WO 2006/092580 | 9/2006 |
| WO | WO 2006/122652 | 11/2006 |
| WO | WO 2007/042034 | 4/2007 |
| WO | WO 2008/096271 | 8/2008 |
| WO | WO 2008/097596 | 8/2008 |
| WO | WO 2009/089545 | 7/2009 |
| WO | WO 2010/003528 | 1/2010 |
| WO | WO 2010/022177 | 2/2010 |
| WO | WO 2010/039529 | 4/2010 |
| WO | WO 2010/093944 | 8/2010 |
| WO | WO 2011/015868 | 2/2011 |
| WO | WO 2011/039175 | 4/2011 |
| WO | WO 2011/075514 | 6/2011 |
| WO | WO 2011/098746 | 8/2011 |
| WO | WO 2011/100589 | 8/2011 |
| WO | WO 2012/040082 | 3/2012 |
| WO | WO 2012/068454 | 5/2012 |
| WO | WO 2013/148690 | 10/2013 |
| WO | WO 2014/020156 | 2/2014 |
| WO | WO 2014/120538 | 8/2014 |
| WO | WO 2018/053040 | 3/2018 |

OTHER PUBLICATIONS

Kaiser et al., Journal of Neuroimmunology 211 (2009) 124-130.*
Farrell et al., Journal of Interferon&Citokine Research (2010), 30(10), 715-726.*
Diab, A. et al. "Peroxisome Proliferator-Activated Receptor-γ Agonist 15-Deoxy- $D^{12,1412,14}$-Prostaglandin J$_2$ Ameliorates Experimental Autoimmune Encephalomyelitis" *The Journal of Immunology*, 2002, pp. 2508-2515, vol. 168.
Drew, P. et al. "PPAR-γ: Therapeutic Potential for Multiple Sclerosis" *PPAR Research*, 2008, pp. 1-9.
Feinstein, D. et al. "Peroxisome Proliferator-Activated Receptor-γ Agonists Prevent Experimental Autoimmune Encephalomyelitis" *Annals of Neurology*, Jun. 2002, pp. 694-702, vol. 51.
Floyd, Z. et al. "Modulation of peroxisome proliferator-activated receptor γ stability and transcriptional activity in adipocytes by resveratrol" *Metabolism Clinical and Experimental*, 2008, pp. S32-S38, vol. 57.
Hong, F. et al. "Specific Patterns of Electrophile Adduction Trigger Keap1 Ubiquitination and Nrf2 Activation" *The Journal of Biological Chemistry*, Sep. 9, 2005, pp. 31768-31775, vol. 280, No. 36.
Hye-Youn, C. et al. "Nrf2-regulated PPARγ Expression Is Critical to Protection against Acute Lung Injury in Mice" *American Journal of Respiratory and Critical Care Medicine*, 2010, pp. 170-182, vol. 182.
Lee, J-M. et al. "Nrf2, a multi-organ protector?" *The FASEB Journal*, Jul. 2005, pp. 1061-1066, vol. 19.
Linker, R. et al. "Fumaric acid esters exert neuroprotective effects in neuroinflammation via activation of the Nrf2 antioxidant pathway" *Brain A Journal of Neurology*, 2011, pp. 678-692, vol. 134.
Nguyen, T. et al. "The Nrf2-Antioxidant Response Element Signaling Pathway and Its Activation by Oxidative Stress" *The Journal of Biological Chemistry*, May 15, 2009, pp. 13291-13295, vol. 284, No. 20.
Schilling, S. et al. "Fumaric acid esters are effective in chronic experimental autoimmune encephalomyelitis and suppress macrophage infiltration" *Clinical and Experimental Immunology*, 2006, pp. 101-107, vol. 145.
Wang, Z. et al, "Development of a Molecular Assay for Rapid Screening of Chemopreventive Compounds Targeting Nrf2" Journal of the Association for Laboratory Automation, Aug. 2008, pp. 243-248.
Yang, Y. et al. "Regulation of Immune Responses and Autoimmune Encephalomyelitis by PPARs" *PPAR Research*, 2010, pp. 1-11.
Shih, P-H. et al. "Synergistic Effect of Cyanidin and PPAR Agonist against Nonalcoholic Steatohepatitis-Mediated Oxidative Stress-Induced Cytotoxicity through MAPK and Nrf2 Transduction Pathways" *Journal of Agricultural and Food Chemistry*, 2012, pp. 2924-2933, vol. 60.
Racke, M. et al. "Nuclear Receptors and Autoimmune Disease: The Potential of PPAR Agonists to Treat Multiple Sclerosis" *The Journal of Nutrition*, 2006, pp. 700-703.
Pershadsingh, H. "Peroxisome proliferator-activated receptor-γ: therapeutic target for diseases beyond diabetes: quo vadis?" *Expert Opinion on Investigative Drugs*, 2004, pp. 215-228, vol. 13, No. 3.
Balasubramaniam, P. et al. "Fumaric acid esters in severe psoriasis, including experience of use in combination with other systemic modalities" *British Journal of Dermatology*, 2004, pp. 741-746, vol. 150.
Diab, A. et al. "Ligands for the peroxisome proliferator-activated receptor-γ and the retinoid X receptor exert additive anti-inflammatory effects on experimental autoimmune encephalomyelitis" *Journal of Neuroimmunology*, 2004, pp. 116-126, vol. 148.
Di Paola, R. et al. "Peroxisome Proliferator-Activated Receptors and Acute Lung Injury" *PPAR Research*, 2007, pp. 1-8, vol. 2007.
Erbe, D. V. et al. "Activation of PPARγ by Sartans" *Drug Development Research*, 2006, pp. 579-581, vol. 67.
Gray, E. et al. "The PPAR-gamma agonist pioglitazone protects cortical neurons from inflammatory mediators via improvement in peroxisomal function" *Journal of Neuroinflammation*, 2012, pp. 1-24, vol. 9, No. 63.
Guenova, E. et al. "Treatment of Recurrent Aphthous Stomatitis with Fumaric Acid Esters" *Arch Dermatol*, Mar. 2011, pp. 282-284, vol. 147, No. 3.
Hidaka, T. et al. "Effects of diethyl maleate (DEM), a glutathione depletory, on prostaglandin synthesis in the isolated perfused spleen of rabbits" *Arch Toxicol*, 1990, pp. 103-108, vol. 64.
Honda, T. et al. "Tricyclic Compounds Containing Nonenolizable Cyano Enones. A Novel Class of Highly Potent Anti-Inflammatory and Cytoprotective Agents" *J. Med. Chem.*, 2011, pp. 1762-1778, vol. 54.

(56) References Cited

OTHER PUBLICATIONS

Lehmann, J. M. et al. "Peroxisome Proliferator-activated Receptors α and γ Are Activated by Indomethacin and Other Non-steroidal Anti-inflammatory Drugs" *The Journal of Biological Chemistry*, Feb. 7, 1997, pp. 3406-3410, vol. 272, No. 6.

Lehmann, G. M. et al. "Regulation of Lymphocyte Function by PPARγ: Relevance to Thyroid Eye Disease-Related Inflammation" *PPAR Research*, 2007, pp. 1-12, vol. 2008.

Li, B. et al. "Prevention of Diabetic Complications by Activation of Nrf2: Diabetic Cardiomyopathy and Nephropathy" *Experimental Diabetes Research*, 2012, pp. 1-7, vol. 2012.

Lou, H. et al. "Glutathione Depletion Down-regulates Tumor Necrosis Factor α-induced NF-κB Activity via IκB Kinase-dependent and -independent Mechanisms" *The Journal of Biological Chemistry*, Oct. 5, 2007, pp. 29470-29481, vol. 282, No. 40.

Olagnier, D. et al. "Nrf2, a PPARγ Alternative Pathway to Promote CD36 Expression on Inflammatory Macrophages: Implication for Malaria" *PLoS Pathogens*, Sep. 2011, pp. 1-14, vol. 7, Issue 9.

Ormerod, A. D. et al. "Fumaric acid esters, their place in the treatment of psoriasis" *British Journal of Dermatology*, 2004, pp. 630-632, vol. 150.

Polvani, S. et al. "PPARγ and Oxidative Stress: Con(β) Catenating NRF2 and FOXO" *PPAR Research*, 2011, pp. 1-15, vol. 2012.

Rhodes, K. et al. "BG-12 and Neuroprotection in MS" pp. 1-33, Presentation, date unknown.

Rostami-Yazdi, M. et al. "Detection of Metabolites of Fumaric Acid Esters in Human Urine: Implications for Their Mode of Action" *Journal of Investigative Dermatology*, 2009, pp. 231-234, vol. 129.

Sappington, P. L. et al. "The ethyl pyruvate analogues, diethyl oxalopropionate, 2-acetamidoacrylate, and methyl-2-acetamidoacrylate, exhibit anti-inflammatory properties in vivo and/or in vitro" *Biochemical Pharmacology*, 2005, pp. 1579-1592, vol. 70.

Shiraki, T. et al, "α,β-Unsaturated Ketone Is a Core Moiety of Natural Ligands for Covalent Binding to Peroxisome Proliferator-activated Receptor γ" *The Journal of Biological Chemistry*, Apr. 8, 2005, pp. 14145-14153, vol. 280, No. 14.

Shulman, A. I. et al. "Retinoid X Receptor Heterodimers in the Metabolic Syndrome" *The New England Journal of Medicine*, Aug. 11, 2005, pp. 604-615, vol. 353, No. 6.

Su, C. G. et al. "A novel therapy for colitis utilizing PPAR-γ ligands to inhibit the epithelial inflammatory response" *The Journal of Clinical Investigation*, Aug. 1999, pp. 383-389, vol. 104, No. 4.

Wang, X. J. et al. "Identification of retinoic acid as an inhibitor of transcription factor Nrf2 through activation of retinoic acid receptor alpha" *PNAS*, Dec. 4, 2007, pp. 19859-19594, vol. 104, No. 49.

Yang, H.-C. et al. "The PPARγ Agonist Pioglitazone Ameliorates Aging-Related Progressive Renal Injury" *J Am Soc Nephrol*, 2009, pp. 2380-2388, vol. 20.

Yano, M. et al. "Statins Activate Peroxisome Proliferator-Activated Receptor γ Through Extracellular Signal-Regulated Kinase ½ and p38 Mitogen-Activated Protein Kinase-Dependent Cyclooxygenase-2 Expression in Macrophages" *Circulation Research*, 2007, pp. 1442-1451, vol. 100.

Kappos, L. et al. "Efficacy and safety of oral fumarate in patients with relapsing-remitting multiple sclerosis: a multicentre, randomised, double-blind, placebo-controlled phase IIb study" *Lancet*, 2008, pp. 1463-1472, vol. 372.

Macmanus, D. G. et al. "BG-12 reduces evolution of new enhancing lesions to T1-hypointense lesions in patients with multiple sclerosis" *J. Neurol*, 2011, pp. 449-456, vol. 258.

Moharregh-Khiabani, D. et al. "Fumaric Acid and its Esters: An Emerging Treatment for Multiple Sclerosis" *Current Neuropharmacology*, 2009, pp. 60-64, vol. 7.

Press Release Details "Positive results from Phase 3 confirm clinical trial show efficacy and safety of oral BG-12 in multiple sclerosis" http://www.biogenidec.com/press_release_details.aspx?ID=5981 &ReqId=1686377, Apr. 24, 2012, pp. 1-4.

Behshad, R. et al. "A Retrospective Case Series Review of the Peroxisome Proliferator-Activated Receptor Ligand Rosiglitazone in the Treatment of Atopic Dermatitis" *Arch Dermatol*, 2008, pp. 84-88, vol. 144, No. 1.

Cohen, J. et al. "Oral fingolimod (FTY720) significantly reduced relapse rate compared with intramuscular interferon beta-1a in relapsing-remitting multiples sclerosis: clinical results from a 12-month phase III study (Transforms)" *Multiple Sclerosis*, 2009, p. S132, vol. 15.

Costanzo, A. et al. "Safety and efficacy study on etanercept in patients with plaque psoriasis" *British Journal of Dermatology*, 2005, pp. 187-189, vol. 152.

Digga, A. et al. "Potentiometric detection of thiols: a mechanistic evaluation of quinone-thiol interactions" *Electrochemistry Communications*, 2003, pp. 732-736, vol. 5.

Ellis, C. N. et al. "Troglitazone Improves Psoriasis and Normalizes Models of Proliferative Skin Disease" *Arch Dermatol*, 2000, pp. 609-616, vol. 136.

Ellis, C. N. et al. "Placebo Response in Two Long-Term Randomized Psoriasis Studies that were Negative for Rosiglitazone" *Am J Clin Dermatol*, 2007, pp. 93-102, vol. 8, No. 2.

Ellrichmann, G. et al. "Efficacy of Fumaric Acid Esters in the R6/2 and YAC128 Models of Huntington's Disease" *PLoS ONE*, Jan. 2011, pp. 1-11, vol. 6, Issue 1, e16172.

Hayward, M. D. et al. "An extensive phenotypic characterization of the hTNFα transgenic mice" *BMC Physiology*, 2007, pp. 1-16, vol. 7, No. 13.

Hirotsu, Y. et al. "Nrf2 degron-fused reporter system: a new tool for specific evaluation of Nrf2 inducers" *Genes to Cells*, 2011, pp. 406-415, vol. 16.

Ikeda, T. et al. "Triterpenoid CDDO-Im downregulates PML/RARα expression in acute promyelocytic leukemia cells" *Cell Death and Differentiation*, 2005, pp. 523-531, vol. 12.

Ikeda, Y. et al. "Suppression of Rat Thromboxane Synthase Gene Transcription by Peroxisome Proliferator-activated Receptor γ in Macrophages via an Interaction with NFR2" *The Journal of Biological Chemistry*, Oct. 20, 2000, pp. 33142-33150, vol. 275, No. 42.

Imhoff, B. R. et al. "Tert-butylhydroquinone induces mitochondrial oxidative stress causing Nrf2 activation" *Cell Biol Toxicol*, 2010, pp. 541-551, vol. 26.

Itoh, T. et al. "Structural basis for the activation of PPARγ by oxidized fatty acids" *Nature Structural & Molecular Biology*, Sep. 2008, pp. 924-931, vol. 15, No. 9.

Jacob, A. et al. "Mechanism of the Anti-inflammatory Effect of Curcumin: PPAR-γ Activation" *PPAR Research*, 2007, pp. 1-5, vol. 2007, Article ID 89369.

Jung, K. et al. "The Nrf2 System as a Potential Target for the Development of Indirect Antioxidants" *Molecules*, 2010, pp. 7266-7291, vol. 15.

Lewis, J. D. et al. "PPARγ Agonists as a New Class of Effective Treatment for Ulcerative Colitis" *Inflamm Bowel Dis*, Jun. 2009, pp. 959-960, vol. 15, No. 6.

Mao-Qiang, M. et al. "Peroxisome-Proliferator-Activated Receptor (PPAR)-γ Activation Stimulates Keratinocyte Differentiation" *J Invest Dermatol*, 2004, pp. 305-312, vol. 123, No. 2.

Mease, P. J. et al. "Psoriatic arthritis assessment tools in clinical trials" *Ann Rheum Dis*, 2005, pp. ii49-ii54, vol. 64 (Suppl II).

Mease, P. J. "Assessment Tools in Psoriatic Arthritis" *J. Rheumatol*, 2008, pp. 1426-1430, vol. 35, No. 7.

Mix, E. et al. "Animal models of multiple sclerosis for the development and validation of novel therapies-potential and limitations" *J Neurol*, 2008, pp. 7-14, vol. 255 (Suppl 6).

Morales, A. A. et al. "Reactive Oxygen Species Are Not Required for an Arsenic Trioxide-induced Antioxidant Response or Apoptosis" *The Journal of Biological Chemistry*, May 8, 2009, pp. 12886-12895, vol. 284, No. 19.

Nakamura, Y. et al. "Electrophiles in Foods: The Current Status of Isothiocyanates and Their Chemical Biology" *Biosci. Biotechnol. Biochem.*, 2010, pp. 242-255, vol. 74, No. 2.

(56) References Cited

OTHER PUBLICATIONS

Nakamura, Y. et al. "A glutathione S-transferase inducer from papaya: rapid screening identification and structure-activity relationship of isothiocyanates" *Cancer Letters*, 2000, pp. 193-200, vol. 157.

Nettles, K. W. "Insights into PPARγ from structures with endogenous and covalently bound ligands" *Nature Structural & Molecular Biology*, Sep. 2008, pp. 893-895, vol. 15, No. 9.

Pergola, P. E. et al. "Effect of Bardoxolone Methyl on Kidney Function in Patients with T2D and Stage 3b-4 CKD" *Am J Nephrol*, 2011, pp. 469-476, vol. 33.

Reddy, R. C. "Nrf2 and PPARγ PPARtnering Against Oxidant-induced Lung Injury" *American Journal of Respiratory and Critical Care Medicine*, 2010, pp. 134-135, vol. 182.

Rinwa, P. et al. "Involvement of PPAR-gamma in curcumin-mediated beneficial effects in experimental dementia" *Naunyn-Schmied Arch Pharmacol*, 2010, pp. 529-539, vol. 381.

Schintu, N. et al. "PPAR-gamma-mediated neuroprotection in a chronic mouse model of Parkinson's disease" *European Journal of Neuroscience*, 2009, pp. 954-963, vol. 29.

Shafiq, N. et al. "Pilot trial: Pioglitazone versus placebo in patients with plaque psoriasis (the P6)" *International Journal of Dermatology*, 2005, pp. 328-333, vol. 44.

Simpson-Haidaris, P. J. et al. "Anticancer Role of PPARγ Agonists in Hematological Malignancies Found in the Vasculature, Marrow, and Eyes" *PPAR Research*, 2010, pp. 1-36, vol. 2010, Article ID 814609.

Sporn, M. B. et al. "New Synthetic Triterpenoids: Potent Agents for Prevention and Treatment of Tissue Injury Caused by Inflammatory and Oxidative Stress" *Journal of Natural Products*, 2011, pp. 537-545, vol. 74.

Swanson, C. R. et al. "The PPAR-γ agonist pioglitazone modulates inflammation and induces neuroprotection in parkinsonian monkeys" *Journal of Neuroinflammation*, 2011, pp. 1-14, vol. 8, No. 91.

Tabe, Y. et al. "Effects of PPARγ Ligands on Leukemia" *PPAR Research*, 2012, pp. 1-8, vol. 2012, Article ID 483656.

Tufekci, K. U. et al. "The Nrf2/ARE Pathway: A Promising Target to Counteract Mitochondrial Dysfunction in Parkinson's Disease" *SAGE-Hindawi Access to Research Parkinson's Disease*, 2011, pp. 1-14, vol. 2011, Article ID 314082.

Wada, K. et al. "Protective effect of endogenous PPARγ against acute gastric mucosal lesions associated with ischemia-reperfusion" *Am J Physiol Gastrointest Liver Physiol*, 2004, pp. G452-G458, vol. 287.

Wu, R. P. et al. "Nrf2 responses and the therapeutic selectivity of electrophilic compounds in chronic lymphocytic leukemia" *PNAS*, Apr. 20, 2010, pp. 7479-7484, vol. 107, No. 16.

Wu, J. H. et al. "Identification and Characterization of Novel NrF2 Inducers Designed to Target the Intervening Region of Keap1" *Chem Biol Drug Des*, 2010, pp. 475-480, vol. 75.

Xu, J. et al. "Agonists for the Peroxisome Proliferator-Activated Receptor-α and the Retinoid X Receptor Inhibit Inflammatory Responses of Microglia" *Journal of Neuroscience Research*, 2005, pp. 403-411, vol. 81.

Zhang, D. D. "Mechanistic Studies of the NRF2-KEAP1 Signaling Pathway" *Drug Metabolism Reviews*, 2006, pp. 769-789, vol. 38.

Kobayashi, M. et al. "The Antioxidant Defense System Keap1-Nrf2 Comprises a Multiple Sensing Mechanism for Responding to a Wide Range of Chemical Compounds" *Molecular and Cellular Biology*, Jan. 2009, pp. 493-502, vol. 29, No. 2.

Kumar, V. et al. "Novel Chalcone Derivatives as Potent Nrf2 Activators in Mice and Human Lung Epithelial Cells" *Journal of Medicinal Chemistry*, 2011, pp. 4147-4159, vol. 54.

Schimrigk, S. et al. "Oral fumaric esters for the treatment of active multiple sclerosis: an open-label, baseline-controlled pilot study" *European Journal of Neurology*, 2006, pp. 604-610, vol. 13.

Michalik, L. et al. "International Union of Pharmacology. LXI. Peroxisome Proliferator-Activated Receptors" *Pharmacological Reviews*, 2006, pp. 726-741, vol. 58, No. 4.

Desvergne, B. et al. "Peroxisome Proliferator-Activated Receptors: Nuclear Control of Metabolism" *Endocrine Reviews*, 1999, pp. 649-688, vol. 20, No. 5.

Peraza, M. A. et al. "The Toxicology of Ligands for Peroxisome Proliferator-Activated Receptors (PPAR)" *Toxicological Sciences*, 2006, pp. 269-295, vol. 90, No. 2.

Gilde, A. J. et al. "Peroxisome Proliferator-Activated Receptor (PPAR) α and PPARβ/δ, but not PPARγ, Modulate the Expression of Genes Involved in Cardiac Lipid Metabolism" *Circulation Research*, Mar. 21, 2003, pp. 518-524, vol. 92.

Wakabayashi, N. et al. "Protection against electrophile and oxidant stress by induction of the phase 2 response: Fate of cysteines of the Keap1 sensor modified by inducers" *PNAS*, Feb. 17, 2004, pp. 2040-2045, vol. 101, No. 7.

Lehmann, J. M. et al. "An Antidiabetic Thiazolidinedione Is a High Affinity Ligand for Peroxisome Proliferator-activated Receptor γ (PPARγ)" *Journal of Biological Chemistry*, Jun. 2, 1995, pp. 12953-12956, vol. 270, No. 22.

Yazdi, M. et al. "Fumaric acid esters" *Clinics in Dermatology*, 2008, pp. 522-526, vol. 26.

Abraki, S. et al. "Inhibition of PPAR-γ Using GW, attenuates transcription factor Nrf-2 expression in PC12 Cells" *The Journal of the Alzheimer's Association*, Jul. 2011, pp. S608-S609, 2011, vol. 7, Issue 4, Supplement.

Adams, J. et al. "The kelch repeat superfamily of proteins: propellers of cell function" *trends in Cell Biology*, Jan. 2000, pp. 17-24, vol. 10.

Barnes, P. J. "Mediators of Chronic Obstructive Pulmonary Disease" *Pharmacological Reviews*, 2004, pp. 515-548, vol. 56, No. 4.

Bardgett, M. E. "NMDA receptor blockade and hippocampal neuronal loss impair fear conditioning and position habit reversal in C57B1/6 mice" *Brain Research Bulletin*, 2003, pp. 131-142, vol. 60.

Bhagavathula, N. et al. "7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a Benzodiazepine, Suppresses Keratinocyte Proliferation and Has Antipsoriatic Activity in the Human Skin-Severe, Combined Immunodeficient Mouse Transplant Model" *The Journal of Pharmacology and Experimental Therapeutics*, 2008 pp. 938-947, vol. 324, No. 3.

Blandini, F. et al. "Glutamate and Parkinson's Disease" *Molecular Neurobiology*, 1996, pp. 73-94, vol. 12, No. 1.

Cavarra, E. et al. "Effects of Cigarette Smoke in Mice with Different Levels of $\alpha_1$-Proteinase Inhibitor and Sensitivity to Oxidants" *Am J Respir Crit Care Med*, 2001, pp. 886-890, vol. 164.

Eugster, H. et al. "Superantigen overcomes resistance of IL-6-deficient mice towards MOG-induces EAE by a TNFR1 controlled pathway" *Eur. J. Immunol.*, 2001, pp. 2302-2312, vol. 31.

Guan, Y. et al. "Peroxisome proliferator-activated receptors (PPARs): Novel therapeutic targets in renal disease" *Kidney International*, 2001, pp. 14-30, vol. 60.

Gurney, M. E. et at. "Motor Neuron Degeneration in Mice That Express a Human Cu,Zn Superoxide Dismutase Mutation" *Science*, Jun. 17, 1994, pp. 1772-1775, vol. 264.

Hayashi, A. et al. "Transcription factor Nrf2 is required for the constitutive and inducible expression of multidrug resistance-associated protein 1 in mouse embryo fibroblasts" *Biochemical and Biophysical Research Communications*, 2003, pp. 824-829, vol. 310.

Ashe, K. H. "Learning and Memory in Transgenic Mice Modeling Alzheimer's Disease" *Learn. Mem.*, 2001, pp. 301-308, vol. 8.

Jurjus, A. R. et al. "Animal models of inflammatory bowel disease" *Journal of Pharmacological and Toxicological Methods*, 2004, pp. 81-92, vol. 50.

Karapetian, R. N. et al. "Nuclear Oncoprotein Prothymosin α Is a Partner of Keap1: Implications for Expression of Oxidative Stress-Protecting Genes" *Mol. Cell. Biol.*, Feb. 2005, pp. 1089-1099, vol. 25, No. 3.

Kobayashi, A. et al. "Oxidative Stress Sensor Keap1 Functions as an Adaptor for Cul3-Based E3 Ligase to Regulate Proteasomal Degradation of Nrf2" *Molecular and Cellular Biology*, Aug. 2004, pp. 7130-7139, vol. 24, No. 16.

(56) References Cited

OTHER PUBLICATIONS

Li, H. et al. "Experimental autoimmune myasthenia gravis induction in B cell-deficient mice" *International Immunology*, 1998, pp. 1359-1365, vol. 10, No. 9.
Loewe, R. et al. "Dimethylfumarate Inhibits TNF-Induced Nuclear Entry of NF-κB/p65 in Human Endothelial Cells" *The Journal of Immunology*, 2002, pp. 4781-4787, vol. 168.
Martin, J. B. "Molecular Basis of the Neurodegenerative Disorders" *The New England Journal of Medicine*, Jun. 24, 1999, pp. 1970-1980, vol. 340, No. 25.
Mandhane, S. N. et al. "Adenosine $A_2$ receptors modulate haloperiodol-induced catalepsy in rats" *European Journal of Pharmacology*, 1997, pp. 135-141, vol. 328.
Martorana, P. A. et al. "Roflumilast Fully Prevents Emphysema in Mice Chronically Exposed to Cigarette Smoke" *American Journal of Respiratory and Critical Care Medicine*, 2005, pp. 848-853, vol. 172.
Mrowietz, U. et al. "Treatment of severe psoriasis with fumaric acid esters: scientific background and guidelines for therapeutic use" *British Journal of Dermatology*, 1999, pp. 424-429, vol. 141.
Murakami, A. et al, "Suppression of dextran sodium sulfate-induced colitis in mice by zerumbone, a subtropical ginger sesquiterpene, and nimesulide: separately and in combination" *Biochemical Pharmacology*, 2003, pp. 1253-1261, vol. 66.
Nesto, R. W. et al. "Thiazolidinedione Use, Fluid Retention and Congestive Heart Failure: A Consensus Statement from the American Heart Association and American Diabetes Association" *Circulation*, Dec. 9, 2003, pp. 2941-2948, vol. 108.
Nguyen, T. et al. "Regulatory Mechanisms Controlling Gene Expression Mediated by the Antioxidant Response Element" *Annu. Rev. Pharmacol. Toxicol.*, 2003, pp. 233-260, vol. 43.
Rangasamy, T. et al. "Genetic ablation of Nrf2 enhances susceptibility to cigarette smoke-induced emphysema in mice" *The Journal of Clinical Investigation*, Nov. 2004, pp. 1248-1259, vol. 114, No. 9.
Rivier, M. et al. "Differential Expression of Peroxisome Proliferator-Activated Receptor Subtypes During the Differentiation of Human Keratinocytes" *J. Invest. Dermatol.*, Dec. 1998, pp. 1116-1121, vol. 111, No. 6.
Rowland, L. P. et al. "Amyotrophic Lateral Sclerosis" *The New England Journal of Medicine*, May 31, 2001, pp. 1688-1700, vol. 344, No. 22.
Schlondorff, D. "Choosing the right mouse for diabetic nephropathy" *Kidney International*, 2010, pp. 749-750, vol. 77.
So, H.S. et al. "Flunarizine induces Nrf2-mediated transcriptional activation of heme oxygenase-1 in protection of auditory cells from cisplatin" *Cell Death and Differentiation*, 2006, pp. 1763-1775, vol. 13.
Thimmulappa, R. K. et al. "Identification of Nrf2-regulated Genes Induced by the Chemopreventive Agent Sulforaphane by Oligonucleotide Microarray" *Cancer Res*, 2002, pp. 5196-5203, vol. 62.
Tracey, D. et al. "Tumor necrosis factor antagonist mechanisms of action: A comprehensive review" *Pharmacology & Therapeutics*, 2008, pp. 244-279, vol. 117.
Tsao, T. et al. "Role of Peroxisome Proliferator-Activated Receptor-γ and Its Coactivator DRIP205 in Cellular Responses to CDDO (RTA-401) in Acute Myelogenous Leukemia" *Cancer Res*, 2010, pp. 4949-4960, vol. 70, No. 12.
Van Schoor, J. et al. "Effect of inhaled fluticasone on bronchial responsiveness to neurokinin A in asthma" *Eur Respir J*, 2002, pp. 997-1002, vol. 19.
Villegas, I. et al. "A new flavonoid derivative, dosmalfate, attenuates the development of dextran sulphate sodium-induced colitis in mice" *International Immunopharmacology*, 2003, pp. 1731-1741, vol. 3.
Virley, D. J. "Developing Therapeutics for the Treatment of Multiple Sclerosis" *NeuroRx: The Journal of the American Society for Experimental Neuro Therapeutics*, Oct. 2005, pp. 638-649, vol. 2.

Wakabayashi, N. et al. "Keap1-null mutation leads to postnatal lethality due to constitutive Nrf2 activation" *Nature Genetics*, Nov. 2003, pp. 238-245. vol. 35, No. 3.
Willson, T. M. et al. "The PPARs: From Orphan Receptors to Drug Discovery" *Journal of Medicinal Chemistry*, Feb. 24, 2000, pp. 527-550, vol. 43, No. 4.
Wingerchuk, D. M. et al. "Multiple Sclerosis: Current Pathophysiological Concepts" *Laboratory Investigation*, 2001, pp. 263-281, vol. 81, No. 3.
Yalcintepe, L. et al. "Expression of interleukin-3 receptor subunits on defined subpopulations of acute myeloid leukemia blasts predicts the cytotoxicity of diphtheria toxin interleukin-3 fusion protein against malignant progenitors that engraft in immunodeficient mice" *Blood*, Nov. 15, 2006, pp. 3530-3537, vol. 108, No. 10.
Zhang, D. D. et al. "Keap1 Is a Redox-Regulated Substrate Adaptor Protein for a Cul3-Dependent Ubiquitin Ligase Complex" *Mol. Cell. Biol.*, 2004, pp. 10941-10953, vol. 24, No. 24.
Miller, D.H. et al. "Therapy—immunomodulation—Part II; Efficacy of six months' therapy with oral rosiglitazone maleate in relapsing-remitting multiple sclerosis" 21st Congress of the European Committee for the Treatment and Research in Multiple Sclerosis, 10th Annual Meeting of the Americas Committee for Treatment and Research in Multiple Sclerosis, Sep. 25, 2005, p. 1, abstract only.
Wakkee, M. et al. "Drug evaluation: BG-12, an immunomodulatory dimethylfumarate" *Current Opinion in Investigational Drugs*, 2007, pp. 955-962, vol. 8, No. 11.
Sigliti-Henrietta, P. et al. "Multiple Sclerosis presented as clinically isolated syndrome: the need for early diagnosis and treatment" *Therapeutic and Clinical Risk Management*, 2008, pp. 627-630, vol. 4, No. 3.
Pershadsingh. H. et al. "Effect of pioglitazone treatment in a patient with secondary multiple sclerosis" *Journal of Neuroinflammation*, 2004, pp. 1-4, vol. 1, No. 3.
Chou, TC. "Drug Combination Studies and Their Synergy Quantification Using the Chou-Talalay Method" *Cancer Research*, Jan. 15, 2010, pp. 440-446, vol. 70, No. 2.
Feinstein, D. et al. "Peroxisome Proliferator-Activated Receptor-γ Agonists Prevent Experimental Autoimmune Encephalomyelitis" *Annals of Neurology*, Jun. 2002, pp. 694-702, vol. 51, No. 6.
Kaiser, C. et al. "A pilot test of pioglitazone as an add-on in patients with relapsing remitting multiple sclerosis" *Journal of Neuroimmunology*, 2009, pp. 124-130, vol. 211.
Storer, P. et al. "Peroxisome proliferator-activated receptor-gamma agonists inhibit the activation of microglia and astrocytes: Implications for multiple sclerosis" *Journal of Neuroimmunology*, 2005, pp. 113-122, vol. 161.
Xu, J. et al. "Peroxisome Proliferator-Activated Receptor-γ Agonists Suppress the Production of IL-12 Family Cytokines by Activated Glia" *Journal of Immunology*, 2007, pp. 1904-1913, vol. 178.
Constantinescu, C.S. et al. "Experimental autoimmune encephalomyelitis (EAE) as a model for multiple sclerosis" *Br. J. Pharmacol.*, Oct. 2011, Vo. 164, No. 4, pp. 1079-1106.
Multiple Sclerosis Society of Canada, http://mssociety.ca/readathon/_pdf/What_is_EN.pdf, accessed Sep. 9, 2014, pp. 1-3.
Pershadsingh, H.A. et al. "Improvement in Psoriasis With Rosiglitazone in a Diabetic and a Nondiabetic Patient" *SKINmed*, 2005, vol. 4, No. 6, pp. 386-390.
Loma, I. et al. "Multiple Sclerosis: Pathogenesis and Treatment" *Current Neuropharmacology*, 2011, vol. 9, No. 3, pp. 409-416.
Deeg, M.A. et al. "Pioglitazone versus Rosiglitazone: Effects on Lipids, Lipoproteins, and Apolipoproteins in Head-to-Head Randomized Clinical Studies" *PPAR Research*, 2008, vol. 2008, Article No. 520465.
Kieseier, B.C. et al. "Combination therapy in MS—still a valid strategy" *Nature Reviews Neurology*, 2011, vol. 7, No. 12, pp. 659-660.
Weinstock-Guttman, B. et al. "Combination Therapy for Multiple Sclerosis: The Treatment Strategy of the Future?" *CNS Drugs*, 2004, vol. 18, No. 12, pp. 777-792.
Fernández, O. "Combination therapy in multiple sclerosis" *Journal of the Neurological Sciences*, 2007, vol. 259, pp. 95-103.

(56) References Cited

OTHER PUBLICATIONS

Milo, R. et al. "Combination therapy in multiple sclerosis" *Journal of Neuroimmunology*, 2011, vol. 231, pp. 23-31.
Katsnelson, A. "No Go for MS Combination Therapy: American Academy of Neurology meeting report" Multiple Sclerosis Discovery Forum, Apr. 29, 2012, obtained from: http://www.msdiscovery.org/news/new_findings/1601-no-go-ms-combination-therapy, p. 1.
Office Action dated Mar. 26, 2013 in U.S. Appl. No. 13/654,632.
Office Action dated Jul. 26, 2013 in U.S. Appl. No. 13/654,632.
Office Action dated Sep. 23, 2014 in U.S. Appl. No. 13/654,632.
Office Action dated Apr. 6, 2015 in U.S. Appl. No. 13/654,632.
Office Action dated Jun. 18, 2013 in U.S. Appl. No. 13/756,687.
Office Action dated Nov. 7, 2013 in U.S. Appl. No. 13/756,687.
Office Action dated Dec. 16, 2014 in U.S. Appl. No. 13/756,687.
Talukdar, R. et al. "Pancreatic stellate cells: New target in the treatment of chronic pancreatitis" *Journal of Gastroenterology and Hepatology*, 2008, pp. 34-41, vol. 23, No. 1.
Ferguson, H. E. et al. "Electrophilic Peroxisome Proliferator-Activated Receptor-γ Ligands Have Potent Antifibrotic Effects in Human Lung Fibroblasts" *American Journal of Respiratory Cell and Molecular Biology*, Feb. 9, 2009, pp. 722-730, vol. 41, No. 6.
Mrowietz, U. et al. "Dimethylfumarate for psoriasis: more than a dietary curiosity" *TRENDS in Molecular Medicine*, Jan. 2005, pp. 43-48, vol. 11, No. 1.
Robershaw, H. et al. "Pioglitazone: a promising therapy for psoriasis" *British Journal of Dermatology*, 2005, pp. 189-191, vol. 52, No. 1.
Baghdasaryan, A. et al. "Curcumin improves sclerosing cholangitis in Mdr2$^{-/-}$ mice by inhibition of cholangiocyte inflammatory response and portal myofibroblast proliferation" *GUT*, 2010, pp. 521-530, vol. 59, No. 4.
El-Agamy, D. S. et al. "Prevention and treatment of *Schistosoma mansoni*-induced liver fibrosis in mice" *Inflammopharmacology*, Aug. 24, 2011, pp. 307-316, vol. 19, No. 6.
Database Medline [Online] US National Library of Medicine, Database accession No. NLM19564840, Jul. 2009, p. 1.
Rau, O. et al. "Carnosic Acid and Carnosol, Phenolic Diterpene Compounds of the Labiate Herbs Rosemary and Sage, are Activators of the Human Peroxisome Proliferator-Activated Receptor Gamma" *Planta Medica*, May 16, 2006, pp. 881-887, vol. 72, No. 10.
Kim, Y. et al. "An Inducible Pathway for Degradation of FLIP Protein Sensitizes Tumor Cells to TRAIL-induced Apoptosis" *The Journal of Biological Chemistry*, Jun. 21, 2002, pp. 22320-22329, vol. 277, No. 25.
Shishodia, S. et al. "Curcumin: Getting Back to the Roots" *Annals New York Academy of Sciences*, 2005, pp. 206-217, vol. 1056.
Nielson, N. M. et al. "Glycolamide Esters as Biolabile Prodrugs of Carboxylic Acid Agents: Syntheses, Stability, Bioconversion, and Physicochemical Properties" *Journal of Pharmaceutical Sciences*, Apr. 4, 1988, pp. 285-298, vol. 77, No. 4.
Wakkee M. et al. "Drug evaluatuion: BG-12, an immunomodulatory dimethylfumarate" *Current Opinion in Investigational Drugs*, 2007, pp. 955-962, vol. 8, No. 11.
Boehncke W.H. "The Psoriasis SCID Mouse Model: A Tool for Drug Discovery?" *Ernst Schering Res Found Workshop*, 2005, pp. 213-234, vol. 50.
Freyschmidt-Paul, P. et al. "Alopecia areata in animal models—New insights into pathogenesis and treatment of a T cell-mediated autoimmune disorder" *J Dtsch Dermatol Ges*, Apr. 2004, pp. 260-273, vol. 2, No. 4.
Kim, E.H. et al. "15-Deoxy-$\Delta^{12-14}$-prostaglandin $J_2$ as a potential endogenous regulator of redox-sensitive transcription factors" *Biochemical Pharmacology*, Nov. 30, 2006, pp. 1516-1528, vol. 72, No. 11.
Wu, Q. Q. et al, "Bardoxolone methyl (BARD) ameliorates ischemic AKI and increases expression of protective genes Nrf2, PPAR γ, and HO-1" *Am. J. Physiol. Renal Physiol.*, Feb. 2, 2011, pp. F1180-F1192, vol. 300, No. 5.

Hernandez-Trujillo, Y. et al. "Rosiglitazone but not losartan prevents Nrf-2 dependent CD36 gene expression up-regulation in an in vivo atherosclerosis model" *Cardiovacular Diabetology*, Feb. 26, 2008, pp. 1-15, vol. 7, No. 3.
Shehzad, A. et al. "New mechanisms and the anti-inflammatory role of curcumin in obesity and obesity-related metabolic diseases" *European Journal of Nutrition*, Mar. 27, 2011, pp. 151-161, vol. 50, No. 3.
Jha, R. K. et al. "Acute pancreatitis: A literature review" *Medical Science Monitor*, Jul. 2009, pp. RA147-RA156, vol. 15, No. 7.
Klotz, L. et al. "Proinflammatory Stimulation and Pioglitazone Treatment Regulate Peroxisome Proliferator-Activated Receptor y Levels in Peripheral Blood Mononuclear Cells from Healthy Controls and Multiple Sclerosis Patients" *The Journal of Immunology*, 2005, pp. 4948-4955, vol. 175.
Wang, X. et al. "Double antioxidant activities of rosiglitazone against high glucose-induced oxidative stress in hepatocyte" *Toxicology in Vitro*, 2011, pp. 839-847, vol. 25.
Ishii, T. et al., "Role of Nrf2 in the regulation of CD36 and stress protein expression in murine macrophages: activation by oxidatively modified LDL and 4-hydroxynonenal," *Circulation Research*, vol. 94, No. 5, pp. 609-616, 2004.
Collins, A. R. et al., "Age-accelerated atherosclerosis correlates with failure to upregulate antioxidant genes," *Circulation Research*, vol. 104, No. 6, pp. e42-e54, 2009.
Park, E. Y. et al., "Transactivation of the PPAR-responsive enhancer module in chemopreventive glutathione S-transferase gene by the peroxisome proliferator-activated receptor-γ and retinoid X receptor heterodimer," *Cancer Research*, vol. 64, No. 10, pp. 3701-3713, 2004.
Cho, H. et al., "Gene expression profiling of NRF2-mediated protection against oxidative injury," *Free Radical Biology and Medicine*, vol. 38, No. 3, pp. 325-343, 2005.
Huang, J. et al., "Transcription factor Nrf2 regulates SHP and lipogenic gene expression in hepatic lipid metabolism," *American Journal of Physiology Gastrointest Liver Physiol*, vol. 299, No. 6, pp. G1211-G1221, 2010.
Faine, L. A. et al., "Anti-inflammatory and antioxidant properties of a new arylidene-thiazolidinedione in macrophages," *Current Medicinal Chemistry*, vol. 18, No. 22, pp. 3351-3360, 2011.
Zhan L. et al., "Regulatory role of KEAP1 and NRF2 in PPARγ expression and chemoresistance in human non-small-cell lung carcinoma cells," *Free Radic Biol Med.*, Aug. 15, 2012, vol. 53, No. 4, pp. 758-768.
Laquer, V. T. "Case Report of Improvement of Psoriasis with Pioglitazone," Clinical Vignette, Proceedings of UCLA Healthcare, vol. 14, 2010, pp. 1-3.
Gelman, L. et al., "An update on the mechanisms of action of the peroxisome proliferator-activated receptors (PPARs) and their roles in inflammation and cancer," *Cell Mol Life Sci.*, Jun. 1999, vol. 55, Nos. 6-7, pp. 932-943. Review.
Cho, H. et al., "Nrf2-regulated PPARγ Expression Is Critical to Protection against Acute Lung Injury in Mice," *Am J. Respir Crit Care Med*, 2010, vol. 182, pp. 170-182.
Pershadsingh, H.A. et al., "Treatment of psoriasis with troglitazone therapy," *Arch Dermatol.*, Oct. 1998, vol. 134, No. 10, pp. 1304-1305.
Itoh, S. et at., "Combined treatment with ursodeoxycholic acid and pioglitazone in a patient with NASH associated with type 2 diabetes and psoriasis," *Dig Dis Sci.*, Nov. 2003, vol. 48, No. 11, pp. 2182-2186.
Kuenzli, S, et al., "Effect of topical PPARbeta/delta and PPARγ agonists on plaque psoriasis. A pilot study," *Dermatology*, 2003, vol. 206, No. 3, pp. 252-256.
Brauchli, Y. B. et al., "Association between use of thiazolidinediones or other oral antidiabetics and psoriasis: A population based case-control study," *J Am Acad Dermatol.*, Mar. 2008, vol. 58, No. 3, pp. 421-429.
Bongartz, T. et al., "Treatment of active psoriatic arthritis with the PPARgamma ligand pioglitazone: an open-label pilot study," *Rheumatology* (Oxford) 2005, vol. 44, pp. 126-129.
Zhang, T. et al., "Activation of nuclear factor erythroid 2-related factor 2 and PPARγ plays a role in the genistein-mediated attenu-

(56) References Cited

OTHER PUBLICATIONS ation of oxidative stress-induced endothelial cell injury," *British Journal of Nutrition*, vol. 109, No. 2, pp. 223-235, 2013, Published online May 3, 2012.
Lebwohl, M. et al., "Combination therapy to treat moderate to severe psoriasis," *J Am Acad Dermatol.*, 2004, vol. 50, pp. 416-430.
Mittal, R. et al., "Efficacy and safety of combination acitretin and pioglitazone therapy in patients with moderate to severe chronic plaque-type psoriasis: a randomized, double-blind, placebo-controlled clinical trial," *Arch Dermatol.*, 2009, vol. 145, pp. 387-393.
European Search Report in Application No. EP 12004652, dated Jan. 15, 2013, pp. 1-7.
European Search Report in Application No. EP 11194292, dated Jan. 25, 2012, pp. 1-10.
International Search Report in International Application No. PCT/EP2012/074915, dated Apr. 18, 2013, pp. 1-5.
Natarajan, C. et al. "Peroxisome proliferator-activated receptor-gamma agonists inhibit experimental allergic encephalomyelitis by blocking IL-12 production, IL-12 signaling and Th1 differentiation" *Genes and Immunity*, 2002, pp. 59-70, vol. 3.
Executed Declaration Pursuant to 37 C.F.R. §1.132, filed in U.S. Appl. No. 13/756,687, Nov. 3, 2014, pp. 1-22.
Executed Declaration Pursuant to 37 C.F.R. §1.132, filed in U.S. Appl. No. 13/654,632, Jul. 24, 2014, pp. 1-22.
Executed Declaration Pursuant to 37 C.F.R. §1.132, filed in U.S. Appl. No. 13/654,632, Jan. 12, 2015, pp. 1-22.
Pelidou et al., *Therapeutics and Clinical Risk Management*, 2008, pp. 627-630, vol. 4, No. 3.
Tecfidera, 2015, http://mssociety.ca/en/treatments/treatment_tecifedra_faq.htm, pp. 1-3.
Pioglitazone, 2015, http://medicineworld.org/stories/lead/5-2009/piglitazone-against-multiple-sclerosis.html, pp. 1-3.
MS, 2015, http://www.tecifedera.com/?cid=ppc-bng-branded_sitelinks-na-6693-branded_sitelinks, pp. 1-3.
ALS, 2015, http://www.mayoclinic.org/diseases-condition/amyotrphic-lateral-sclerosis/basics/treatment/con-2024397, pp. 1-4.
Gold, R. et al. "Fumaric acid and its esters: An emerging treatment for multiple sclerosis with antioxidative mechanism of action" *Clinical Immunology*, 2012, pp. 44-48, vol. 142.
Gold, R. et al. "Clinical efficacy of BG-12, an oral therapy, in relapsing-remitting multiple sclerosis: data from the phase 3 DEFINE trial" *Multiple Sclerosis Journal*, 2011, p. 1, vol. 17.
Costello, F. et al. "Combination therapies for multiple sclerosis: scientific rationale, clinical trials, and clinical practice" *Current Opinion in Neurology*, Jun. 2007, pp. 281-285, vol. 20, No. 3.
Anonymous "BG 12: BG 00012, BG 12/Oral Fumarate, FAG-201, second-generation fumarate derivative—Fumapharm/Biogen Idec." *Drugs RD*, 2005, p. 1, vol. 6, No. 4.
Fox, R. J. "A Novel Oral Therapy in Development for the Treatment of Multiple Sclerosis" *European Neurological Review*, 2008, pp. 99-103, vol. 3, No. 1.
Giacomini, P. S. et al. "Emerging multiple sclerosis disease-modifying therapies" *Current Opinion in Neurology*, Jun. 2009, pp. 226-232, vol. 22, No. 3.
Gold, R. "Combination therapies in multiple sclerosis" *Journal of Neurology*, 2008, pp. 51-60, vol. 255, Suppl. 1.
Sczesny-Kaiser, M. et al. "Synergismus von Interferon β-1b und Fumarsäure? (Synergism on Interferon β-1b and Fumaric Acid)" *Aktuelle Neurologie*, 2009, pp. S284- S286, vol. 36, Suppl. 3.
Woodworth, J. et al. "Oral BG-12 in combination with interferon beta-1a or glatiramer acetate: pharmacokinetics, safety and tolerability" *26th Congress of the European Committee for Treatment and Research in Multiple Sclerosis (ECTRIMS) and 15th Annual Conference of Rehabilitation in MS (RIMS)*, Oct. 14, 2010, p. 1.
Chapple, I. L. C. "Reactive oxygen species and antioxidants in inflammatory diseases" *Journal of Clinical Periodontology*, 1997, vol. 24, pp. 287-296.

Kimura, S. et al. "Induction of Experimental Periodontitis in Mice With *Porphyromonas gingivalis*-Adhered Ligatures" *Journal of Periodontology*, Jul. 2000, vol. 71, No. 7, pp. 1167-1173.
Lehmann, M. et al., "Fumaric acid esters are potent immunosuppressants: inhibition of acute and chronic rejection in rat kidney transplantation models by methyl hydrogen fumarate" *Archives of Dermatological Research*, 2002, vol. 294, pp. 399-404.
Magesh, S. "Small Molecule Modulators or Keap1-Nrf2-ARE Pathway as Potential Preventive and Therapeutic Agents" *Medicinal Research Reviews*, 2012, vol. 32, No. 4, pp. 687-726.
Miller, S. D. et al. "Experimental Autoimmune Encephalomyelitis in the Mouse" *Current Protocols in Immunology*, 2007, Supplement 78, pp. 15.1.1-15.1.18.
Oz, H. S. et al. "Animal Models for Periodontal Disease" *Journal of Biomedicine and Biotechnology*, 2011, Article ID No. 754857, pp. 1-8.
Vollrath, V. et al. "Role of Nrf2 in the regulation of the Mrp2 (ABCC2) gene" *Biochemical Journal*, 2006, vol. 395, pp. 599-609.
Conway, D. et al. "Combination therapy in multiple sclerosis", *The Lancet*, 2010, pp. 299-308, vol. 9, No. 3, abstract only, pp. 1-2.
AD, 2015, http://ww.alz.org/alzheimers_disease_standard_prescriptions.asp, pp. 1-4.
Huntingtons, 2015, http://www.mayoclinic.org.diseases-conditions/huntingtons-disease/basics/treatment-20030685, pp. 1-4.
Parkinsons, 2015, http://www.webmd.com/parkinsons-disease/tc/parkinsons-disease-medications, pp. 1-3.
Kintscher, U. et al. "INT-131, a PPARγ agonist for the treatment of type 2 diabetes" *Current Opinion in Investigational Drugs*, 2009, pp. 381-387, vol. 10, No. 4.
Brown, K. et al. "A Novel N-Aryl Tyrosine Activator of Peroxisome Proliferator-Activated Receptor-γ Reverses the Diabetic Phenotype of the Zucker Diabetic Fatty Rat" *Diabetes*, Jul. 1999, pp. 1415-1424, vol. 48.
Carmona, M. C. et al. "S 26948: a New Specific Peroxisome Proliferator-Activated Receptor γ Modulator With Potent Antidiabetes and Antiatherogenic Effects" *Diabetes*, Nov. 2007, pp. 2797-2808, vol. 56.
Minoura, H., et al. "Ameliorating effect of FK614, a novel nonthiazolidinedione peroxisome proliferator-activated receptor gamma agonist, on insulin resistance in Zucker fatty rat" *Eur J Pharmacol.*, Sep. 5, 2005, pp. 182-190, vol. 519, Nos. 1-2. Abstract Only.
"Applications of Transition Metal Catalysis in Drug Discovery and Development: An Industrial Perspective" First Edition. Edited by Matthew L. Crawley and Barry M. Trost, Published 2012 by John Wiley & Sons, Inc., p. 129.
Chandalia, A. et al. "MBX-102/JNJ39659100, a Novel Non-TZD Selective Partial PPAR-γ Agonist Lowers Triglyceride Independently of PPAR-α Activation" PPAR Research, 2009, pp. 1-12.
Alroughani, R. et al. "Predictors of Conversion to Multiple Sclerosis in Patients with Clinical Isolated Syndrome Using the 2010 Revised McDonald Criteria" *ISRN Neurology*, 2012, pp. 1-6.
Gold, R. et al. "Evolving expectations around early management of multiple sclerosis" *Therapeutic Advances in Neurological Disorders*, 2010, pp. 351-367, vol. 3, No. 6.
Marcus, J. F. et al. "Updates on Clinically Isolated Syndrome and Diagnostic Criteria for Multiple Sclerosis" *The Neurohospitalist*, 2012, pp. 65-80, vol. 3, No. 2.
Nicholas, R. et al. "Development of oral immunomodulatory agents in the management of multiple sclerosis" Drug Design, Development and Therapy, 2011, pp. 255-274, vol. 1, No. 5.
Mahmoud, A. M., et al. "Oxidative Stress in Metabolic Disorders and Drug-Induced Injury: The Potential Role of Nrf2 and PPARs Activators" *Oxidative Medicine and Cellular Longevity*, 2017, pp. 1-4.
Chorley, B. N., et al. "Identification of novel NRF2-regulated genes by ChIP-Seq: influence on retinoid X receptor alpha" *Nucleic Acids Research*, May 11, 2012, pp. 7416-7429, vol. 40, No. 15.
Zhao, X. et al. "Pleiotropic role of PPARγ in Intracerebral Hemorrhage: An Intricate System involving Nrf2, RXR and NF-κB" *CNS Neurosci Ther.*, Apr. 2015, pp. 1-20, vol. 21, No. 4.
Cai, W. et al. "Peroxisome proliferator-activated receptor γ (PPARγ): A master gatekeeper in CNS injury and repair" *Progress in Neurobiology*, Oct. 12, 2017, pp. 1-32.

(56) References Cited

OTHER PUBLICATIONS

NDA 204063, Tecfidera FDA Approved Labeling Text, Mar. 27, 2013, pp. 1-15.
Lee, D.-H. et al. "Mechanisms of Oxidative Damage in Multiple Sclerosis and Neurodegenerative Diseases: Therapeutic Modulation via Fumaric Acid Esters" *International Journal of Molecular Sciences*, 2012, pp. 11783-11803, vol. 13.
Lee, C. "Collaborative Power of Nrf2 and PPARγ Activators against Metabolic and Drug-Induced Oxidative Injury" *Oxidative Medicine and Cellular Longevity*, Aug. 27, 2017, vol. 2017, Article ID 1378175, pp. 1-14.
De Nuccio, C., "Specificities, similarities and synergies of Dimethyl Fumarate- and Pioglitazone-induced effects on mitochondria, ROS protection and differentiation in oligodendrocyte progenitors", downloaded from site: http://www.morethanneurons.com/repository_doc/Denuccio.pdf and relating to the conference: "More Than Neurons: toward a less neurocentric view of brain disorders" Dec. 1-3, 2016, pp. 1-24, Torino Incontra, Via Nino Costa, 8-10123 Torino. "More Than Neurons: toward a less neurocentric view of brain disorders" Dec. 1-3, 2016, pp. 1-2, Torino Incontra, Via Nino Costa, 8-10123 Torino (Program downloaded from site: http://www.morethanneurons.com/docs/MoreThanNeurons_Programme.pdf Conference).
Banday, A. A. et al. "Abstract 364: Nrf2-PPAR gamma Signaling Suppresses Exaggerated Renal Tubular AT1R Gene Expression and Function and Mitigates Hypertension During Oxidative Stress", *Hypertension*, Poster Session II, 2012, pp. 1-5, vol. 60.
Papp, D. et al. "The NRF2-related interactome and regulome contain multifunctional proteins and fine-tuned autoregulatory loops" *FEBS Letters*, 2012, pp. 1795-1802, vol. 586.
Alisky, J. M. "Thiazolidinediones could be an effective treatment for HIV-associated progressive multifocal leukoencephalopathy" *International Journal of Infectious Diseases*, Jul. 2007, pp. 372-373, vol. 11, No. 4.
"Clinical Study to Compare the Efficacy and Safety of Ponesimod to Placebo in Subjects With Active Relapsing Multiple Sclerosis Who Are Treated With Dimethyl Fumarate (Tecfidera®) (POINT)" ClinicalTrials.gov Identifier: NCT02907177, first posted Sep. 20, 2016, pp. 1-6.
Eriksson, I. et al. "Persistence with dimethyl fumarate in relapsing-remitting multiple sclerosis: a population-based cohort study" *European Journal of Clinical Pharmacology*, Feb. 2018, pp. 219-226, vol. 74, No. 2.
Forman, B. M. et al. "15-Deoxy-$\Delta^{12,14}$-Prostaglandin $J_2$ Is a Ligand for the Adipocyte Determination Factor PPARγ" Cell, Dec. 1, 1995, pp. 803-812, vol. 83, No. 5.
Haskew-Layton, R. E. et al. "15-Deoxy-$\Delta$12,14-prostaglandin J2 (15d-PGJ2) protects neurons from oxidative death via an Nrf2 astrocyte-specific mechanism independent of PPARγ" *Journal of Neurochemistry*, 2013, pp. 536-547, vol. 124, No. 4.
Henique, C. et al. "Nuclear Factor Erythroid 2-Related Factor 2 Drives Podocyte-Specific Expression of Peroxisome Proliferator-Activated Receptor γ Essential for Resistance to Crescentic GN" *Journal of the American Society of Nephrology*, 2015, pp. 1-17, vol. 27, No. 1.
Itoh, K. et al. "Transcription Factor Nrf2 Regulates Inflammation by Mediating the Effect of 15-Deoxy-$\Delta^{12,14}$-Prostaglandin $J_2$" *Molecular and Cellular Biology*, Jan. 2004, pp. 36-45, vol. 24, No. 1.
Kansanen, E. et al. "Regulation of Nrf2-dependent gene expression by 15-deoxy-$\Delta^{12,14}$-prostaglandin $J_2$" *Free Radical Biology & Medicine*, Nov. 1, 2009, pp. 1310-1317, vol. 47, No. 9.
Kondo, M. et al. "15-Deoxy-$\Delta^{12,14}$-prostaglandin $J_2$: The endogenous electrophile that induces neuronal apoptosis" *PNAS*, May 28, 2002, pp. 7367-7372, vol. 99, No. 11.
Lang, L. "Pioglitazone Trial for NASH: Results Show Promise" *Gastroenterology and Hepatology News*, Mar. 2007, pp. 836-838, vol. 132, No. 3.
Litjens, N. H. R. et al. "In vitro pharmacokinetics of anti-psoriatic fumaric acid esters" *BMC Pharmacology*, Oct. 12, 2004, pp. 1-7, vol. 4, No. 22.
Litjens, N. H. R. et al. "Pharmacokinetics of oral fumarates in healthy subjects" *British Journal of Clinical Pharmacology*, Oct. 2004, pp. 429-432, vol. 58, No. 4.
Luo, Z. et al. "Activation of NRF2 Coordinates DDAH/PPAR-γ/eNOS Pathways that Enhance Nitric Oxide Generation in Human Glomerular Endothelial Cells" *Hypertension*, Apr. 2015, pp. 1-17, vol. 65, No. 4.
Mayer, L. et al. "Management Strategies to Facilitate Optimal Outcomes for Patients Treated with Delayed-release Dimethyl Fumarate" *Drug Safety*, Apr. 2018, pp. 347-356, vol. 41, No. 4.
Namani, A. et al. "Modulation of NRF2 signaling pathway by nuclear receptors: Implications for cancer" *Biochimica et Biophysica Acta*, Sep. 2014, pp. 1875-1885, vol. 1843, No. 9.
Pi, J. et al. "Deficiency in the Nuclear Factor E2-related Factor-2 Transcription Factor Results in Impaired Adipogenesis and Protects against Diet-induced Obesity" *The Journal of Biological Chemistry*, Mar. 19, 2010, pp. 9292-9300, vol. 285, No. 12.
Reick, C. et al. "Neuroprotective dimethyl fumarate synergizes with immunomodulatory interferon beta to provide enhanced axon protection in autoimmune neuroinflammation" *Experimental Neurology*, 2014, pp. 50-56, vol. 257.
Scannevin, R. H. et al. "Fumarates Promote Cytoprotection of Central Nervous System Cells against Oxidative Stress via the Nuclear Factor (Erythroid-Derived 2)-Like 2 Pathway" *The Journal of Pharmacology and Experimental Therapeutics*, Apr. 2012, pp. 274-284, vol. 341, No. 1.
Schmidt, S. et al. "Anti-inflammatory and antiproliferative actions of PPAR-γ agonists on T lymphocytes derived from MS patients" *Journal of Leukocyte Biology*, Mar. 2004, pp. 478-485, vol. 75, No. 3.
Schulze-Topphoff, U. et al. "Dimethyl fumarate treatment induces adaptive and innate immune modulation independent of Nrf2" *PNAS*, Apr. 26, 2016, pp. 4777-4782, vol. 113, No. 17.
Shakya, A. et al. "Gastro-protective and Anti-stress Efficacies of Monomethyl Fumarate and a *Fumaria indica* Extract in Chronically Stressed Rats" *Cellular Molecular Neurobiology*, May 2016, pp. 621-635, vol. 36, No. 4.
Van Horssen, J. et al. "Radical changes in multiple sclerosis pathogenesis" *Biochimica et Biophysica Acta*, Feb. 2011, pp. 141-150, vol. 1812, No. 2.
Wang, G. et al. "Haematoma scavenging in intracerebral haemorrhage: from mechanisms to the clinic" *Journal of Cellular Molecular Medicine*, Feb. 2018, pp. 768-777, vol. 22, No. 2.
Yamaguchi, Y. et al. "Dimethyl fumarate inhibits osteoclasts via attenuation of reactive oxygen species signalling by augmented antioxidation" *Journal of Cellular Molecular Medicine*, Feb. 2018, pp. 1138-1147, vol. 22, No. 2.
Zhang, F. et al. "Selective Modulators of PPAR-γ Activity: Molecular Aspects Related to Obesity and Side-Effects" *PPAR Research*, 2007, pp. 1-7, vol. 2007.
Chiarelli, F. et al. "Peroxisome proliferator-activated receptor-γ agonists and diabetes: Current evidence and future perspectives" *Vascular Health and Risk Management*, 2008, pp. 297-304, vol. 4, No. 2.
Chen, J. et al. "The roles of PPAR-gamma/PGC-1alpha to Nrf2/gamma-GCS-h in lung of guinea pigs with bronchial asthma" May 27, 2011, Article in Chinese, Abstract Only.
Collins, A. R. et al. "Age-Accelerated Atherosclerosis Correlates With Failure to Upregulate Antioxidant Genes" *Circulation Research*, Mar. 27, 2009, pp. e42-e54, vol. 104, No. 6.
Eba, S. et al. "The Nuclear Factor Erythroid 2-Related Factor 2 Activator Oltipraz Attenuates Chronic Hypoxia-Induced Cardiopulmonary Alterations in Mice" *American Journal of Respiratory Cell and Molecular Biology*, 2013, pp. 324-333, vol. 49.
Ferret-Sena, V. et al. "Metabolic Dysfunction and Peroxisome Proliferator-Activated Receptors (PPAR) in Multiple Sclerosis" *International Journal of Molecular Sciences*, Jun. 1, 2018, pp. 1-25, vol. 19.
Galli, A. et al. "Hepatic Stellate Cells as a Target for TZD: Can We Treat Liver Fibrosis and Type II Diabetes at the Same Time?" *Hepatology*, 2002, pp. 1011-1013, vol. 36, No. 4.
Krönke, G. et al. "Expression of Heme Oxygenase-1 in Human Vascular Cells Is Regulated by Peroxisome Proliferator-Activated

(56) References Cited

OTHER PUBLICATIONS

Receptors" *Arteriosclerosis, Thrombosis, and Vascular Biology*, Jun. 2007, pp. 1276-1282, vol. 27, Materials and Methods, pp. 1-3, Supplemental Figure, pp. 1-2.

Kvandová, M. et al. "The Role of PPARγ in Cardiovascular Diseases" *Physiological Research*, 2016, pp. S343-S363, vol. 65.

Mrowietz, U. et al. "The Pharmacokinetics of Fumaric Acid Esters Reveal Their In Vivo Effects" *Trends in Pharmacological Sciences*, Jan. 2018, pp. 1-12, vol. 39, No. 1.

Strassburger-Krogias, K. et al. "Fumarate treatment in progressive forms of multiple sclerosis: first results of a single-center observational study" *Therapeutic Advances in Neurological Disorders*, 2014, pp. 232-238, vol. 7, No. 5.

Xenoport, Inc. "XP23829—Fumaric Ester Program Non-Confidential Package" Apr. 2012, Copyright 2010, pp. 1-31.

Xu, J. et al. "Enhanced Nrf2 Activity Worsens Insulin Resistance, Impairs Lipid Accumulation in Adipose Tissue, and Increases Hepatic Steatosis in Leptin-Deficient Mice" *Diabetes*, Dec. 2012, pp. 3208-3218, vol. 61.

Correale, J. et al., "Mitoxantrone as rescue therapy in worsening relapsing-remitting MS patients receiving IFN-β" *Journal of Neuroimmunology*,2005, pp. 173-183, vol. 162, vol. 1-2.

Haghikia, A. et al., Positive Effect on Multiple Sclerosis With Treatment of Metabolic Syndrome *Jama Neurology*,May 2016, pp. 499-501, vol. 73, No. 5.

Hucke, S. et al., "Licensing of myeloid cells promotes central nervous system autoimmunity and is controlled by peroxisome proliferator-activated receptor γ" *Brain*, 2012, pp. 1586-1605, vol. 135 (Pt 5).

Negrotto, L. et al., Immunologic Effects of Metformin and Pioglitazone Treatment on Metabolic Syndrome and Multiple Sclerosis, *JAMA Neurol.*, May 2016, pp. 520-528, vol. 73, No. 5.

Shukla, D. et al., Effects of pioglitazone on diffusion tensor imaging indices in multiple sclerosis patients, *Neuroscience Letters*,2010, pp. 153-156, vol. 472, No. 3.

Response dated Mar. 4, 2015, U.S. Appl. No. 14/162,723, pp. 1-6.

Clarke, H.J. et al. "Cross-Species Differential Plasma Protein Binding of MBX-102/JNJ39659100: A Novel PPAR-γ Agonist" *PPAR Research*, 2008 vol. 2008, Article ID 465715, pp. 1-10.

Festuccia, W.T. et al. "Peroxisome Proliferator-Activated Receptor-γ-Mediated Positive Energy Balance in the Rat Is Associated with Reduced Sympathetic Drive to Adipose Tissues and Thyroid Status" *Endocrinology*, May 2008, vol. 149, No. 5, pp. 2121-2130. Epub Jan. 24, 2008.

Grommes, C. et al. "The PPARγ agonist pioglitazone crosses the blood-brain barrier and reduces tumor growth in a human xenograft model" *Cancer Chemother Pharmacol.*, Apr. 2013, vol. 71, No. 4, pp. 929-936. Epub Jan. 29, 2013.

Maeshiba, Y. et al. "Disposition of the New Antidiabetic Agent Pioglitazone in Rats, Dogs, and Monkeys" Arzneimittelforschung/ Drug Res., Jan. 1997, vol. 47, No. 1, pp. 29-35.

Strum, J.C. et al. "Rosiglitazone Induces Mitochondrial Biogenesis in Mouse Brain" *Journal of Alzheimers Disease*, Mar. 2007, vol. 11, No. 1, pp. 45-51.

Pagel-Langenickel, I. et al. "PGC-1αIntegrates Insulin Signaling, Mitochondrial Regulation, and Bioenergetic Function in Skeletal Muscle" *he Journal of Biological Chemistry*, Aug. 15, 2008, vol. 283, No. 33, pp. 22464-22472. Epub Jun. 25, 2008.

Wu, Z. et al. "Mechanisms Controlling Mitochondrial Biogenesis and Respiration Through the Thermogenic Coactivator PGC-1" *Cell*, Jul. 9, 1999, vol. 98, No. 1, pp. 115-124.

Higgins, L.S. et al. "The Development of INT131 as a Selective PPARγ Modulator: Approach to a Safer Insulin Sensitizer" *PPAR Research*, 2008, vol. 2008, Article ID 936906, pp. 1-9.

Wakabayashi, N. et al. "When NRF2 Talks, Who's Listening?" *Antioxidants & Redox Signaling*, Dec. 1, 2010, vol. 13, No. 11, pp. 1649-1663. Epub Jul. 9, 2010.

Lee, D.H. et al. "Selective PPARγmodulator INT131 normalizes insulin signaling defects and improves bone mass in diet-induced obese mice" *Am J Physiol Endocrinol Metab.*, Mar. 1, 2012, vol. 302, No. 5, pp. E552-E560. Epub Jan. 3, 2012.

Kummer, M.P. et al. "PPARs in Alzheimer's Disease" *PPAR Research*, 2008, vol. 2008, Article ID 403896, pp. 1-8.

Ballabh, P. et al. "The blood-brain barrier: an overview: Structure, regulation, and clinical implications" *Neurobiology Disease*, Jun. 2004, vol. 16, No. 1, pp. 1-13.

Minagar, A. et al. "Blood-brain barrier disruption in multiple sclerosis" *Multiple Sclerosis*, Dec. 2003, vol. 9, No. 6, pp. 540-549.

Correale, J. et al. "The blood-brain-barrier in multiple sclerosis: Functional roles and therapeutic targeting" *Autoimmunity*, Mar. 2007, vol. 40, No. 2, pp. 148-160.

Motani, A. et al. "INT131: A Selective Modulator of PPARγ" *J. Mol. Biol.*, Mar. 13, 2009, vol. 386, No. 5, pp. 1301-1311.

Bates, D. J. P. et al. "Nitroalkene fatty acids mediate activation of Nrf2/ARE-dependent and PPARγ-dependent transcription by distinct signaling pathways and with significantly different potencies" *Biochemistry*, Sep. 13, 2011, vol. 50, No. 36, pp. 7765-7773 (pp. 1-22). Epub Aug. 17, 2011.

Carvalho, F. "Role of Nrf2 in the Regulation of Ppar Expression in Mice" *Master's Theses* 1124, Aug. 11, 2017, pp. 1-100.

Berge, S. M. et al. "Pharmaceutical Salts" *Journal of Pharmaceutical Sciences*, Jan. 1977, pp. 1-19, vol. 66, No. 1.

Tourdias, T. et al. "Neuroinflammatory Imaging Biomarkers: Relevance to Multiple Sclerosis and its Therapy" *Neurotherapeutics*, 2013, pp. 111-123, vol. 10.

Bastianello, S. et al. "Serial study of gadolinium-DTPA MRI enhancement in multiple sclerosis" *Neurology*, Apr. 1990, pp. 591-595, vol. 40, No. 4.

Smith, M. E. et al. "Clinical Worsening in Multiple Sclerosis Is Associated with Increased Frequency and Area of Gadopentetate Dimeglumine-enhancing Magnetic Resonance Imaging Lesions. "*Ann Neurol.*, May 1993, pp. 480-489, vol. 33, No. 5.

Feghali, C. A. et al. "Cytokines in Acute and Chronic Inflammation" *Frontiers in Bioscience*, Jan. 1, 1997, pp. 12-26, vol. 2.

Libbey, J. E. et al. "Experimental Autoimmune Encephalomyelitis as a Testing Paradigm for Adjuvants and Vaccines" *Vaccine*, Apr. 12, 2011, pp. 1-13, vol. 29, No. 17.

International Search Report and Written Opinion in International Application No. PCT/US14/12656, May 13, 2014, pp. 1-5.

Response filed in European Patent Application No. 14746632.0, Nov. 27, 2018, pp. 1-11.

Response dated Jul. 15, 2016, U.S. Appl. No. 14/707,122, pp. 1-19.

International Search Report and Written Opinion in International Application No. PCT/US17/51414, Nov. 3, 2017, pp. 1-11.

Mix, E. et al. "Animal models of multiple sclerosis—Potentials and limitations" *Progress in Neurobiology*, 2010, pp. 386-404, vol. 92.

Natrajan, M. S. et al. "Pioglitazone regulates myelin phagocytosis and multiple sclerosis monocytes" *Annals of Clinical and Translational Neurology*, 2015, pp. 1071-1084, vol. 2, No. 12.

Schopfer, F. J. et al. "Covalent Peroxisome Proliferator-Activated Receptor γ Binding by Nitro-Fatty Acids: Endogenous Ligands Act As Selective Modulators" *The Journal of Biological Chemistry*, 2010, pp. 1-26.

Shang, J. et al. "Cooperative cobinding of synthetic and natural ligands to the nuclear receptor PPARγ" *eLife*, Dec. 21, 2018, pp. 1-34, vol. 7, e43320.

Schopfer, F. J. et al. "Covalent Peroxisome Proliferator-activated Receptor γ Adduction by Nitro-fatty Acids: selective ligand activity and anti-diabetic signaling actions" *The Journal of Biological Chemistry*, Apr. 16, 2010, pp. 12321-12333, vol. 285, No. 16.

Blewett, M. M. et al. "Chemical proteomic map of dimethyl fumarate-sensitive cysteines in primary human T cells" *Sci Signal.*, Oct. 18, 2016, pp. 1-25 vol. 9, No. 445.

Natrajan, M. et al. "Pioglitazone treatment enhances myelin debris phagocytosis and immunoregulatory functions of monocytes from MS patients (P1.162)" *Annals of Clinical and Translational Neurology*, Apr. 2015, pp. 1-6, vol. 84 (14 Supplement).

"Targeting Residual Activity by Precision, Biomarker-Guided Combination Therapies of Multiple Sclerosis (TRAP-MS)" ClinicalTrials. gov, Identifier: NCT03109288, 2017, pp. 1-8.

\* cited by examiner

```
SEQUENCE LISTING

<160> NUMBER OF SEQ ID NOS: 1

<210> SEQ ID NO 1
<211> LENGTH: 21
<212> TYPE: PRT
<213> ORGANISM: Mus musculus
<220> FEATURE:
<221> NAME/KEY: MISC_FEATURE
<222> LOCATION: (1)..(21)
<223> OTHER INFORMATION: myelin oligodendrocyte glycoprotein peptide
      35-55, MOG35-55

<400> SEQUENCE: 1

Met Glu Val Gly Trp Tyr Arg Ser Pro Phe Ser Arg Val Val His Leu
1               5                   10                  15

Tyr Arg Asn Gly Lys
            20
```

PHARMACEUTICAL COMPOSITIONS COMPRISING GLITAZONES AND NRF2 ACTIVATORS

CROSS-REFERENCE TO RELATED APPLICATIONS

This application is a continuation of U.S. application Ser. No. 14/363,042, filed Jun. 5, 2014, which is the U.S. national stage application of International Patent Application No. PCT/EP2012/074915, filed Dec. 10, 2012, which claims the benefit of U.S. Provisional Patent Application No. 61/663,761, filed Jun. 25, 2012.

PCT/EP2012/074915 is a continuation-in-part of U.S. patent application Ser. No. 13/654,632, filed Oct. 18, 2012, now abandoned, which claims the benefit of U.S. Provisional Patent Application No. 61/663,761, filed Jun. 25, 2012.

Disclosed herein are pharmaceutical compositions comprising PPAR agonists and Nrf2 activators (each an "agent" and together "agents"), and methods of using combinations of PPAR agonists and Nrf2 activators for treating diseases such as psoriasis, asthma, multiple sclerosis, inflammatory bowel disease, and arthritis.

Peroxisome Proliferator Activated Receptors (PPARs) activate transcription by binding to elements of DNA sequences, known as peroxisome proliferator response elements (PPRE), in the form of heterodimers with retinoid X receptors (known as RXRs). Three subtypes of human PPARs have been identified and described: PPARα, PPARγ (PPAR gamma) and PPARδ (or NUC1). PPARα is mainly expressed in the liver, while PPAR is ubiquitous. PPARγ is the most extensively studied of the three subtypes See, e.g., "Differential Expression of Peroxisome Proliferator-Activated Receptor Subtypes During the Differentiation of Human Keratinocytes", Michel Rivier et al., J. Invest. Dermatol., 111, 1998, pp. 1116-1121, in which is listed a large number of bibliographic references relating to receptors of PPAR type. Mention may also be made of "The PPARs: From Orphan Receptors to Drug Discovery", Timothy M. Willson, Peter J. Brown, Daniel D. Sternbach and Brad R. Henke, J. Med. Chem., 2000, Vol. 43, pp. 527-550. It is suggested that PPARγ plays a critical role in regulating the differentiation of adipocytes, where it is greatly expressed. It also has a key role in systemic lipid homeostasis.

It has been reported that the thiazolidinedione class of compounds (the group of so-called glitazones), including rosiglitazone, rosiglitazone maleate, pioglitazone, pioglitazone hydrochloride, troglitazone and ciglitazone and/or their salt forms, are potent and selective activators of PPAR gamma (so-called PPAR gamma agonists) and bind directly to the PPAR gamma receptor (J. M. Lehmann et al., J. Biol. Chem. 12953-12956, 270 (1995)), providing evidence that PPAR gamma is a possible target for the therapeutic actions of the thiazolidinediones. Since this observation, activation of this nuclear hormone receptor has been shown to have pleiotropic metabolic and nonhypoglycemic effects. Clinical use of the agents in the treatment of Type 2 diabetes mellitus (or non insulin dependent diabetes mellitus (NIDDM)) is associated with sensitization to the glucose lowering effects of insulin as well as potentiation of other biological actions of insulin in target tissues. When used as monotherapy, there are reports of fluid retention resulting in volume expansion and, in some patients, clinical edema. The incidence of edema appears to be increased when both these agents are used in combination with insulin (Nesto R. W. et al, 2003, Circulation, 108, 2941-2948). However, the mechanisms involved in these effects have not been well described but the nature of the presentation suggests an integrated physiological response which includes an effect on renal salt and water balance. PPAR gamma receptors have been found in the renal collecting duct (Guan Y. et al; 2001, Kidney Int. 60, 14-30) and, therefore, the PPAR gamma agonists might be involved directly in renal tubular metabolism or could have secondary effects on salt and water homeostasis. The PPAR gamma agonist pioglitazone has been suggested as a treatment of psoriasis in, e.g., British Journal of Dermatology 2005 152, pp 176-198.

Nuclear factor erythroid-2 related factor 2 or Nuclear Factor E2p45-Related Factor (Nrf2) is a cap-and-collar basic leucine zipper transcription factor, regulates a transcriptional program that maintains cellular redox homeostasis and protects cells from oxidative insult (Rangasamy T, et al., J Clin Invest 114, 1248 (2004); Thimmulappa R K, et al. Cancer Res 62, 5196 (2002); So H S, et al. Cell Death Differ (2006)). NRF2 activates transcription of its target genes through binding specifically to the antioxidant-response element (ARE) found in those gene promoters. The NRF2-regulated transcriptional program includes a broad spectrum of genes, including antioxidants, such as γ-glutamyl cysteine synthetase modifier subunit (GCLm), γ-glutamyl cysteine synthetase catalytic subunit (GCLc), heme oxygenase-1, superoxide dismutase, glutathione reductase (GSR), glutathione peroxidase, thioredoxin, thioredoxin reductase, peroxiredoxins (PRDX), cysteine/glutamate transporter (SLC7A11) (7, 8)], phase II detoxification enzymes [NADP (H) quinone oxidoreductase 1 (NQO1), GST, UDP-glucuronosyltransferase (Rangasamy T, et al. J Clin Invest 114: 1248 (2004); Thimmulappa R K, et al. Cancer Res 62: 5196 (2002)), and several ATP-dependent drug efflux pumps, including MRP1, MRP2 (Hayashi A, et al. Biochem Biophy Res Commun 310: 824 (2003)); Vollrath V, et al. Biochem J (2006)); Nguyen T, et al. Annu Rev Pharmacol Toxicol 43: 233 (2003)).

Interlinked with Nrf2 is KEAP1, which is a cytoplasmic anchor of Nrf2 that also functions as a substrate adaptor protein for a Cul3-dependent E3 ubiquitin ligase complex to maintain steady-state levels of NRF2 and NRF2-dependent transcription (Kobayashi et al., Mol Cell Biol 24: 7130 (2004); Zhang D, et al. Mol Cell Biol 24: 10491 (2004)). The KEAP1 gene is located at human chromosomal locus 19p13.2. The KEAP1 polypeptide has three major domains: (1) an N-terminal Broad complex, Tramtrack, and Bric-a-brac (BTB) domain; (2) a central intervening region (IVR); and (3) a series of six C-terminal Kelch repeats (Adams J, et al. Trends Cell Biol 10:17 (2000)). The Kelch repeats of KEAP1 bind the Neh2 domain of Nrf2, whereas the IVR and BTB domains are required for the redox-sensitive regulation of Nrf2 through a series of reactive cysteines present throughout this region (Wakabayashi N, et al. Proc Natl Acad Sci USA 101: 2040 (2004)). KEAP1 constitutively suppresses Nrf2 activity in the absence of stress. Oxidants, xenobiotics and electrophiles hamper KEAP1-mediated proteasomal degradation of Nrf2, which results in increased nuclear accumulation and, in turn, the transcriptional induction of target genes that ensure cell survival (Wakabayashi N, et al. Nat Genet. 35: 238 (2003)). Prothymosin a, a novel binding partner of KEAP1, has been shown to be an intranuclear dissociator of the NRF2-KEAP1 complex and can upregulate the expression of Nrf2 target genes (Karapetian R N, et al. Mol Cell Biol 25: 1089 (2005)). Certain interactions between Nrf2 and PPAR gamma have been suggested, e.g., in Am J Respir Crit Care Med 2010; 182:170-182.

Nrf2 activators according to the present invention are agents that after administration result in a stimulated and/or increased nuclear translocation of Nrf2 protein and causes the subsequent increases in gene products that detoxify and eliminate cytotoxic metabolites. Nrf2 activators according to the present invention may act directly on Nrf2, KEAP1, the NRF2-KEAP1 complex and/or otherwise. Nrf2 activators of the present invention may comprise a Michael addition acceptor, one or more fumaric acid esters, i.e., fumaric acid mono- and/or diesters which are preferably selected from the group of monoalkyl hydrogen fumarates and dialkyl fumarates (such as monomethyl hydrogen fumarate, dimethyl fumarate, monoethyl hydrogen fumarate, and diethyl fumarate), ethacrynic acid, bardoxolone methyl (methyl 2-cyano-3,12-dioxooleana-1,9(11)dien-28-oate), isothiocyanate such as sulforaphane, 1,2-dithiole-3-thione such as oltipraz, 3,5-di-tert-butyl-4-hydroxytoluene, 3-hydroxycoumarin, or a pharmacologically active derivative or analog of the aforementioned agents.

Very preferred Nrf2 activators for use in combination with PPAR gamma agonists according to the present invention are bardoxolone methyl and fumaric acid esters.

Fumaric acid esters are approved in Germany for the treatment of psoriasis, are being evaluated in the United States for the treatment of psoriasis and multiple sclerosis, and have been proposed for use in treating a wide range of immunological, autoimmune, and inflammatory diseases and conditions. FAEs and other fumaric acid derivatives have been proposed for use in treating a wide variety of diseases and conditions involving immunological, autoimmune, and/or inflammatory processes including psoriasis (Joshi and Strebel, WO 1999/49858; U.S. Pat. No. 6,277,882; Mrowietz and Asadullah, Trends Mol Med 2005, 111(1), 43-48; and Yazdi and Mrowietz, Clinics Dermatology 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al, Arch Dermatol Res 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034). All of these indications and diseases can be treated or prevented with the combination treatment of the present invention.

Fumaderm®, an enteric coated tablet containing a salt mixture of monoethyl fumarate and dimethylfumarate, which is rapidly hydrolyzed to monomethyl fumarate, was approved in Germany in 1994 for the treatment of psoriasis. Fumaderm® is dosed TID with 1-2 grams/day administered for the treatment of psoriasis.

Biogen Idec Inc. is presently evaluating dimethyl fumarate under the product name BG-12 in the treatment of relapsing-remitting multiple sclerosis. The drug is under review with U.S. and European regulators.

Fumaric acid derivatives (Joshi and Strebel, WO 2002/055063, US 2006/0205659, and U.S. Pat. No. 7,157,423 (amide compounds and protein-fumarate conjugates); Joshi et al., WO 2002/055066 and Joshi and Strebel, U.S. Pat. No. 6,355,676 (mono and dialkyl esters); Joshi and Strebel, WO 2003/087174 (carbocyclic and oxacarbocylic compounds); Joshi et al., WO 2006/122652 (thiosuccinates); Joshi et al., US 2008/0233185 (dialkyl and diaryl esters) and Nilsson et al., US 2008/0004344 (salts)) have been developed in an effort to overcome the deficiencies of current therapy with fumaric acid esters. Controlled release pharmaceutical compositions comprising fumaric acid esters are disclosed by Nilsson andller, WO 2007/042034. Prodrugs are described by Nielsen and Bundgaard, J Pharm Sci 1988, 77(4), 285-298 and WO2010/022177.

DETAILED DESCRIPTION

Preferably, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms (C1-20) in certain embodiments from 1 to 10 carbon atoms (C1-10), in certain embodiments from 1 to 8 carbon atoms (C1-8), in certain embodiments from 1 to 6 carbon atoms (C1-6), in certain embodiments from 1 to 4 carbon atoms (C1-4), and in certain embodiments from 1 to 3 carbon atoms (C1-3). The term "alkoxy" refers to a group O-alkyl, wherein alkyl has the meaning indicated above. The term "perfluoroalkyl" refers to an alkyl group wherein all hydrogen atoms have been replaced by fluoro.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease, or reducing the risk of developing a disease or at least one of the clinical symptoms of a disease. "Treating" or "treatment" also refers to inhibiting the disease, either physically (e.g., stabilization of a discernible symptom), physiologically (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient who may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to effect such treatment of the disease or symptom thereof. The "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Throughout the specification, the term "isolated Nrf2 activator" preferably refers to an Nrf2 activator which, if naturally occurring, is substantially separated from other components and other molecules which naturally accompany the respective Nrf2 activator. The term embraces an Nrf2 activator which has been removed from its naturally occurring environment or its natural state through purifying steps that separate other molecules naturally associated with it, e.g., by known conventional methods such as chromatography, crystallization and distillation. The term "isolated Nrf2 activator" preferably still allows for the Nrf2 activator to be in admixture with various amounts of water, such as up to about 20 weight %. The term "isolated Nrf2 activator" preferably excludes such Nrf2 activators which are still in their natural state, e.g., which are still contained in their source of origin or parts thereof, such as a plant, irrespective of whether or not this source of origin has been dried. Moreover, the term "isolated Nrf2 activator" preferably refers to a natural or synthetically prepared molecule which has a purity of above 70 weight %, preferably of above 80 weight % and more preferably of above 90 weight %, such as about 95 weight %, about 97 weight % or about 99 weight %, before being formulated in a pharmaceutical composition, if so desired. In case the Nrf2 activator is naturally occurring, e.g., as a natural product, it is preferably an isolated Nrf2 activator, i.e., not in form of, e.g., an herbal preparation.

In case the PPAR gamma agonist is naturally occurring, e.g., as a natural product, it is preferably an isolated PPAR gamma agonist, i.e., not in form of, e.g., an herbal preparation.

Reference is now made in detail to certain embodiments of compounds, compositions, and methods. The disclosed embodiments are not intended to be limiting of the claims.

According to the present invention, strongly improved treatment results are obtained in the treatment of autoimmune and/or inflammatory diseases when a PPAR agonist and preferably a PPAR gamma agonist and an Nrf2 activator are used in the treatment of the disease in combination as compared to treatment with a PPAR gamma agonist or an Nrf2 activator alone. Co-administration of a PPAR gamma agonist and an Nrf2 activator or an administration of a fixed dose combination of a PPAR gamma agonist and an Nrf2 activator results in an improved therapeutic effect, which may be a more than additive effect, compared to the administration of a PPAR gamma agonist or Nrf2 activators, respectively, as mono-therapy.

In particular, it has been found that the advantageous therapeutic results in inflammatory and/or autoimmune diseases resulting from use of compounds such as dexamethasone, having both PPAR gamma agonistic and Nrf2 activating effects, can be matched or even surpassed by the combination treatment of the present invention, wherein at least two individual and different compounds, each having either PPAR gamma agonistic or Nrf2 activating effects, are employed. Thus, a combination treatment comprising at least one PPAR gamma agonist, which may have no significant or only a minor modulating or activating effect on Nrf2, and at least one Nrf2, which may have no significant or only a minor modulating or activating effect on PPAR gamma, result in improved and synergistic therapeutic effects, as compared to the administration of such PPAR gamma agonist or such Nrf2 activator, respectively, as mono-therapy. The synergistic effect is often more pronounced with such combinations, where the agents employed are predominantly either PPAR gamma agonists or Nrf2 activators, which each have no significant activity on the respective other target. Nevertheless, even in those cases where one or both of the agents display significant PPAR gamma agonistic and Nrf2 activating effects at the same time, such as in the case of dexamethasone and 15-deoxy-delta(12,14)-prostaglandin J(2) (15d-PGJ(2)), the combination treatment according to the present invention can lead to improved treatment results over the mono-therapy. A compound having dual effects on the targets PPAR gamma and Nrf2 is unlikely to show an ideally distributed effect on both targets for therapeutic use. By applying the present invention each target can be addressed individually and activated with suitable and appropriate concentrations of the respective agents.

Thus, embodiments are preferred wherein at least one agent is not both PPAR gamma agonist and Nrf2 activator at the same time.

Combination treatments and fixed dose combinations according to the present invention are preferred, which comprise at least two different agents having either PPAR gamma agonistic or Nrf2 activating effects at the concentration used in the combination.

The present invention relates to combination treatments, compositions containing the inventive combination of agents and related fixed-dose combinations, wherein the PPAR agonist, such as the PPAR gamma agonist, and the Nrf2 activator are different compounds which preferably have a different chemical structure, e.g., have a difference in carbon atoms of at least 3 carbon atoms, preferably at least 5 or at least 10 carbon atoms, and are not belonging to the same chemical class. Throughout this specification, the use of a singular also includes the plural, if not indicated otherwise.

Preferred PPAR agonists are compounds having a PPAR gamma agonistic effect without significantly activating Nrf2. These are preferably compounds having no ability to form covalent bonds with organic thiol groups under physiological conditions, such as with glutathione. Thus, preferred PPAR gamma agonists are compounds that, contrary to, e.g., 15-deoxy-delta(12,14)-prostaglandin J(2) (15d-PGJ (2)), cannot bind covalently through, e.g., Michael addition reaction to the PPA receptor. Most preferred PPAR agonists are glitazones, glitazars and sartans.

PPAR agonists are PPAR activators (e.g., PPAR gamma agonists are PPAR gamma activators). The definition of "PPAR agonist" and "PPAR gamma agonist" according to the present invention preferably includes such agonists, i.e., compounds, that directly bind to the PPA receptor and have an agonistic, i.e., activating effect, as well as so-called physiological PPAR agonists and physiological PPAR gamma agonists, which do not necessarily bind to the PPAR receptor, but result in an activation of PPAR through other pathways, such as by increasing the concentration of endogenous PPAR gamma agonist 15-deoxy-Delta(12,14)-prostaglandin J(2) (15d-PGJ(2).

A large number of natural and synthetic PPAR agonists are known (see, e.g., Michalik et al. (2006) Pharmacological Reviews 58:726-725; Gilde et al. (2003) Circulation Research 92(5):518-524; Peraza et al. (2005) Toxicological Sciences 90(2):269-295; and Desvergne & Wahli (1999) Endocrine Reviews 20(5):649-688). Some of these known agonists are specific for a single PPAR isotype, while others target multiple PPAR subtypes. PPAR agonists are preferred, if the PPAR agonist more strongly activates PPAR gamma or PPAR gamma and PPAR alpha simultaneously than other isoforms.

In one embodiment, the PPAR agonist may be selected from the group consisting of PPAR gamma agonists, such as glitazones, and dual PPAR alpha/gamma agonists, such as glitazars. In yet further embodiments, the glitazone may be selected from the group consisting of troglitazone, pioglitazone, rosiglitazone, ciglitazone, englitazone, darglitazone, netoglitazone, isaglitazone, MC-555, balaglitazone, rivoglitazone, and the like. In yet further embodiments, the glitazar may be selected from the group consisting of muraglitazar, naveglitazar, tesaglitazar, ragaglitazar, reglitazar and farglitazar. In yet further embodiments, PPAR agonists are selected from berberine, K-111, INT-131 (2,4-di chloro-N-(3,5-dichloro-4-quinolin-3-yloxyphenyl)benzenesulfonamide), MBX-102 (metaglidasen; 2-acetamidoethyl (2R)-2-(4-chlorophenyl)-2-[3-(trifluoromethyl)phenoxy]acetate), MBX-2044, FK614 (3-(2,4-dichlorobenzyl)-2-methyl-N-(pentylsulfonyl)-3H-benzimidazole-5-carboxamide), GSK-376501 (1-[[3,5-bis(2-methoxyethoxy)phenyl]methyl]-3-(4-tert-butylphenyl)indole-2-carboxylic acid), GW 1929 ((2 S)-2-(2-benzoylanilino)-3-[4-[2-[methyl(pyridin-2-yl) amino]ethoxy]phenyl]propanoic acid), S26948 (dimethyl 2-[[4-[2-(6-benzoyl-2-oxo-1,3-benzothiazol-3-yl)ethoxy] phenyl]methyl]propanedioate), psi-baptigenin and the like, such as those disclosed in U.S. Pat. No. 5,002,953, U.S. Pat. No. 4,687,777 and U.S. Pat. No. 5,965,584. Pioglitazone and rosiglitazone are very preferred and most preferred are pioglitazone hydrochloride and rosiglitazone maleate.

In a further preferred embodiment of the present inventions, PPAR gamma agonists are selected from the class of statins or HMG-CoA reductase inhibitors, preferably selected from atorvastatin, fluvastatin, lovastatin, pravastatin, rosuvastatin, simvastatin, mevastatin and pitavastatin. Statins are a class of drugs used to lower cholesterol levels by inhibiting the enzyme HMG-CoA reductase, which plays a central role in the production of cholesterol in the liver. Increased cholesterol levels have been associated with cardiovascular diseases, and statins are therefore used in the prevention of these diseases. Statins have also been suggested for the treatment of multiple sclerosis (e.g., US 2004/0013643). Although statins are believed to activate PPAR gamma only indirectly (Circ Res. 2007; 100:1442-1451), as physiological PPAR gamma agonists they are included in the definition of PPAR gamma agonists for the purposes of the present invention.

In a further preferred embodiment of the present invention, PPAR gamma agonists are selected from the chemical class of sartans, also known as angiotensin II receptor antagonists, angiotensin receptor blockers (ARBs) or AT1-receptor antagonists. Sartans, such as valsartan, losartan, azilsartan, irbesartan, olmesartan, telmisartan, candesartan and eprosartan, are a group of pharmaceuticals which modulate the renin-angiotensin-aldosterone system. Preferred sartans used in the present invention are selected from losartan, irbesartan, telmisartan and candesartan, which have shown to bind to and activate PPAR gamma (Drug Development Research 67:579-581, 2006). Treatment with sartans has been suggested to improve multiple sclerosis. The sartans are predominantly used in the treatment of hypertension, diabetic nephropathy (kidney damage due to diabetes) and chronic kidney disease as well as congestive heart failure and are also preferably employed for these diseases and conditions when combined with Nrf2 activators according to the present invention.

In a further preferred embodiment of the present inventions, PPAR gamma agonists are selected from nonsteroidal anti-inflammatory drugs (NSAIDs) having PPAR gamma activating properties, preferably indomethacin, flufenamic acid, fenoprofen and ibuprofen (The Journal of Biological Chemistry, vol. 272, no. 6, issue 7, pp. 3406-3410, 1997). NSAIDs are included in the definition of PPAR gamma agonists for the purposes of the present invention as they may bind directly to the PPAR or act as a physiological PPAR gamma agonist. In one embodiment, NSAIDs other than aspirin are preferred.

The group of NSAIDs comprises the following compounds: Salicylates, such as aspirin (acetylsalicylic acid), diflunisal, and salsalate; propionic acid derivatives such as ibuprofen, dexibuprofen, naproxen, fenoprofen, ketoprofen, dexketoprofen, flurbiprofen, oxaprozin, and loxoprofen; acetic acid derivatives such as indomethacin, sulindac, etodolac, ketorolac, diclofenac, and nabumetone; enolic acid (oxicam) derivatives such as piroxicam, meloxicam, tenoxicam, droxicam, lornoxicam, and isoxicam; fenamic acid derivatives (fenamates) such as mefenamic acid, meclofenamic acid, flufenamic acid, and tolfenamic acid; selective cox-2 inhibitors (coxibs) such as celecoxib, rofecoxib, valdecoxib, parecoxib, lumiracoxib, etoricoxib, and firocoxib; sulphonanilides such as nimesulide; and others such as licofelone and lysine clonixinate.

Nrf2-activating compounds can be classified based on their chemical structures: Diphenols, Michael reaction acceptors, isothiocyanates, thiocarbamates, trivalent arsenicals, 1,2-dithiole-3-thiones, hydroperoxides, vicinal dimercaptans, heavy metals, and polyenes. Moreover, Nrf2 activators: (i) are all chemically reactive; (ii) are nearly all electrophiles; (iii) are mostly substrates for glutathione transferases; and (iv) can all modify sulfhydryl groups by alkylation, oxidation, or reduction (PNAS Feb. 17, 2004 vol. 101 no. 7 2040-2045, Mol. Cell. Biol. 2009, 29(2):493). The activity of the compounds can be identified by known methods.

Preferred Nrf2 activators are compounds without significant PPAR gamma agonistic effect. These are preferably compounds which may or may not bind covalently to the PPA receptor, but are not able to change the conformation of the PPAR and preferably the PPA gamma receptor to an extent that this would result in an activation of the PPA receptor. According to the present invention these preferred Nrf2 activators are small and of low molecular weight. These compounds preferably lack the structural elements to bind to the PPA receptor non-covalently with the result of a change of conformation and activation of the PPA receptor. In a preferred embodiment, the Nrf2 activators may be able to bind covalently to the PPA receptor, e.g., via a Michael reaction with a thiol group of the PPA receptor, without resulting in a conformation change of the PPA receptor. Due to their limited size, however, these preferred Nrf2 activators may not prevent PPAR agonists, and in particular PPAR gamma agonists, especially glitazones such as pioglitazone or rosiglitazone, from binding non-covalently to the PPA receptor with the result of a conformation change.

In a very preferred example, the covalent binding of an Nrf2 activator such as monomethyl hydrogen fumarate or dimethyl fumarate and the non-covalent binding of a PPAR gamma agonist such as a glitazone, like pioglitazone or rosiglitazone, leads to synergistic and strongly improved therapeutic results.

In one embodiment, the preferred Nrf2 activators are selected from organic compounds having not more than one or two 5- or 6-membered carbocyclic rings or 5- or 6-membered heterocyclic rings having 1, 2 or 3 N-, O- or S-atoms as ring atoms which may be fused to each other or preferably no or only one carbocyclic or heterocyclic ring and/or less than 35, preferably less than 30, more preferably less than 25, most preferably less than 20, even less than 15 or less than 10 carbon atoms and/or have a molecular weight of less than 400, preferably less than 300, most preferably less than 200 g/mol or less than 170 g/mol and are selected from the chemical classes of Michael reaction acceptors, phenols, diphenols, chalcones, isothiocyanates, thiocarbamates, quinones, naphthoquinones and 1,2-dithiole-3-thiones, wherein one or more, preferably up to seven, H-atoms may be substituted by linear or branched alkyl and perfluoroalkyl, such as methyl, ethyl, trifluoromethyl, halogen such as Br, Cl, F or I, hydroxy, alkoxy and perfluoroalkoxy, such as methoxy, ethoxy, trifluoromethoxy, cyano and nitro.

In cases where compounds of the chemical class of quinones are employed as Nrf2 activators, the respective hydroquinones can be used alternatively. However, the respective oxidized form, i.e., the respective quinone, is preferred. The Nrf2 activity can be determined according to e.g., JALA 2008; 13: 243-248. Bardoxolone methyl and derivatives are described in U.S. Pat. No. 8,129,429, U.S. Pat. No. 7,435,755 and US2009/0060873. Amorphous bardoxolone methyl and suitable formulations are disclosed in WO2010/093944.

Very preferred Nrf2 activators are capable of provoking or inducing a stimulated and/or increased nuclear translocation of Nrf2 protein and are:
 a) selected from the group of Michael reaction acceptors, phenols, diphenols, chalcones, isothiocyanates, thiocarbamates, quinones, naphthoquinones and 1,2-dithiole-3-thiones; and
 b) contain less than 35 carbon atoms; and/or
 c) have a molecular weight of less than 600 g/mol; and/or
 d) contain no or not more than one or two fused or monocyclic 5- or 6-membered carbocyclic or heterocyclic rings, having 1, 2 or 3 ring atoms selected from N, O or S.

In these preferred Nrf2 activators, one or more, preferably up to seven, H-atoms may be substituted preferably by linear or branched alkyl and perfluoroalkyl, such as methyl, ethyl, trifluoromethyl, halogen such as Br, Cl, F or I, hydroxy, alkoxy and perfluoroalkoxy, such as methoxy, ethoxy, trifluoromethoxy, cyano and nitro.

More preferred embodiments of these Nrf2 activators contain no ring system or only one or two rings, which may be carbocyclic and/or heterocyclic rings. Even more preferred Nrf2 activators contain less than 30, more preferably less than 25, most preferably less than 20, even less than 15 or less than 10 carbon atoms and/or have a molecular weight of less than 400 g/mol, more preferably less than 300 g/mol and most preferably less than 200 g/mol or less than 170 g/mol. Further preferred Nrf2 activators bind covalently to KEAP1 protein, preferably via an S-atom of the protein's amino acids.

Preferred Michael reaction acceptors are ketones, aldehydes, carboxylic acid esters and carboxylic acid amides, all of which are alpha, beta unsaturated.

More preferred Nrf2 activators are the compounds A to Z given below, including their tautomers and stereoisomers:

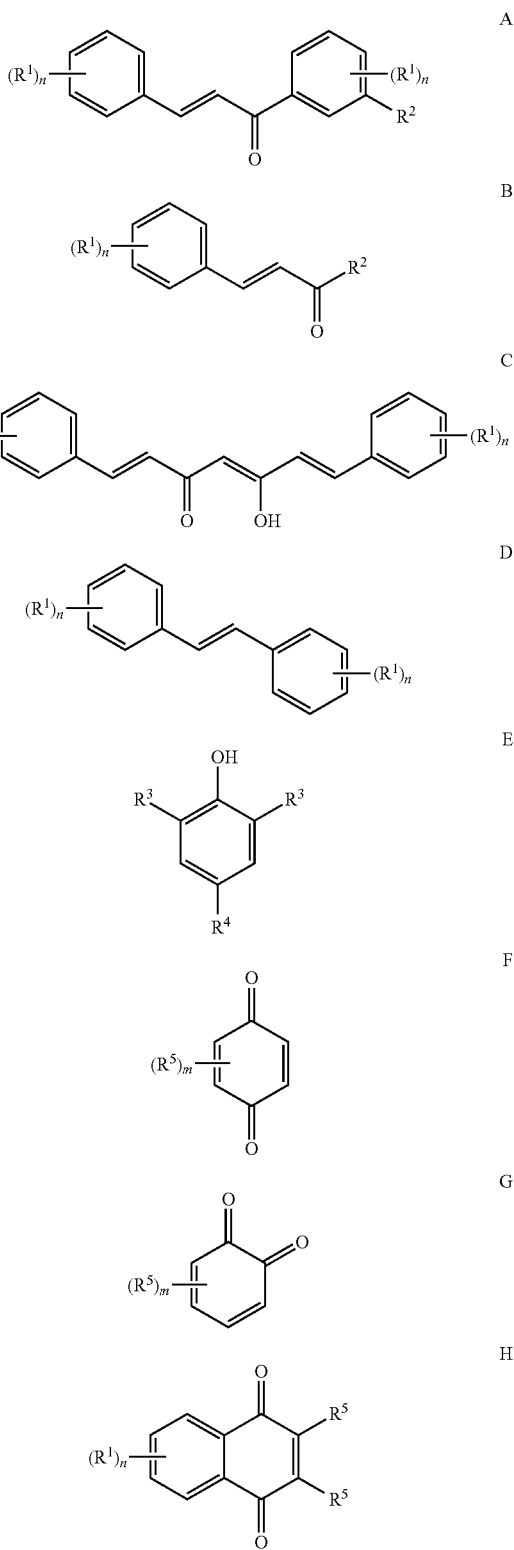

-continued

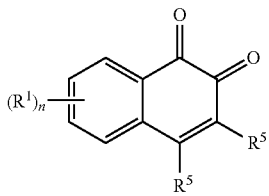
I

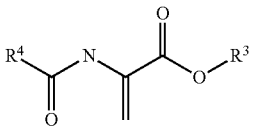
T

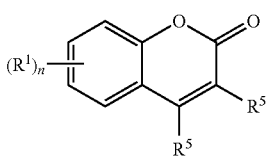
J

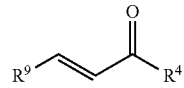
U

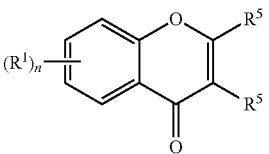
K

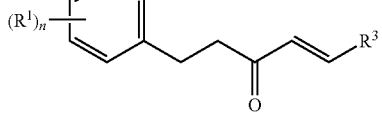
V

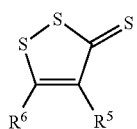
L

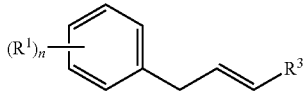
W

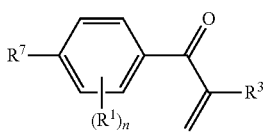
M

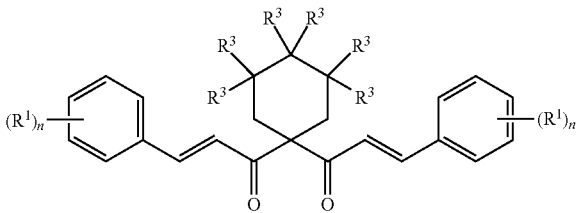
X

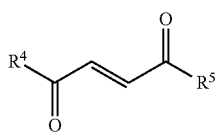
N

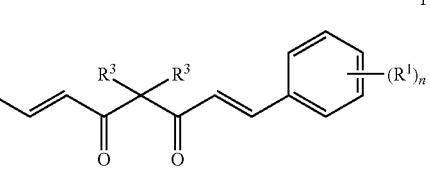
Y

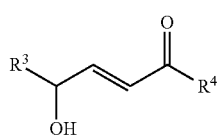
O

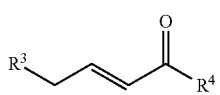
P

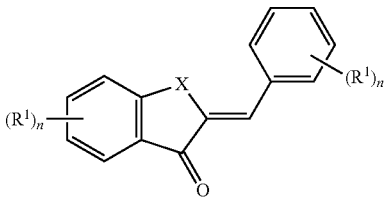
Z

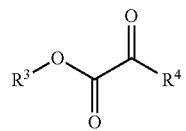
Q

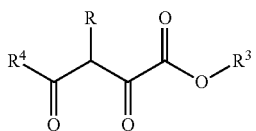
R

S wherein the individual radicals have the meaning given below:

$R^1$ H, OH, Hal, CN, A, perfluoroalkyl, perfluoroalkoxy
$R^2$ H, OH, A, alkoxy, amino
$R^3$ H, alkyl
$R^4$ H, OH, alkyl, alkoxy
$R^5$ H, OH, A, alkoxy
$R^6$ H, A, alkoxy, aryl, het
$R^7$ H, OH, A, alkoxy
$R^8$ A
$R^9$ Het
X O, NH, S
m 1, 2
n 1, 2, 3
Hal is F, Cl, Br or I, preferably F or Cl.
A is preferably alkyl, which denotes a straight or branched carbon chain having 1, 2, 3, 4, 5, 6, 7, 8, 9, 10, 11, or 12 carbon atoms. Alkyl preferably denotes methyl, ethyl, propyl, isopropyl, butyl, isobutyl, sec-butyl or tert-butyl, or pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, or 1,1,2- or 1,2,2-trimethylpropyl. Alternatively, A denotes cycloalkyl having 3, 4, 5, 6 or 7 carbon atoms or branched or linear alkyl having 2 to 12 C-atoms, wherein one or more, preferably 1 to 7, H-atoms may be replaced by Hal, alkyl, alkoxy, cycloalkyl, phenyl, p-, m- or o-hydroxyphenyl, p-, m- or o-alkoxyphenyl, $N(R^3)_2$, OH, $CO_2H$, or $CF_3$, and/or wherein one or more, preferably 1 to 7, non-adjacent $CH_2$-groups may be replaced by —O—, —S—, —SO—, —$NR^3$—, —CO—, —$CO_2$—, —CH=CH—S— and/or —CH=CH—. Cycloalkyl preferably denotes cyclopropyl, cyclobutyl, cyclopentyl, cyclohexyl or cycloheptyl.

Alkoxy is preferably a group O-alkyl, wherein alkyl is defined as above. Preferably, alkoxy denotes a group —O—$(CH_2)_n$—$CH_3$, wherein n is 0, 1, 2, 3 or 4, more preferably methoxy or ethoxy.

Perfluoroalkyl preferably denotes a straight or branched alkyl chain having 1 to 8 carbon atoms, preferably 1 to 6 carbon atoms, and wherein all hydrogen atoms are replaced by F atoms, preferably, for example, trifluoromethyl or pentafluoroethyl.

Perfluoroalkoxy is preferably a group O-perfluoroalkyl, wherein perfluoroalkyl is defined as above. Perfluoroalkoxy preferably denotes $OCF_3$.

Amino denotes preferably the group —NR'R" where each R', R" is independently hydrogen or alkyl. The group —NR'R" can also form a cyclic group selected from piperidinyl, piperazinyl, pyrrolyl or morpholinyl, wherein one, two or three H atoms may be substituted by alkyl, such as methyl. In one embodiment, amino denotes dialkylamino, wherein alkyl has the meaning given above and is preferably dimethylamino.

Aryl preferably denotes a monocyclic or bicyclic, aromatic carbocyclic ring having 6 to 14 carbon atoms, which is unsubstituted or monosubstituted, disubstituted or trisubstituted by F, Cl, Br, $CF_3$, $OCF_3$, $NO_2$, CN, alkyl, alkoxy, OH, amino, CO-amino, NHCO-alkyl, CO-alkyl, CO-alkoxy, $SO_2$-alkyl, or $SO_2$-amino. Most preferably, aryl denotes unsubstituted or monosubstituted phenyl.

Het preferably denotes, notwithstanding further substitutions, a 6- to 14-membered monocyclic or bicyclic saturated, unsaturated or aromatic heterocyclic ring system containing 1 or 2 heteroatoms selected from N, O and S, which is unsubstituted or monosubstituted, disubstituted or trisubstituted by F, Cl, Br, $CF_3$, $OCF_3$, $NO_2$, CN, alkyl, alkoxy, OH, amino, CO-amino, NHCO-alkyl, CO-alkyl, CO-alkoxy, $SO_2$-alkyl, or $SO_2$-amino. More preferably, Het is 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, or 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxa-diazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, or 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl. The heterocyclic radicals may also be partially or fully hydrogenated. Het can thus also denote, for example, 2,3-dihydro-2-, -3-, 4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or 3,4-dihydro-2H-1,5-benzodioxepin-6- or -'7-yl, furthermore preferably 2,3-dihydrobenzofuranyl or 2,3-dihydro-2-oxofuranyl. Very preferably, heteroaryl is unsubstituted or monosubstituted 2-pyridyl, pyrimidyl or imidazolyl.

$R^1$ is preferably H, OH, F, methyl, methoxy, or trifluoromethoxy.

$R^2$ is preferably H, OH, alkoxy, such as methoxy, or $OCH_2CH_2$-phenyl.

$R^3$ is preferably H or alkyl, preferably H, methyl or tert-butyl.

$R^4$ is preferably H, OH, or alkoxy, such as methoxy.

$R^5$ is preferably H or A.

$R^6$ is preferably H or Het.

$R^7$ is preferably $(CH_2)_m COR^2$, $(CH_2)_m COR^2$, $O(CH_2)_m COR^2$ or $O(CH_2)_m COR^2$.

$R^8$ is preferably allyl or a group selected from $(C(R^3)_2)_q$S-alkyl or $(C(R^3)_2)_q$SO-alkyl, wherein q is 1, 2, 3, 4, 5, 6, 7, 8, 9, 10, 11 or 12.

Preferred Nrf2 activators are selected from chalcone derivatives as disclosed in J. Med. Chem., 2011, 54 (12), pp 4147-4159, such as 2-trifluoromethyl-2'-methoxychalcone, auranofin (as contained in the FDA-approved drug Ridaura), ebselen, 1,2-naphthoquinone, cinnamic aldehyde, caffeic acid and its esters, curcumin, resveratrol, artesunate, tert-butylhydroquinone, and -quinone, (tBHQ, tBQ), vitamins K1, K2 and K3, preferably menadione, fumaric acid esters, i.e., fumaric acid mono- and/or diester which is preferably selected from the group of monoalkyl hydrogen fumarate and dialkyl fumarate, such as monomethyl hydrogen fumarate, dimethyl fumarate, monoethyl hydrogen fumarate, and diethyl fumarate, 2-cyclopentenones, ethacrynic acid and its alkyl esters, bardoxolone methyl (methyl 2-cyano-3,12-dioxooleana-1,9(11)dien-28-oate) (CDDO-Me, RTA 402), ethyl 2-cyano-3,12-dioxooleana-1,9(11)dien-28-oate, 2-cyano-3,12-dioxooleana-1,9(11)dien-28-oic acid (CDDO), 1[2-Cyano-3,12-dioxooleana-1,9(11)-dien-28-oyl]imidazole (CDDO-Im), (2-cyano-N-methyl-3,12-dioxooleana-1,9(11)-dien-28 amide (CDDO-methyl amide, CDDO-MA), isothiocyanate such as sulforaphane, 1,2-dithiole-3-thione such as oltipraz, capsaicin, 3,5-di-tert-butyl-4-hydroxytoluene, 3-hydroxycoumarin, cromolyn sodium or any other salt thereof, nedocromil or its salt such as the sodium salt, 4-hydroxynonenal, 4-oxononenal, malondialdehyde, (E)-2-hexenal, capsaicin, allicin, allylisothiocyanate, 6-methylthiohexyl isothiocyanate, 7-methylthioheptyl isothiocyanate, sulforaphane, 8-methylthiooctyl isothiocyanate, corticosteroids, such as dexamethasone, 8-iso prostaglandin A2, alkyl pyruvate, such as methyl and ethyl pyruvate, diethyl or dimethyl oxalopropionate, 2-acetamidoacrylate, methyl or ethyl-2-acetamidoacrylate, hypoestoxide, parthenolide, eriodictyol, 4-Hydroxy-2-nonenal, 4-oxo-2-nonenal, geranial, zerumb one, aurone, isoliquiritigenin, xanthohumol, [10]-Shogaol, eugenol, 1'-acetoxychavicol acetate, allyl isothiocyanate, benzyl isothiocyanate, phenethyl isothiocyanate, 4-(Methylthio)-3-butenyl isothiocyanate and 6-Methylsulfinylhexyl isothiocyanate, ferulic acid and its esters, such as ferulic acid ethyl ester, and ferulic acid methyl ester, sofalcone, 4-methyl daphnetin, imperatorin, auraptene, poncimarin, bis[2-hydroxybenzylidene]acetones, alicylcurcuminoid, 4-bromo flavone, 3-naphthoflavone, sappanone A, aurones and its corresponding indole derivatives such as benzylidene-indolin-2-ones, perillaldehyde, quercetin, fisetin, koparin, genistein, tanshinone IIA, BHA, BHT, PMX-290, AL-1, avicin D, gedunin, fisetin, andrographolide, [(±)-(4bS,8aR,10aS)-10a-ethynyl-4b, 8, 8-trimethyl-3,7-dioxo-3,4b,7,8,8a,9,10,10a-octahydrophenanthrene-2,6-dicarbonitrile] (TBE-31), 2-cyano-3,12-dioxooleana-1,9(11)-dien-28-onitrile (TP-225), [(±)-(4bS,8aR,10aS)-10a-ethynyl-4b,8,8-trimethyl-3,7-dioxo-3,4b,7,8,8a,9,10,10a-octahydrophenanthrene-2,6-dicarbonitrile] (TBE-31), (TP-225), MCE-1, MCES, ADT as referred to in Medicinal Research Reviews, 32, No. 4, 687-726, 2012, gallic acid esters, such as alkyl esters, preferably ethyl gallate, n-propyl gallate and octyl gallate, or epigallocatechingallate, caffeic acid esters such as alkyl esters or its phenethyl ester, Coenzyme Q10 (Ubiquinone, Ubidecarenone), and the respective quinone or hydroquinone forms of the aforementioned quinone and hydroquinone derivatives and stereoisomers, tautomers or pharmacologically active derivatives of the aforementioned agents, such as the respective phenyl esters, alkyl esters, and alkanoyl esters and benzoyl ethers, phenyl ethers and alkyl ethers.

Very preferred Nrf2 activators are selected from carnosic acid, 2-naphthoquinone, cinnamic aldehyde, caffeic acid and its esters, curcumin, resveratrol, artesunate, tert-butylhydroquinone, vitamins K1, K2 and K3, fumaric acid esters, i.e., fumaric acid mono- and/or diester, which is preferably selected from the group of monoalkyl hydrogen fumarate and dialkyl fumarate, such as monomethyl hydrogen fumarate, dimethyl fumarate, monoethyl hydrogen fumarate, and diethyl fumarate, isothiocyanate such as sulforaphane, 1,2-dithiole-3-thione such as oltipraz, capsaicin, 3,5-di-tert-butyl-4-hydroxytoluene, 3-hydroxycoumarin, 4-hydroxynonenal, 4-oxononenal, malondialdehyde, (E)-2-hexenal, capsaicin, allicin, allylisothiocyanate, 6-methylthiohexyl isothiocyanate, 7-methylthioheptyl isothiocyanate, sulforaphane, 8-methylthiooctyl isothiocyanate, 8-iso prostaglandin A2, alkyl pyruvate, such as methyl and ethyl pyruvate, diethyl or dimethyl oxalopropionate, 2-acetamidoacrylate, methyl or ethyl-2-acetamidoacrylate, hypoestoxide, parthenolide, eriodictyol, 4-Hydroxy-2-nonenal, 4-oxo-2-nonenal, geranial, zerumbone, aurone, isoliquiritigenin, xanthohumol, [10]-Shogaol, eugenol, 1'-acetoxychavicol acetate, allyl isothiocyanate, benzyl isothiocyanate, phenethyl isothiocyanate, 4-(Methylthio)-3-butenyl isothiocyanate and 6-Methylsulfinylhexyl isothiocyanate and the respective quinone or hydroquinone forms of the aforementioned quinone and hydroquinone derivatives and stereoisomers, tautomers or pharmacologically active derivatives of the aforementioned agents. Very preferred Nrf2 activators are Michael reaction acceptors such as dimethyl fumarate, monomethyl hydrogen fumarate isothiocyanates and 1,2-dithiole-3-thiones. In another embodiment, very preferred Nrf2 activators are selected from monomethyl hydrogen fumarate, dimethyl fumarate, oltipraz, 1,2-naphthoquinone, tert-butylhydroquinone, methyl and ethyl pyruvate, 3,5-di-tert-butyl-4-hydroxytoluene, diethyl and dimethyl oxalopropionate, hypoestoxide, parthenolide, eriodictyol, 4-hydroxy-2-nonenal, 4-oxo-2-nonenal, geranial, zerumbone, aurone, isoliquiritigenin, xanthohumol, [10]-Shogaol, eugenol, 1'-acetoxychavicol acetate, allyl isothiocyanate, benzyl isothiocyanate, phenethyl isothiocyanate, 4-(Methylthio)-3-butenyl isothiocyanate and 6-Methylsulfinylhexyl isothiocyanate.

Another group of preferred Nrf2 activators comprises fumaric acid esters, bardoxolone methyl (methyl 2-cyano-3,12-dioxooleana-1,9(11)dien-28-oate, CDDO-Me, RTA 402), ethyl 2-cyano-3,12-dioxooleana-1,9(11)dien-28-oate, 2-cyano-3,12-dioxooleana-1,9(11)dien-28-oic acid (CDDO), 1[2-Cyano-3,12-dioxooleana-1,9(11)-dien-28-oyl]imidazole (CDDO-Im), 2-cyano-N-methyl-3,12-dioxooleana-1,9(11)-dien-28 amide (CDDO-methyl amide, CDDO-MA), [(±)-(4b 5,8aR,10aS)-10a-ethynyl-4b, 8,8-trimethyl-3,7-dioxo-3,4b, 7,8,8a, 9,10,10a-octahydrophenanthrene-2,6-dicarbonitrile] (TBE-31), 2-cyano-3,12-dioxooleana-1,9(11)-dien-28-onitrile (TP-225), 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, alpha lipoic acid and its esters, such as alkyl esters, preferably lipoic acid ethyl ester, curcumin, resveratrol, menadione, cinnamic aldehyde, cinnamic acid esters, caffeic acid esters, cafestol, kahweol, lycopene, carnosol, sulforaphane, oltipraz, capsaicin (8-Methyl-N-vanillyl-trans-6-nonenamide), 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents.

In an even more preferred embodiment of the present invention, the Nrf2 activator is selected from the group of fumaric acid esters, 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-amino salicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents. These preferred aforementioned Nrf2 activators have no or no significant agonistic activity or significant effect on PPAR gamma.

In a further embodiment of the present invention, the Nrf2 activator is auranofin. Auranofin is preferably used according to the invention with a glitazone, more preferably pioglitazone or rosiglitazone.

In a further embodiment of the present invention, the Nrf2 activator is selected from sulfasalazine or 5-aminosalicylic acid (mesalamine). Sulfasalazine or 5-aminosalicylic acid (mesalamine) is preferably used according to the invention with a glitazone, more preferably pioglitazone or rosiglitazone.

It is particularly advantageous that the use of the PPAR gamma agonist and the Nrf2 activator according to the present invention may allow for the maximum dosage of each agent when used in mono-therapy, which result in maximal therapeutic effect. No or only very limited increase in adverse side effects known for the individual PPAR gamma agonist or the Nrf2 activator can be observed. It may also be advantageous to reduce the dose of one or both of the agents employed in the combination treatment of the present invention. Thus, side effects that may be observed in mono-therapy with the agents may be avoided or reduced. Throughout the specification, the term "pharmacologically active derivatives" preferably denotes salts, amides and esters, such as alkylesters, including methyl and ethyl esters, of phamacologically active acids and alkanoic acid esters and ethers of pharmocologically active alcohols, such as acetic acid esters and methyl ethers, as well as alkanoic acid amides of pharmocologically active amines, such as the respective acetic acid amides.

The combination treatment of the present invention can be further combined with treatments and medicaments that are generally used in the various indications as standard treatments. In the treatment of multiple sclerosis, for example, the combination treatment of the present invention can be further combined with interferon, such as interferon beta 1b or interferon beta 1a (Rebif, Avonex) or glatiramer acetate (Copaxone), a sphingosine 1-phosphate receptor modulator, such as Fingolimod (Gilenya) and/or methotrexate. The combination treatment of the present invention can be further combined with RXR specific ligands, such as 9-cis-retinoic acid (RA), in order to obtain even further improved results, particularly in the treatment of psoriasis.

The combination therapy of the present invention can, especially for the treatment of Parkinson's disease, be further combined with established therapeutic agents well-known in the art for the disease, such as levodopa, usually combined with a dopa decarboxylase inhibitor, such as carbidopa or benserazide or a COMT inhibitor, such as entacapone, tolcapone or nitecapone. Moreover, the combination therapy of the present invention can be further combined with dopamine agonists, such as bromocriptine, pergolide, pramipexole, ropinirole, piribedil, cabergoline, apomorphine, lisuride or rotigotine and MAO-B inhibitors, such as selegiline or rasagiline.

The combination therapy according to the present invention may be administered as a simultaneous or sequential regimen, also referred to as co-administration. When administered sequentially, the combination may be administered in two or more administrations. It is also possible to combine any PPAR gamma agonist with an Nrf2 activator in a unitary dosage form for simultaneous or sequential administration to a patient.

In general, for compositions containing fumaric acid esters, an administration twice daily (BID) or thrice daily (TID) is preferred. The dosages of the individual agents are adjusted accordingly.

Co-administration of a PPAR gamma agonist with an Nrf2 activator according to the invention generally and preferably refers to simultaneous or sequential administration of a PPAR gamma agonist and an Nrf2 activator, such that therapeutically effective amounts of the PPAR gamma agonist and the Nrf2 activator are both present at the same time in the body of the patient.

Co-administration includes simultaneous administration and administration of an agent according to the invention before or after administration of the other agent, for example, administration of both agents according to the invention within seconds, minutes, or hours. In one embodiment, the first agent is administered, followed, after a period of hours (e.g., 0.25-12 hours, preferably 0.5 to 3 hours, most preferably 1 to 2 hours), by administration of the second agent.

The combination therapy and co-administration according to the invention frequently provides "synergy" and "synergistic effect", i.e., the therapeutic effect achieved when the PPAR gamma agonist and the Nrf2 activator are used together is more than additive, i.e., greater than the sum of the effects that result from using each agent alone.

An appropriate dose of a PPAR agonist and an Nrf2 activator or pharmaceutical composition comprising a PPAR agonist and an Nrf2 activator for use in the present invention, may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as humans.

In general, a preferred PPAR gamma agonist is administered in combination with a preferred Nrf2 activator according to the invention, preferably orally, in daily dosages of 0.01 mg to 50 mg per kg body weight, dependent on the activity and safety of the respective PPAR gamma agonist. If not indicated otherwise, the dosages given above and below reflect the amount of free base of the PPAR gamma agonist, even if used in form of the maleate or another acid addition salt.

Preferred Nrf2 activators are bardoxolone methyl and dialkyl fumarates such as dimethyl fumarate and diethyl fumarate.

The dialkyl fumarates to be used according to the invention are prepared by processes known in the art (see, for example, EP 0 312 697).

Preferably, the active ingredients, i.e., the agents, are used for preparing oral preparations in the form of tablets, micro-tablets, pellets or granulates, optionally in capsules or sachets. Preparations in the form of micro-tablets or pellets, optionally filled in capsules or sachets, are preferred and are also a subject matter of the invention. According to a preferred embodiment, the size or the mean diameter, respectively, of the pellets or micro-tablets is in the range of 300 to 2,000 μm, especially in the range of 500 to 1,000 μm.

The oral preparations may be provided with an enteric coating. Capsules may be soft or hard gelatine capsules.

The dialkyl fumarates used according to the invention may be used alone or as a mixture of several compounds, optionally in combination with the customary carriers and excipients. The amounts to be used are selected in such a manner that the preparations, such as tablets, obtained contain the active ingredient in an amount corresponding to 10 to 300 mg of fumaric acid per dosage unit.

Preferred preparations according to the invention contain a total amount of 10 to 300 mg of dimethyl fumarate and/or diethyl fumarate.

Fixed-dose combinations of a PPAR agonist and preferably a PPAR gamma agonist with an Nrf2 activator are preferred. Fixed-dose combinations of rosiglitazone with dimethyl fumarate and rosiglitazone with bardoxolone methyl are particularly preferred. Fixed-dose combinations of pioglitazone with dimethyl fumarate and rosiglitazone with bardoxolone methyl are particularly preferred.

In particular, rosiglitazone is preferably administered according to the invention in the form of its maleate in daily dosages of 0.01 to 0.2 mg per kg body weight, more preferably in daily dosages of 0.02 to 0.16 mg per kg body weight and most preferably in daily dosages of 0.025 mg to 0.14 mg per kg body weight, such as in daily dosages of 0.03 mg, 0.06 mg or 0.12 mg per kg body weight. Daily oral dosages of 2 mg, 4 mg and 8 mg rosiglitazone per patient are particularly preferred.

In particular, pioglitazone is preferably administered according to the invention in the form of its hydrochloride in daily dosages of 0.05 to 1 mg per kg body weight, more preferably in daily dosages of 0.1 to 0.8 mg per kg body weight and most preferably in daily dosages of 0.15 mg to 0.7 mg per kg body weight, such as in daily dosages of about 0.2 mg, about 0.4 mg or about 0.6 mg per kg body weight. Daily oral dosages of about 15 mg, about 30 mg and about 45 mg pioglitazone per patient are particularly preferred.

In particular, ciglitazone or troglitazone are preferably administered according to the invention in daily dosages of 1 to 20 mg per kg body weight, more preferably in daily dosages of 2 to 15 mg per kg body weight and most preferably in daily dosages of 3 mg to 10 mg per kg body weight. Oral dosages are particularly preferred.

In general, a preferred Nrf2 activator is administered in combination with a preferred PPAR gamma agonist, preferably orally, in daily dosages of 0.1 mg to 20 mg per kg body weight, dependent on the activity and safety of the respective Nrf2 activator.

In particular, bardoxolone methyl is preferably administered according to the invention in daily dosages of 0.1 to 3 mg per kg body weight, more preferably in daily dosages of 0.2 to 2.5 mg per kg body weight and most preferably in daily dosages of 0.3 mg to 2.2 mg per kg body weight, such as in daily dosages of about 0.35 mg, about 1.1 mg or about 2 mg per kg body weight. Daily oral dosages of about 25 mg, about 75 mg and about 150 mg bardoxolone methyl per patient are particularly preferred.

In particular, dimethyl fumarate is preferably administered according to the invention in daily dosages of 1 to 20 mg per kg body weight, more preferably in daily dosages of 2 to 15 mg per kg body weight and most preferably in daily dosages of 3 mg to 12 mg per kg body weight, such as in daily dosages of about 3.4 mg, about 7 mg or about 10 mg per kg body weight. Daily oral dosages of about 240 mg, about 480 mg and about 720 mg dimethyl fumarate per patient are particularly preferred.

The ratio between the dosages of the PPAR gamma agonist and the Nrf2 activator used in the combinations according to the present invention depends on the activity of the particular PPAR gamma agonist and Nrf2 activator selected.

Daily oral dosages of 2 mg, 4 mg and 8 mg rosiglitazone per patient are particularly preferred.

Daily oral dosages of about 20 mg, about 25 mg, about 75 mg and about 150 mg bardoxolone methyl per patient are particularly preferred. In case bardoxolone methyl is employed in amorphous form, daily dosages of about 20 mg per patient are most preferred.

Daily oral dosages of about 120 mg, about 240 mg, about 360 mg, about 480 mg, about 600 mg and about 720 mg dimethyl fumarate per patient are particularly preferred.

If the Nrf2 activator is dimethyl fumarate, once or twice daily dosing is preferred.

Preferred dosage forms and in particular oral dosage forms such as tablets or capsules may contain:

For daily administration, dosage forms such as tablets or capsules may contain preferably about 2 mg rosiglitazone and about 25 mg bardoxolone methyl or about 2 mg rosiglitazone and about 75 mg bardoxolone methyl or about 2 mg rosiglitazone and about 150 mg bardoxolone methyl or about 4 mg rosiglitazone and about 25 mg bardoxolone methyl or about 4 mg rosiglitazone and about 75 mg bardoxolone methyl or about 4 mg rosiglitazone and about 150 mg bardoxolone methyl or about 8 mg rosiglitazone and about 25 mg bardoxolone methyl or about 8 mg rosiglitazone and about 75 mg bardoxolone methyl or about 8 mg rosiglitazone and about 150 mg bardoxolone methyl. Most preferably, a dosage form may contain about 8 mg rosiglitazone and about 150 mg bardoxolone methyl.

For administration three times daily, preferred dosage forms such as tablets or capsules may contain about 0.7 mg, preferably about 0.67 mg, rosiglitazone and 240 mg dimethyl fumarate or about 1.3 mg, preferably about 1.33 mg, rosiglitazone and about 240 mg dimethyl fumarate or about 2.7 mg, preferably about 2.67 mg, rosiglitazone and about 240 mg dimethyl fumarate or about 0.7 mg, preferably about 0.67 mg, rosiglitazone and 120 mg dimethyl fumarate or about 1.3 mg, preferably about 1.33 mg, rosiglitazone and about 120 mg dimethyl fumarate or about 2.7 mg, preferably about 2.67 mg, rosiglitazone and about 120 mg dimethyl fumarate. Most preferably, a dosage form may contain about 2.7 mg, preferably about 2.67 mg, rosiglitazone and about 240 mg dimethyl fumarate.

For administration two times daily, preferred dosage forms such as tablets or capsules may contain about 1 mg rosiglitazone and about 240 mg dimethyl fumarate or about 2 mg rosiglitazone and about 240 mg dimethyl fumarate or about 4 mg rosiglitazone and about 240 mg dimethyl fumarate.

For daily administration, dosage forms such as tablets or capsules may contain preferably about 15 mg pioglitazone and about 25 mg bardoxolone methyl or about 15 mg pioglitazone and about 75 mg bardoxolone methyl or about 15 mg pioglitazone and about 150 mg bardoxolone methyl or about 30 mg pioglitazone and about 25 mg bardoxolone methyl or about 30 mg pioglitazone and about 75 mg bardoxolone methyl or about 30 mg pioglitazone and about 150 mg bardoxolone methyl or about 45 mg pioglitazone and about 25 mg bardoxolone methyl or about 45 mg pioglitazone and about 75 mg bardoxolone methyl or about 45 mg pioglitazone and about 150 mg bardoxolone methyl. Most preferably, a dosage form may contain about 45 mg pioglitazone and about 150 mg bardoxolone methyl.

For administration three times daily, preferred dosage forms such as tablets or capsules may contain about 5 mg pioglitazone and 240 mg dimethyl fumarate or about 10 mg pioglitazone and about 240 mg dimethyl fumarate or about 15 mg pioglitazone and about 240 mg dimethyl fumarate or about 5 mg pioglitazone and 120 mg dimethyl fumarate or about 10 mg pioglitazone and about 120 mg dimethyl fumarate or about 15 mg pioglitazone and about 120 mg dimethyl fumarate. Most preferably, a dosage form may contain about 15 mg pioglitazone and about 240 mg dimethyl fumarate.

For administration two times daily, preferred dosage forms such as tablets or capsules may contain about 7.5 mg pioglitazone and about 240 mg dimethyl fumarate or about 15 mg pioglitazone and about 240 mg dimethyl fumarate or about 22.5 mg pioglitazone and about 240 mg dimethyl fumarate.

Moreover, pharmaceutical compositions according to the present invention are preferred which comprise as a PPAR gamma agonist about 5 mg, about 7.5 mg, about 10 mg, about 15 mg, about 20 mg, about 22.5 mg or about 25 mg of pioglitazone. Also, pharmaceutical compositions according to the present invention are preferred which comprise as a PPAR gamma agonist about 0.7 mg, about 1 mg, about 1.3 mg, about 2 mg, about 2.7 mg, about 3 mg, about 3.5 mg, about 4 or about 5 mg of rosiglitazone.

Pharmaceutical compositions according to the present invention are preferred which comprise about 120 mg, about 200 mg or about 240 mg of dimethyl fumarate.

In particular, atorvastatin is preferably administered according to the invention in the form of its calcium salt in daily oral dosages of about 10, about 20, about 40 or about 80 mg per patient. Preferably, atorvastatin is combined in the above dosages with dimethyl fumarate in dosages of about 120, about 240, about 360, about 480 or about 720 mg per day. Most preferred are combinations containing about 20 mg or about 40 mg of atorvastatin in the form of its calcium salt, and about 240 mg dimethyl fumarate.

In a further embodiment, atorvastatin is combined in the above dosages with bardoxolone methyl in its amorphous form in dosages of about 20 mg per day. Most preferred are combinations containing about 40 mg or about 80 mg of atorvastatin in the form of its calcium salt, and about 20 mg bardoxolone methyl in its amorphous form.

In particular, losartan is preferably administered according to the invention in daily oral dosages of about 25, about 50, about 75 or about 100 mg per patient. Preferably, losartan is combined in the above dosages with dimethyl fumarate in dosages of about 120, about 240, about 360, about 480 or about 720 mg per day. Most preferred are combinations containing about 25 mg or about 50 mg of losartan, and about 240 mg dimethyl fumarate. The combination is preferably administered twice daily. The combination treatments of sartans and preferably losartan, irbesartan, telmisartan and candesartan with Nrf2 activators such as dimethyl fumarate and bardoxolone methyl are particularly effective for the treatment of diabetic nephropathy (kidney damage due to diabetes) and chronic kidney disease, and also for the treatment of multiple sclerosis.

In a further example, losartan is combined in the above dosages with bardoxolone methyl in its amorphous form in dosages of about 20 mg per day. Most preferred are combinations containing about 25 mg or about 50 mg of losartan, and about 20 mg bardoxolone methyl in its amorphous form. The combination is preferably administered once daily.

In particular, ibuprofen is preferably administered according to the invention in daily dosages that are applicable to monotherapy with ibuprofen, such as about 600 mg, about 800 mg, about 1200 mg or about 2400 mg per patient. Most preferred are combinations containing about 600 mg of ibuprofen and about 240 mg dimethyl fumarate. The combination is preferably administered twice daily.

In a further example, ibuprofen is combined in the above dosages with bardoxolone methyl in its amorphous form in dosages of about 20 mg per day. Most preferred are combinations containing about 800 mg of ibuprofen, and about 20 mg bardoxolone methyl in its amorphous form. The combination is preferably administered once daily.

Preferred ratios between rosiglitazone and dimethyl fumarate are selected from 1/20 to 1/400 (w/w, rosiglitazone/dimethyl fumarate), preferably from 1/25 to 380, more preferably from 1/28 to 1/360. Most preferably the ratios are about 1/30, about 1/45, such as about 1/44.4, about 1/60, about 1/90, such as about 1/88.9 or about 1/92.3, about 1/120, about 1/180, such as 1/171.4 or 1/184.6, about 1/240, or about 1/340, such as about 1/342.9.

Preferred ratios between pioglitazone and dimethyl fumarate are selected from 1/3 to 1/60 (w/w, pioglitazone/dimethyl fumarate), preferably from 1/4 to 1/55, more preferably from 1/5 to 1/52. Most preferably the ratios are about 1/5.3, about 1/8, about 1/10, such as 1/10.7, about 1/12, about 1/16, about 1/24, about 1/32, or about 1 to 48.

In general, ratios between rosiglitazone and bardoxolone methyl are selected from 1/1 to 1/100 (w/w, rosiglitazone/bardoxolone methyl), preferably from 1/1.5 to 1/80, more preferably from 1/2 to 1/75. Most preferably the ratios are about 1/2.5, such as about 1/3.1, about 1/5, such as 1/6.3, about 1/10, such as about 1/9.4 or about 1/12.5, about 1/20, such as 1/18.8, about 1/40, such as about 1/37.5, or about 1/70, such as about 1/75.

In general, ratios between pioglitazone and bardoxolone methyl are selected from 1/0.1 to 1/20 (w/w, pioglitazone/bardoxolone methyl), preferably from 1/0.3 to 1/15, more preferably from 1/0.4 to 1/12. Most preferably the ratios are about 1/0.5, such as about 1/0.4, about 1/0.6, about 1/0.7, or about 1/0.8, about 1/2, such as about 1/1.7 or about 1/2.5, about 1/3, such as about 1/3.3, about 1/5 or about 1/10.

In preferred embodiments of the present invention, amorphic bardoxolone methyl is employed more preferably in a pharmaceutical formulation comprising amorphous bardoxolone methyl, preferably obtained as spray-dried dispersion with a glass-forming excipient, such as methacrylic acid copolymer Type C, USP, e.g., in a 4/6 weight ratio of bardoxolone methyl to methacrylic acid copolymer Type C, USP (Eudragit), more preferably admixed with particles comprised of at least one hydrophilic binder, such as hydroxypropylmethylcellulose, according to US2012/022156. Preferred compositions of bardoxolone methyl according to the present invention also contain a surface active ingredient, such as sodium lauryl sulfate, preferably in amounts of about 1 to 5 weight %, preferably about 3%, such as 2.73%, of the total composition.

In preferred embodiments, amorphous bardoxolone methyl is administered according to the invention in daily dosages of 0.05 to 1 mg per kg body weight, more preferably in dosages of 0.1 to 0.8 mg per kg body weight and most preferably in dosages of 0.2 mg to 0.6 mg per kg body weight, such as in daily dosages of about 0.15 mg, about 0.25 mg or about 0.35 mg per kg body weight. Daily oral dosages of about 10 mg, about 20 mg, and about 30 mg bardoxolone methyl per patient are particularly preferred.

For daily administration of amorphous bardoxolone methyl, the following dosages are employed per patient: about 2 mg rosiglitazone and about 10 mg bardoxolone methyl or about 2 mg rosiglitazone and about 20 mg bardoxolone methyl or about 2 mg rosiglitazone and about 30 mg bardoxolone methyl or about 4 mg rosiglitazone and about 10 mg bardoxolone methyl or about 4 mg rosiglitazone and about 20 mg bardoxolone methyl or about 4 mg rosiglitazone and about 30 mg bardoxolone methyl or about 8 mg rosiglitazone and about 10 mg bardoxolone methyl or about 8 mg rosiglitazone and about 20 mg bardoxolone methyl or about 8 mg rosiglitazone and about 30 mg bardoxolone methyl. Most preferably, about 8 mg rosiglitazone and about 20 mg bardoxolone methyl are employed. In particular it is preferred if the above amounts are used in a fixed dose combination, i.e., in a solid oral dosage form.

Alternatively, for daily administration of amorphous bardoxolone methyl, the following dosages are employed per patient: about 15 mg pioglitazone and about 10 mg bardoxolone methyl or about 15 mg pioglitazone and about 20 mg bardoxolone methyl or about 15 mg pioglitazone and about 30 mg bardoxolone methyl or about 30 mg pioglitazone and about 10 mg bardoxolone methyl or about 30 mg pioglitazone and about 20 mg bardoxolone methyl or about 30 mg pioglitazone and about 30 mg bardoxolone methyl or about 45 mg pioglitazone and about 10 mg bardoxolone methyl or about 45 mg pioglitazone and about 20 mg bardoxolone methyl or about 45 mg pioglitazone and about 30 mg bardoxolone methyl. Most preferably, about 45 mg pioglitazone and about 20 mg bardoxolone methyl are employed. Most preferably, about 8 mg rosiglitazone and about 20 mg bardoxolone methyl are employed. In particular it is preferred if the above amounts are used in a fixed dose combination, i.e., in a solid oral dosage form.

In preferred embodiments of the present invention, where bardoxolone methyl is employed in its amorphous form, preferred ratios between rosiglitazone and bardoxolone methyl are from 1/1 to 1/20 ("/" indicates "to" throughout this application, when a ratio is concerned, w/w, rosiglitazone/bardoxolone methyl), preferably from 1/1.1 to 1/17, more preferably from 1/1.2 to 1/16. Most preferably the ratios are about 1/1.3, such as about 1/1.25, about 1/2.5, about 1/3.5, such as 1/3.75, about 1/5, about 7.5, or about 1/10.

In further preferred embodiments of the present invention, where bardoxolone methyl is employed in its amorphous form, preferred ratios between pioglitazone and bardoxolone methyl are from 1/0.1 to 1/3 (w/w, pioglitazone/bardoxolone methyl), preferably from 1/0.15 to 1/2.5, more preferably from 1/0.2 to 1/2.2. Most preferably the ratios are about 1/0.2, such as about 1/0.22, about 1/0.3, such as about 1/0.33, about 1/0.4, such as about 1/0.44, about 1/0.7, such as about 1/0.67, about 1/1 or about 1/2.

Dosage forms and in particular oral dosage forms such as tablets or capsules containing both a PPAR gamma agonist and an Nrf2 activator in a fixed dose combination comprising the above compositions in the given ratios and especially those containing amorphic bardoxolone methyl are preferred.

Fixed dose combinations, such as tablets containing the active ingredients in the above amounts and ratios, are most preferred.

Pharmaceutical compositions provided by the present disclosure may comprise a therapeutically effective amount of a PPAR gamma agonist and an Nrf2 activator together with a suitable amount of one or more pharmaceutically acceptable vehicles so as to provide a composition for proper administration to a patient. Suitable pharmaceutical vehicles are described in the art.

In certain embodiments, a PPAR gamma agonist and an Nrf2 activator may together be incorporated into pharmaceutical compositions to be administered orally. Oral administration of such pharmaceutical compositions may result in uptake of the PPAR gamma agonist and the Nrf2 activator throughout the intestine and entry into the systemic circulation. Such oral compositions may be prepared in a manner known in the pharmaceutical art and comprise a PPAR gamma agonist and an Nrf2 activator and at least one pharmaceutically acceptable vehicle. Oral pharmaceutical compositions may include a therapeutically effective amount of a PPAR gamma agonist and an Nrf2 activator and a suitable amount of a pharmaceutically acceptable vehicle, so as to provide an appropriate form for administration to a patient.

A PPAR gamma agonist and an Nrf2 activator may together be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

In one embodiment of the present invention, a topical formulation is provided, containing a PPAR agonist, such as a glitazone like pioglitazone or rosiglitazone, and an Nrft2 activator, preferably an Nrf2 activator that does not or only rarely causes an allergic skin reaction, such as bardoxolone methyl, CDDO, CDDO-IM, CDDO-MA, TP-225, menadione, vitamin K1, BHA, BHT, tBHQ, tBQ, curcumin, resveratrol, cinnamic aldehyde or oltipraz. The topical formulation is preferably used in the treatment of psoriasis, acne, rosacea and skin rash such as skin rash caused by EGFR inhibitors like cetuximab, zalutumumab, nimotuzumab, matuzumab, gefitinib, erlotinib, and lapatinib. The formulations are prepared with customary ingredients and processes known in the art and/or disclosed herein.

Pharmaceutical compositions comprising a PPAR gamma agonist and an Nrf2 activator may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of the PPAR gamma agonist and the Nrf2 activator or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsions, tablets, pills, pellets, capsules, capsules containing liquids, powders, sustained-release formulations, suppositories, emulsions, aerosols, sprays, suspensions, or any other form suitable for administration to a patient. Pharmaceutical compositions provided by the present disclosure may be formulated in a unit dosage form. A unit dosage form refers to a physically discrete unit suitable as a unitary dose for patients undergoing treatment, with each unit containing a predetermined quantity of a PPAR gamma agonist and an Nrf2 activator calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a PPAR gamma agonist and an Nrf2 activator may be formulated for immediate release or controlled, sustained or delayed release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of the PPAR gamma agonist and the Nrf2 activator over a period of time as compared to the fluctuations observed with immediate release dosage forms. For some PPAR gamma agonists and Nrf2 activators, maintaining a constant blood and tissue concentration throughout the course of therapy is the most desirable mode of treatment. Immediate release of the PPAR gamma agonist and the Nrf2 activator may cause blood levels to peak above the level required to elicit a desired response, which may waste the agents and may cause or exacerbate toxic side effects. Controlled drug delivery can result in optimal therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of the PPAR gamma agonist and the Nrf2 activator, the stability of these agents in the gastrointestinal tract, the pharmacokinetics thereof and the intended therapeutic profile. An appropriate controlled release oral dosage form may be selected for a particular PPAR gamma agonist and Nrf2 activator. For example, gastric retention oral dosage forms may be appropriate for agents absorbed primarily from the upper gastrointestinal tract, and sustained release oral dosage forms may be appropriate for agents absorbed primarily from the lower gastrointestinal tract.

In certain embodiments, pharmaceutical compositions provided by the present disclosure may be practiced with dosage forms adapted to provide sustained release of a PPAR gamma agonist and an Nrf2 activator upon oral administration. Sustained release oral dosage forms may be used to release the PPAR gamma agonist and/or the Nrf2 activator over a prolonged time period and are useful when it is desired that an agent be delivered to the lower gastrointestinal tract. Sustained release oral dosage forms include any oral dosage form that maintains therapeutic concentrations of the agents in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well-known in the art.

In each of the above dosage forms, the PPAR gamma agonist may be formulated together in admixture or preferably separately from the Nrf2 activator. Each of the PPAR gamma agonist and Nrf2 activator may preferably be contained in separate form within the dosage form, such as an oral dosage form, which is preferably a tablet or capsule. In such oral dosage form, wherein the PPAR gamma agonist and the Nrf2 activator are separated, each agent may be formulated with different excipients. The PPAR gamma agonist and the Nrf2 activator may also each be contained in formulations with different release profiles, i.e., with immediate, controlled or delayed release.

The formulations and in particular the solid oral dosage forms containing a PPAR gamma agonist and/or an Nrf2 activator may contain a conventional additive in the field of pharmaceutical preparation and can be also produced according to a known method. As the additive, for example, an excipient, disintegrant, binder, lubricant, coloring agent, pH regulator, surfactant, release-sustaining agent, stabilizer, sour agent, flavor, glidant and the like can be mentioned. These additives are used in an amount conventionally employed in the field of pharmaceutical preparation.

As the excipient, for example, starches such as corn starch, potato starch, wheat starch, rice starch, partly pregelatinized starch, pregelatinized starch, porous starch and the like; sugars and sugar alcohols such as lactose, fructose, glucose, D-mannitol, sorbitol and the like; anhydrous calcium phosphate, crystalline cellulose, precipitated calcium carbonate, calcium silicate and the like can be mentioned.

As the disintegrant, for example, carboxymethyl cellulose, calcium carboxymethyl cellulose, sodium carboxymethyl starch, croscarmellose sodium, crospovidone, low-substituted hydroxypropyl cellulose, hydroxypropyl starch and the like are used. The amount of the disintegrant to be used is preferably 0.5-25 parts by weight, more preferably 1-15 parts by weight, per 100 parts by weight of the solid preparation.

As the binder, for example, crystalline cellulose, hydroxypropyl cellulose, hydroxypropylmethyl cellulose, polyvinylpyrrolidone, gum arabic powder and the like can be mentioned. The amount of the binder to be used is preferably 0.1-50 parts by weight, more preferably 0.5-40 parts by weight, per 100 parts by weight of the solid preparation.

Preferable examples of the lubricant include magnesium stearate, calcium stearate, talc, sucrose esters of fatty acids, sodium stearyl fumarate and the like. As the coloring agent, for example, food colors such as Food Yellow No. 5, Food Red No. 2, Food Blue No. 2 and the like, food lake colors, ferric oxide and the like can be mentioned. As the pH regulator, citrate, phosphate, carbonate, tartrate, fumarate, acetate, amino acid salt and the like can be mentioned. As the surfactant, sodium lauryl sulfate, polysorbate 80, polyoxyethylene (160) polyoxypropylene (30) glycol and the like can be mentioned.

As the release-sustaining agent, for example, cellulose polymers such as hydroxypropyl cellulose, hydroxypropylmethyl cellulose (preferably hydroxypropylmethyl cellulose 2910, hydroxypropylmethyl cellulose 2208 and the like), cellulose acetate (preferably cellulose acetate having an acetyl content of 39.3-40%), cellulose diacetate, cellulose triacetate, cellulose acetate propionate, ethyl cellulose, sodium carboxymethyl cellulose, crystalline cellulose sodium carboxymethyl cellulose and the like; sodium alginate; carboxyvinyl polymer; acrylic acid polymers such as aminoalkylmethacrylate copolymer RS [Eudragit RS (trademark), Rohm Pharma] and ethyl acrylate-methyl methacrylate copolymer suspension [Eudragit NE (trademark), Rohm Pharma]; and the like can be mentioned. The release-sustaining agent may contain, for example, flux enhancers (e.g., sodium chloride, potassium chloride, sucrose, sorbitol, D-mannitol, polyethylene glycol (preferably polyethylene glycol 400 and the like), propylene glycol, hydroxypropyl cellulose, hydroxypropylmethyl cellulose, hydroxypropylmethyl cellulose phthalate, cellulose acetate phthalate, polyvinyl alcohol, methacrylic acid polymer), plasticizers (e.g., triacetin, acetylated monoglyceride, grape seed oil, olive oil, sesame oil, acetyltributyl citrate, acetyltriethyl citrate, glycerin sorbitol, diethyl oxalate, diethyl maleate, diethyl fumarate, dibutyl succinate, diethyl malonate, dioctyl phthalate, dibutyl sebacate, triethyl citrate, tributyl citrate, glycerol tributyrate) and the like. Preferable examples of the release-sustaining agent include: (1) a semipermeable membrane coating containing cellulose acetate (preferably cellulose acetate having an acetyl content of 39.3-40%), polyethylene glycol (preferably polyethylene glycol 400 or the like) and triacetin; (2) a release-sustaining composition containing sodium carboxymethyl cellulose, hydroxypropylmethyl cellulose 2910, hydroxypropylmethyl cellulose 2208 and microcrystalline cellulose; and the like.

As the stabilizer, for example, tocopherol, tetrasodium edetate, nicotinamide, cyclodextrins and the like can be mentioned. As the sour agent, for example, ascorbic acid, citric acid, tartaric acid, malic acid and the like can be mentioned. As the flavor, for example, menthol, peppermint oil, lemon oil, vanillin and the like can be mentioned. As the glidant, for example, light anhydrous silicic acid, hydrated silicon dioxide and the like can be mentioned. The above-mentioned additives may be used in a mixture of two or more kinds thereof in an appropriate ratio.

Use

An appropriate dose of each PPAR gamma agonist and Nrf2 activator may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

In one embodiment the invention provides a combination of an Nrf2 activator and a PPAR gamma agonist for use in the treatment of inflammatory and autoimmune diseases.

In another embodiment, the invention provides a PPAR gamma agonist for use in combination with a fumaric acid mono- and/or diester, characterized in that the PPAR gamma agonist is selective and has no substantial activity on PPAR alpha or delta.

A therapeutically effective amount of a combination of a PPAR gamma agonist and an Nrf2 activator may be administered as a treatment or preventative measure to a patient having a predisposition for and/or history of immunological, autoimmune, and/or inflammatory diseases including psoriasis, asthma and chronic obstructive pulmonary diseases, cardiac insufficiency including left ventricular insufficiency, myocardial infarction and angina pectoris, mitochondrial and neurodegenerative diseases such as Parkinson's disease, Alzheimer's disease, Huntington's disease, dementia, retinopathia pigmentosa and mitochondrial encephalomyopathy, transplantation rejection, autoimmune diseases including multiple sclerosis, ischemia and reperfusion injury, advanced glycation end-product (AGE)-induced genome and protein damage, inflammatory bowel diseases such as Crohn's disease and ulcerative colitis, thyroid eye disease-related inflammation, fibrosis, such as lung fibrosis, chronic lymphocytic leukemia, aphthous stomatitis, such as recurrent aphthous stomatitis, acute lung injury, non-alcoholic steatohepatitis, acute renal injury and aging-related progressive renal injury, diabetic cardiomyopathy and nephropathy, chronic kidney disease (CKD), atherosclerosis, hypercholesterolemia, hyperlipidemia, aortic stenosis, and acute kidney injury (AKI) after surgery. The present invention can also be used in the prevention of cardiovascular disease, for plaque stabilization, reduction of inflammation, reversal of endothelial dysfunction, and decreased thrombogenicity and wound healing in diabetes. Moreover, the combination treatment of the present invention can be used in the treatment and prevention of atopic dermatitis, dementia, gastritis, fibrosis, insulin resistance, type I and type II diabetes and Syndrome X.

In a preferred embodiment of the present invention the Nrf2 activator is selected from sulfasalazine 2-Hydroxy-5-[4-(2-pyridylsulfamoyl)-phenyldiazenyl]-benzoic acid, 5-[4-(2-Pyridylsulfamoyl)-phenylazo]salicylic acid, mesalamine, and 5-amino-2-hydroxy-benzoic acid 4-(5-thioxo-5H-[1,2]dithiol-3-yl)-phenyl ester hydrochloride (ATB-429). According to the present invention, these Nrf2 activators are preferably combined with a glitazone, such as pioglitazone or rosiglitazone. More preferably, these combinations are preferably used for the treatment of IBS and arthritic diseases.

In a preferred embodiment of the present invention a fumaric acid ester, such as dimethyl fumarate, is combined with a glitazone, such as pioglitazone or rosiglitazone, for the treatment of chronic kidney disease (CKD).

In one embodiment of the present invention, the combination treatment is preferably used in the prophylaxis or treatment of polycystic ovary syndrome (PCOS). It can also be found that compounds that are both PPAR gamma agonists and Nrf2 activators show suitable effects as monotherapeutic agents. Preferred compounds which can be used in the prophylaxis and treatment of PCOS as a single active ingredient in a dosage form such as a tablet are bardoxolone methyl, CDDO, CDDO-IM, CDDO-MA and TP-225. Thus, another object of the present invention is the use of bardoxolone methyl, CDDO, CDDO-IM, CDDO-MA or TP-225 in the prophylaxis and treatment of PCOS and a method of treating PCOS by administration of a pharmacologically effective amount of bardoxolone methyl, CDDO, CDDO-IM, CDDO-MA, TBE-31 or TP-225 or another Nrf2 activator to a patient in need thereof. In many instances, the monotherapy with the aforementioned Nrf2 activators can be further improved with co-administration of a PPAR agonist, such as a glitazone like pioglitazone or rosiglitazone.

NF-κB mediated and/or other diseases are described in the following.

According to another embodiment of the invention, the administration or co-administration of a combination of a PPAR gamma agonist and an Nrf2 activator is effective for treating a member of the group of diseases consisting of a neurological disorder, or an ophthalmological disorder in a mammal, including, without limitation, a human. According to another embodiment the neurological disorder, ophthalmological disorder, or combination thereof results from at least one member of the group consisting of trauma, ischemia, and hypoxia. According to another embodiment the neurological disorder, ophthalmological disorder, or combination thereof is selected from the group consisting of painful neuropathy, neuropathic pain, diabetic neuropathy, drug dependence, drug addiction, drug withdrawal, nicotine withdrawal, opiate tolerance, opiate withdrawal, depression, anxiety, a movement disorder, tardive dyskinesia, a cerebral infection that disrupts the blood-brain barrier, meningitis, meningoencephalitis, stroke, hypoglycemia, cardiac arrest, spinal cord trauma, head trauma, perinatal hypoxia, cardiac arrest, hypoglycemic neuronal damage, glaucoma, retinal ischemia, ischemic optic neuropathy, macular degeneration, multiple sclerosis, sequelae of hyperhomocystinemia, convulsion, pain, schizophrenia, muscle spasm, migraine headache, urinary incontinence, emesis, brain edema, tardive dyskinesia, AIDS-induced dementia, ocular damage, retinopathy, a cognitive disorder, and a neuronal injury associated with HIV infection. According to another embodiment the neurological disorder, ophthalmological disorder, or combination thereof is selected from the group consisting of epilepsy, Alzheimer's disease, vascular (multi-infarct) dementia, Huntington's disease, Parkinsonism, multiple sclerosis, amyotrophic lateral sclerosis, and minimal cognitive impairment (MCI).

Psoriasis is characterized by hyperkeratosis and thickening of the epidermis as well as by increased vascularity and infiltration of inflammatory cells in the dermis. Psoriasis vulgaris manifests as silvery, scaly, erythematous plaques, typically on the scalp, elbows, knees, and buttocks. Guttate psoriasis occurs as teardrop-size lesions. Fumaric acid esters are recognized for the treatment of psoriasis and dimethyl fumarate is approved for the systemic treatment of psoriasis in Germany (Mrowietz and Asadullah, Trends Mol Med 2005, 11(1), 43-48; and Mrowietz et al, Br J Dermatology 1999, 141, 424-429). Efficacy for treating psoriasis can be determined using animal models and in clinical trials. Contrary to fumaric acid esters, it has been found that PPAR gamma agonists are not advantageous in the treatment of psoriasis (Placebo response in two long-term randomized psoriasis studies that are negative for rosiglitazone. Am J Clin Dermatol. 2007; 8(2):93-102). Contrary to this result, it can be found that PPAR gamma agonists provide therapeutic benefit in a combined treatment of psoriasis according to the present invention.

Inflammatory arthritis includes diseases such as rheumatoid arthritis, juvenile rheumatoid arthritis (juvenile idiopathic arthritis), psoriatic arthritis, and ankylosing spondylitis which produce joint inflammation. The pathogenesis of immune-mediated inflammatory diseases including inflammatory arthritis is believed to involve TNF and NK-κB signaling pathways (Tracey et al., Pharmacology & Therapeutics 2008, 117, 244-279). Dimethyl fumarate has been shown to inhibit TNF and inflammatory diseases including inflammatory arthritis which are believed to involve TNF and NK-κB signaling, and may therefore be useful in treating inflammatory arthritis (Lowewe et al., J Immunology 2002, 168, 4781-4787).

Preferably the inventive method of treatment and combinations can be used in the prophylaxis and treatment of neurodegenerative diseases, such as multiple sclerosis, clinically isolated syndrome (CIS) leading to multiple sclerosis, Parkinson's disease, Alzheimer's disease, Huntington's disease, dementia, mitochondrial encephalomyopathy and amyotrophic lateral sclerosis (ALS).

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see, e.g., Wingerchuk, Lab Invest 2001, 81, 263-281; and Virley, NeuroRx 2005, 2(4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, lack of coordination, and visual impairment, which impact the quality of life of the individual. The clinical course of MS can vary from individual to individual, but invariably the disease can be categorized in three forms: relapsing-remitting, secondary progressive, and primary progressive.

Studies support the efficacy of fumaric acid esters for treating MS and they have undergone phase II clinical testing (Schimrigk et al., Eur J Neurology 2006, 13, 604-610; and Wakkee and Thio, Current Opinion Investigational Drugs 2007, 8(11), 955-962). Assessment of MS treatment efficacy in clinical trials can be accomplished using tools such as the Expanded Disability Status Scale and the MS Functional Composite as well as magnetic resonance imaging of lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischemic colitis, diversion colitis, Behcet's colitis, and indeterminate colitis.

Asthma is a reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

As shown in animal studies (Joshi et al., US 2007/0027076), fumaric acid esters may be useful in treating pulmonary diseases such as asthma and chronic obstructive pulmonary disorder.

Chronic obstructive pulmonary disease (COPD), also known as chronic obstructive airway disease, is a group of diseases characterized by the pathological limitation of airflow in the airway that is not fully reversible, and includes conditions such as chronic bronchitis and emphysema, as well as other lung disorders such as asbestosis, pneumoconiosis, and pulmonary neoplasms (see, e.g., Barnes, Pharmacological Reviews 2004, 56(4), 515-548). The airflow limitation is usually progressive and associated with an abnormal inflammatory response of the lungs to noxious particles and gases. COPD is characterized by a shortness of breath that lasts for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

Neurodegenerative diseases such as Parkinson's disease, Alzheimer's disease, Huntington's disease and amyotrophic lateral sclerosis are characterized by progressive dysfunction and neuronal death.

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to smooth muscle movements and coordinate changes in posture as normal, leading to tremor, incoordination, and slowed, reduced movement (bradykinesia) (Blandini, et al., Mol. Neurobiol. 1996, 12, 73-94).

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, i.e., clumps of dead nerve cells containing an abnormal, insoluble protein called amyloid, and neurofibrillary tangles, twisted strands of insoluble proteins in the nerve cell.

Huntington's disease is an autosomal dominant neurodegenerative disorder in which specific cell death occurs in the neostriatum and cortex (Martin, N Engl J Med 1999, 340, 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein huntingtin.

Amyotrophic lateral sclerosis (ALS) is a progressive neurodegenerative disorder characterized by the progressive and specific loss of motor neurons in the brain, brain stem, and spinal cord (Rowland and Schneider, N Engl J Med 2001, 344, 1688-1700). ALS begins with weakness, often in the hands and less frequently in the feet, that generally progresses up an arm or leg. Over time, weakness increases and spasticity develops, characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

Myasthenia gravis (MG) is a classic autoimmune disease affecting neuromuscular junctions of striated muscle. Immunization of different animal species with acetylcholine receptor (AChR) and complete Freund's adjuvant (CFA) results in an animal model of MG named experimental autoimmune myasthenia gravis (EAMG).

Alopecia areata is a common disease, but for ethical reasons it seems difficult to perform large-scale studies to elucidate the pathogenesis and to develop new therapeutic approaches in man. It is therefore helpful to develop appropriate animal models. The Dundee experimental bald rat (DEBR) and the C3H/HeJ mouse are well-established animal models for alopecia areata and can be used for the study of genetic aspects, pathogenesis and therapy of the disease (J Dtsch Dermatol Ges. 2004 April; 2(4):260-73).

A mouse model for diabetic nephropathy can be utilized according to Kidney International 77, 749-750 (May 2010), in order to prove the effect of the combination according to the present invention.

Thus, diseases and conditions for which treatment with the combination of a PPAR gamma agonist and an Nrf2 activator can be useful include rheumatica, granuloma annulare, lupus, autoimmune carditis, eczema, sarcoidosis, and autoimmune diseases including acute disseminated encephalomyelitis, Addison's disease, alopecia areata, ankylosing spondylitis, antiphospholipid antibody syndrome, autoimmune hemolytic anemia, autoimmune hepatitis, autoimmune inner ear disease, bullous pemphigoid, Behcet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barré syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, rheumatoid arthritis, schizophrenia, scleroderma, Sjögren's syndrome, stiff person syndrome, temporal arteritis, ulcerative colitis, vasculitis, vitiligo, and Wegener's granulomatosis.

Administration

The combination of an Nrf2 activator and a PPAR gamma agonist and pharmaceutical compositions thereof may be administered orally or by any other appropriate route, for example, by infusion or bolus injection, by absorption through epithelial or mucocutaneous linings (e.g., oral, rectal, and intestinal mucosa, etc.). Other suitable routes of administration include, but are not limited to intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known (e.g., encapsulation in liposomes, microparticles, microcapsules, capsules, etc.) that may be used to administer a compound and/or pharmaceutical composition.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

The embodiment "PPAR gamma agonist for use in combination with a fumaric acid mono- and/or diester in the treatment of an autoimmune and/or inflammatory disease" relates to a method of use of at least one PPAR gamma agonist in combination with a fumaric acid mono- and/or diester in the treatment of an autoimmune and/or inflammatory disease.

Preferred embodiments of the invention are described below.

1. PPAR gamma agonist for use in combination with a fumaric acid mono- and/or diester in the treatment of an autoimmune and/or inflammatory disease.

2. PPAR gamma agonist, such as rosiglitazone, for use in combination with a fumaric acid mono- and/or diester according to embodiment 1, characterized in that the autoimmune and/or inflammatory disease is psoriasis.

3. PPAR gamma agonist for use in combination with a fumaric acid mono- and/or diester according to one or more of the foregoing embodiments and/or embodiment 1, characterized in that the autoimmune and/or inflammatory disease is selected from the group of psoriatic arthritis, multiple sclerosis, inflammatory bowel disease (IBS), ulcerative colitis, Crohn's disease, hepatitis, effluvium, alopecia areata, cicatricial alopecia, diabetic nephrophathy, CKD and myasthenia gravis.

4. PPAR gamma agonist for use in combination with a fumaric acid mono- and/or diester, according to the aforementioned embodiments, characterized in that the PPAR gamma agonist is selected from the group of rosiglitazone, pioglitazone, troglitazone and ciglitazone.

5. PPAR gamma agonist for use in combination with a fumaric acid mono- and/or diester, according to the aforementioned embodiments, characterized in that the fumaric acid mono- and/or diester is selected from the group of monomethyl hydrogen fumarate, dimethyl fumarate, monoethyl hydrogen fumarate and diethyl fumarate.

6. A pharmaceutical composition comprising a PPAR gamma agonist and a fumaric acid mono- and/or diester and optionally one or more excipients.

7. A pharmaceutical composition comprising rosiglitazone, pioglitazone, troglitazone or ciglitazone and a fumaric acid mono- and/or diester and optionally one or more excipients.

8. A pharmaceutical composition according to one or more of the foregoing embodiments and/or embodiments 6 or 7, characterized in that the fumaric acid mono- and/or diester is selected from the group of monomethyl hydrogen fumarate, dimethyl fumarate, monoethyl hydrogen fumarate, and diethyl fumarate.

9. A solid oral dosage form comprising a PPAR gamma agonist and a fumaric acid mono- and/or diester.

10. A solid oral dosage form comprising rosiglitazone, pioglitazone, troglitazone or ciglitazone as a PPAR gamma agonist and a fumaric acid mono- and/or diester.

11. A solid oral dosage form according to one or more of the foregoing embodiments and/or embodiments 9 or 10, characterized in that the fumaric acid mono- and/or diester is selected from the group of monomethyl hydrogen fumarate, dimethyl fumarate, monoethyl hydrogen fumarate, and diethyl fumarate.

12. A solid oral dosage form according to one or more of the foregoing embodiments and/or embodiments 9 to 10, characterized in that the PPAR gamma agonist and the fumaric acid mono- and/or diester are each contained in the dosage form in a separate composition optionally containing one or more excipients.

13. Kit of parts comprising a) a PPAR gamma agonist, b) a fumaric acid mono- and/or diester and optionally c) instructions for a dosing regimen.

14. Kit of parts comprising a) rosiglitazone, pioglitazone, troglitazone or ciglitazone, b) a fumaric acid mono- and/or diester and optionally c) instructions for a dosing regimen.

15. Kit of parts according to one or more of the foregoing embodiments and/or embodiments 13 or 14, characterized in that the fumaric acid mono- and/or diester is selected from the group of monomethyl hydrogen fumarate, dimethyl fumarate, monoethyl hydrogen fumarate, and diethyl fumarate.

16. PPAR gamma agonist for use in combination with an Nrf2 activator selected from the group of monoalkyl hydrogen fumarate, dialkyl fumarate and bardoxolone alkyl in the treatment of multiple sclerosis.

17. PPAR gamma agonist for use in combination with an Nrf2 activator according to the foregoing embodiments, characterized in that multiple sclerosis includes relapsing-remitting (RR), secondary progressive (SP), primary progressive (PP) and progressive relapsing (PR) multiple sclerosis and the first demyelinating event suggestive of MS or clinically isolated syndrome (CIS).

18. PPAR gamma agonist for use in combination with an Nrf2 activator according to the foregoing embodiments, characterized in that the PPAR gamma agonist is a glitazone.

19. PPAR gamma agonist for use in combination with an Nrf2 activator according to the foregoing embodiments, characterized in that the PPAR gamma agonist is a glitazone selected from the group of pioglitazone and rosiglitazone.

20. PPAR gamma agonist for use in combination with an Nrf2 activator according to the foregoing embodiments, characterized in that Nrf2 activator is selected from the group of monomethyl hydrogen fumarate, dimethyl fumarate and bardoxolone methyl.

21. PPAR gamma agonist for use in combination with an Nrf2 activator according to the foregoing embodiments, characterized in that ratios between rosiglitazone and dimethyl fumarate are selected from 1/20 to 1/400 (w/w, rosiglitazone/dimethyl fumarate).

22. PPAR gamma agonist for use in combination with an Nrf2 activator according to the foregoing embodiments, characterized in that ratios between pioglitazone and dimethyl fumarate are selected from 1/3 to 1/60 (w/w, pioglitazone/dimethyl fumarate).

23. PPAR gamma agonist for use in combination with an Nrf2 activator according to the foregoing embodiments, characterized in that ratios between rosiglitazone and bardoxolone methyl are selected from 1/1 to 1/100 (w/w, rosiglitazone/bardoxolone methyl).

24. PPAR gamma agonist for use in combination with an Nrf2 activator according to the foregoing embodiments, characterized in that bardoxolone methyl is employed in its amorphous form and ratios between rosiglitazone and bardoxolone methyl are from 1/1 to 1/20 (w/w, rosiglitazone/bardoxolone methyl).

25. PPAR gamma agonist for use in combination with an Nrf2 activator according to the foregoing embodiments, characterized in that ratios between pioglitazone and bardoxolone methyl are selected from 1/0.1 to 1/20 (w/w, pioglitazone/bardoxolone methyl).

26. PPAR gamma agonist for use in combination with an Nrf2 activator according to the foregoing embodiments, characterized in that bardoxolone methyl is employed in its amorphous form and ratios between pioglitazone and bardoxolone methyl are from 1/0.1 to 1/3 (w/w, pioglitazone/bardoxolone methyl).

27. A pharmaceutical composition comprising a PPAR gamma agonist and an Nrf2 activator selected from the group of monoalkyl hydrogen fumarate, dialkyl fumarate and bardoxolone alkyl and optionally one or more excipients.

28. A pharmaceutical composition according to one or more of the foregoing embodiments and/or embodiment 27, characterized in that the PPAR gamma agonist is a glitazone.

29. A pharmaceutical composition according to one or more of the foregoing embodiments and/or embodiment 28, characterized in that the glitazone is selected from the group of pioglitazone and rosiglitazone.

30. A pharmaceutical composition according to one or more of the foregoing embodiments and/or embodiments 28 to 30, characterized in that the Nrf2 activator is selected from the group of monomethyl hydrogen fumarate, dimethyl fumarate and bardoxolone methyl.

31. A pharmaceutical composition according to one or more of the foregoing embodiments and/or embodiments 28 to 30, characterized in that ratios between rosiglitazone and dimethyl fumarate are selected from 1/20 to 1/400 (w/w, rosiglitazone/dimethyl fumarate).

32. A pharmaceutical composition according to one or more of the foregoing embodiments and/or embodiments 28 to 30, characterized in that ratios between pioglitazone and dimethyl fumarate are selected from 1/3 to 1/60 (w/w, pioglitazone/dimethyl fumarate).

33. A pharmaceutical composition according to one or more of the foregoing embodiments and/or embodiments 28 to 30, characterized in that ratios between rosiglitazone and bardoxolone methyl are selected from 1/1 to 1/100 (w/w, rosiglitazone/bardoxolone methyl).

34. A pharmaceutical composition according to one or more of the foregoing embodiments and/or embodiments 28 to 30, characterized in that bardoxolone methyl is employed in its amorphous form and ratios between rosiglitazone and bardoxolone methyl are from 1/1 to 1/20 (w/w, rosiglitazone/bardoxolone methyl).

35. A pharmaceutical composition according to one or more of the foregoing embodiments and/or embodiments 28 to 30, characterized in that ratios between pioglitazone and bardoxolone methyl are selected from 1/0.1 to 1/20 (w/w, pioglitazone/bardoxolone methyl).

36. A pharmaceutical composition according to one or more of the foregoing embodiments and/or embodiments 28 to 30, characterized in bardoxolone methyl is employed in its amorphous form and ratios between pioglitazone and bardoxolone methyl are from 1/0.1 to 1/3 (w/w, pioglitazone/bardoxolone methyl).

37. A solid oral dosage form comprising the pharmaceutical composition according to one or more of the foregoing embodiments and/or embodiments 27 to 36.

38. A solid oral dosage form comprising a PPAR gamma agonist and an Nrf2 activator selected from the group of monoalkyl hydrogen fumarate, dialkyl fumarate and bardoxolone alkyl and optionally one or more excipients, wherein the PPAR gamma agonist and the Nrf2 activator are each contained in a separate pharmaceutical formulation.

39. A solid oral dosage form according to one or more of the foregoing embodiments and/or embodiment 38, wherein the PPAR gamma agonist is a glitazone and the Nrf2 activator is selected from the group of monomethyl hydrogen fumarate, dimethyl fumarate and bardoxolone methyl.

40. A solid oral dosage form according to the aforementioned embodiments, wherein the Nrf2 activator is bardoxolone methyl contained in its amorphous form.

41. A solid oral dosage form according to the aforementioned embodiments, wherein the Nrf2 activator is bardoxolone methyl contained in an amorphous dispersion formulation.

42. A solid oral dosage form according to the aforementioned embodiments, wherein the Nrf2 activator is bardoxolone methyl contained in an amorphous dispersion formulation obtained by spray drying or freeze drying.

43. A solid oral dosage form according to the aforementioned embodiments, wherein the Nrf2 activator is bardoxolone methyl contained in an amorphous dispersion formulation with methacrylic acid copolymer Type C, USP.

44. A solid oral dosage form according to the aforementioned embodiments, wherein the Nrf2 activator is bardoxolone methyl contained in an amorphous dispersion formulation with methacrylic acid copolymer Type C, USP in a weight ratio of 4/6.

45. A solid oral dosage form according to the aforementioned embodiments, wherein the Nrf2 activator is bardoxolone methyl contained in an amorphous dispersion formulation comprising at least one hydrophilic binder.

46. A solid oral dosage form according to the aforementioned embodiments, wherein the hydrophilic binder is employed in an amount of between about 1 and about 40% (weight % of the total pharmaceutical composition used for the dosage form), preferably between about 2 and about 20%, more preferably between about 4 and about 10%, even more preferably between about 5 and about 7.5% and most preferred between about 7 and 7.5%, such as about 7%.

47. A solid oral dosage form according to the aforementioned embodiments, wherein the hydrophilic binder is hydroxypropylmethylcellulose.

48. A solid oral dosage form according to the aforementioned embodiments, wherein the Nrf2 activator is bardoxolone methyl contained in an amorphous dispersion formulation and wherein the dosage form also contains a surface active agent, such as sodium lauryl sulfate, preferably in an amount of about 3% of the total weight of the dosage form.

49. Kit of parts comprising a) a PPAR gamma agonist, b) an Nrf2 activator selected from the group of monoalkyl hydrogen fumarate, dialkyl fumarate and bardoxolone alkyl and optionally c) instructions for a dosing regimen.

50. Kit of parts comprising a) a PPAR agonist, b) an Nrf2 activator selected from the group of monoalkyl hydrogen fumarate, dialkyl fumarate and bardoxolone alkyl and optionally c) instructions for a dosing regimen.

51. Kit of parts according to the foregoing embodiments, characterized in that the PPAR gamma agonist is rosiglitazone or pioglitazone.

52. Kit of parts according to the foregoing embodiments, characterized in that the Nrf2 activator is dimethyl fumarate or bardoxolone methyl.

53. PPAR gamma agonist for use in combination with an Nrf2 activator for the treatment of multiple sclerosis according to the foregoing embodiments, wherein said PPAR agonist is administered to a patient simultaneously with or up to 2 days before or after an Nrf2 activator, such as those selected from the group of monoalkyl hydrogen fumarate, dialkyl fumarate and bardoxolone alkyl, is administered to said patient.

54. PPAR gamma agonist for use in combination with an Nrf2 activator for the treatment of multiple sclerosis according to the foregoing embodiments, wherein said PPAR agonist is administered once or twice daily.

55. PPAR gamma agonist for use in combination with an Nrf2 activator for the treatment of multiple sclerosis according to the foregoing embodiments, wherein said Nrf2 activator is administered once or twice daily.

56. PPAR gamma agonist for use in combination with an Nrf2 activator in the treatment of autoimmune and/or inflammatory diseases other than psoriasis.

57. PPAR gamma agonist, preferably other than pioglitazone, for use, in combination with an Nrf2 activator belonging to a different chemical class, in the treatment of autoimmune and/or inflammatory diseases, such as multiple sclerosis, psoriasis or chronic kidney disease.

58. PPAR gamma agonist, preferably other than pioglitazone, for use according to the aforementioned embodiments, wherein the Nrf2 activator has no significant PPAR gamma agonistic effect.

59. PPAR gamma agonist, preferably other than pioglitazone, having no significant activating effect on Nrf2, for use, in combination with an Nrf2 activator having no significant PPAR gamma agonistic effect, in the treatment of autoimmune and/or inflammatory diseases, such as multiple sclerosis, psoriasis or chronic kidney disease.

60. PPAR gamma agonist, preferably other than pioglitazone, for use, in combination with an Nrf2 activator belonging to a different chemical class, wherein the Nrf2 activator is other than bardoxolone methyl and its derivatives, in the treatment of autoimmune and/or inflammatory diseases, such as multiple sclerosis, psoriasis or chronic kidney disease.

61. Composition comprising a PPAR gamma agonist and an Nrf2 activator belonging to a different chemical class, for use in the treatment of autoimmune and/or inflammatory diseases, such as multiple sclerosis, psoriasis or chronic kidney disease.

62. Composition according to the aforementioned embodiment, comprising a PPAR gamma agonist having no significant activating effect on Nrf2 and an Nrf2 activator having no significant PPAR gamma agonistic effect, for use in the treatment of autoimmune and/or inflammatory diseases, such as multiple sclerosis, psoriasis or chronic kidney disease.

63. Composition comprising a PPAR gamma agonist, such as pioglitazone, and an Nrf2 activator.

64. Composition comprising a PPAR gamma agonist, such as pioglitazone, and an Nrf2 activator having no significant PPAR gamma agonistic effect.

65. Composition comprising pioglitazone and an Nrf2 activator having no significant PPAR gamma agonistic effect, for use in the treatment of psoriasis and other autoimmune and/or inflammatory diseases, such as multiple sclerosis, psoriasis or chronic kidney disease.

66. PPAR gamma agonist for use, in combination with an Nrf2 activator having no significant PPAR gamma agonistic effect, in the treatment of multiple sclerosis.

67. PPAR gamma agonist for use, in combination with an Nrf2 activator other than bardoxolone methyl, in the treatment of chronic kidney disease (CKD) or multiple sclerosis.

68. PPAR gamma agonist for use in combination with an Nrf2 activator according to the foregoing embodiments, characterized in that multiple sclerosis includes relapsing-remitting (RR), secondary progressive (SP), primary progressive (PP) and progressive relapsing (PR) multiple sclerosis and the first demyelinating event suggestive of MS or clinically isolated syndrome (CIS).

69. PPAR gamma agonist for use in combination with an Nrf2 activator according to the foregoing embodiments, characterized in that the PPAR gamma agonist is a glitazone.

70. PPAR gamma agonist for use in combination with an Nrf2 activator according to any of the foregoing embodiments, characterized in that the PPAR gamma agonist is a glitazone selected from the group of pioglitazone and rosiglitazone.

71. PPAR gamma agonist for use in combination with an Nrf2 activator according to any of the foregoing embodiments, characterized in that the Nrf2 activator is selected from the chemical compounds belonging to the group of Michael reaction acceptors, phenols, diphenols, chalcones, isothiocyanates, thiocarbamates, quinones, naphthoquinones and 1,2-dithiole-3-thiones, wherein one or more, preferably 1, 2, 3, 4, 5, 6 or 7, H-atoms may be substituted by linear or branched alkyl and perfluoroalkyl such as methyl, ethyl, trifluoromethyl, halogen such as Br, Cl, F or I, hydroxy, alkoxy and perfluoroalkoxy such as methoxy, ethoxy, trifluoromethoxy, cyano and nitro, which chemical compounds have no more than one or two 5- or 6-membered carbocyclic rings or 5- or 6-membered heterocyclic rings having 1, 2 or 3 N-, O- or S-atoms as ring atoms, which rings may be fused to each other, or preferably no or only one carbocyclic or heterocyclic ring. Compositions containing these Nrf2 activators are preferred.

Preferred Nrf2 activators for use in combinations according to the invention, and particularly according to embodiment 71 above, are chemical compounds containing less than 35, preferably less than 30, more preferably less than 25, most preferably less than 20, even less than 15 or less than 10 carbon atoms and/or having a molecular weight of less than 400, preferably less than 300, most preferably less than 200 g/mol or less than 170 g/mol and/or having no significant PPAR gamma agonistic activity. Compositions containing these Nrf2 activators are preferred.

72. PPAR gamma agonist for use in combination with an Nrf2 activator and compositions according to any of the foregoing embodiments, characterized in that the Nrf2 activator is selected from 2-naphthoquinone, cinnamic aldehyde, caffeic acid and its esters, curcumin, resveratrol, artesunate, tert-butylhydroquinone, vitamins K1, K2 and K3 and the respective quinone or hydroquinone forms of the aforementioned quinone and hydroquinone derivatives, fumaric acid esters, i.e., fumaric acid mono- and/or diester preferably selected from the group of monoalkyl hydrogen fumarate and dialkyl fumarate, such as monomethyl hydrogen fumarate, dimethyl fumarate, monoethyl hydrogen fumarate, and diethyl fumarate, isothiocyanate such as sulforaphane, 1,2-dithiole-3-thione such as oltipraz, 3,5-di-tert-butyl-4-hydroxytoluene, 3-hydroxycoumarin, 4-hydroxynonenal, 4-oxononenal, malondialdehyde, (E)-2-hexenal, capsaicin, allicin, allylisothiocyanate, 6-methylthiohexyl isothiocyanate, 7-methylthioheptyl isothiocyanate, sulforaphane, 8-methylthiooctyl isothiocyanate, 8-iso prostaglandin A2, alkyl pyruvate, such as methyl and ethyl pyruvate, diethyl or dimethyl oxalopropionate, 2-acetamidoacrylate, and methyl or ethyl-2-acetamidoacrylate, and a pharmacologically active stereoisomer or derivative of the aforementioned agents.

73. PPAR gamma agonist for use in combination with an Nrf2 activator and compositions according to any the foregoing embodiments, characterized in that the nrf2 activator is selected from monomethyl hydrogen fumarate, dimethyl fumarate, oltipraz, 1,2-naphthoquinone, tert-butylhydroquinone, methyl or ethyl pyruvate, 3,5-di-tert-butyl-4-hydroxytoluene, diethyl and dimethyl oxalopropionate.

74. Kit of parts comprising: a) a PPAR gamma agonist other than pioglitazone, b) an Nrf2 activator selected from the group of monoalkyl hydrogen fumarate, dialkyl fumarate and bardoxolone alkyl and optionally c) instructions for a dosing regimen.

75. Kit of parts comprising: a) a PPAR gamma agonist having no significant activating effect on Nrf2, b) an Nrf2 activator selected from the group of monoalkyl hydrogen fumarate, dialkyl fumarate and bardoxolone and optionally c) instructions for a dosing regimen.

76. Kit of parts comprising: a) a PPAR gamma agonist having no significant activating effect on Nrf2, b) an Nrf2 activator having no significant PPAR gamma agonistic effect and optionally c) instructions for a dosing regimen.

77. Kit of parts comprising: a) a PPAR gamma agonist having no significant activating effect on Nrf2, b) an Nrf2 activator selected from the chemical compounds belonging to the group of Michael reaction acceptors, phenols, diphenols, chalcones, isothiocyanates, thiocarbamates, quinones, naphthoquinones and 1,2-dithiole-3-thiones, wherein one or more, preferably 1, 2, 3, 4, 5, 6 or 7, H-atoms may be substituted by linear or branched alkyl and perfluoroalkyl such as methyl, ethyl, trifluoromethyl, halogen such as Br, Cl, F or I, hydroxy, alkoxy or perfluoroalkoxy such as methoxy, ethoxy, trifluoromethoxy, cyano and nitro, which chemical compounds have no more than one or two 5- or 6-membered carbocyclic rings or 5- or 6-membered heterocyclic rings having 1, 2 or 3 N-, O- or S-atoms as ring atoms, which rings may be fused to each other, or preferably no or only one carbocyclic or heterocyclic ring and optionally c) instructions for a dosing regimen.

78. Composition comprising: a) a PPAR gamma agonist, preferably other than pioglitazone and b) an Nrf2 activator selected from the group of monoalkyl hydrogen fumarate, dialkyl fumarate and bardoxolone alkyl.

79. Composition comprising: a) a PPAR gamma agonist having no significant activating effect on Nrf2 and b) an Nrf2 activator selected from the group of monoalkyl hydrogen fumarate, dialkyl fumarate and bardoxolone.

80. Composition comprising: a) a PPAR gamma agonist having no significant activating effect on Nrf2 and b) an Nrf2 activator having no significant PPAR gamma agonistic effect.

81. Composition comprising: a) a PPAR gamma agonist having no significant activating effect on Nrf2 and b) an Nrf2 activator selected from the chemical compounds belonging to the group of Michael reaction acceptors, phenols, diphenols, chalcones, isothiocyanates, thiocarbamates, quinones, naphthoquinones and 1,2-dithiole-3-thiones, wherein one or more, preferably 1, 2, 3, 4, 5, 6 or 7, H-atoms may be substituted by linear or branched alkyl and perfluoroalkyl such as methyl, ethyl, trifluoromethyl, halogen such as Br, Cl, F or I, hydroxy, alkoxy and perfluoroalkoxy such as methoxy, ethoxy, trifluoromethoxy, cyano and nitro, which chemical compounds have no more than one or two 5- or 6-membered carbocyclic rings or 5- or 6-membered heterocyclic rings having 1, 2 or 3 N-, O- or S-atoms as ring atoms, which rings may be fused to each other, or preferably no or only one carbocyclic or heterocyclic ring.

82. Method of treating or preventing cancer, preferably hematological cancer, such as leukemia, such as acute myeloid leukaemia (AML), comprising administration of a PPAR gamma agonist and an Nrf2 activator to a patient in need thereof, wherein said Nrf2 activator is capable of provoking or inducing a stimulated and/or increased nuclear translocation of Nrf2 protein and is:

a) selected from the group of Michael reaction acceptors, phenols, diphenols, chalcones, isothiocyanates, thiocarbamates, quinones, naphthoquinones and 1,2-dithiole-3-thiones; and b) contains less than 35 carbon atoms; and/or c) has a molecular weight of less than 600 g/mol; and/or d) contains no or not more than one or two fused or monocyclic 5- or 6-membered carbocyclic or heterocyclic rings having 1, 2 or 3 ring atoms selected from N, O or S.

In one embodiment of the foregoing method, the Nrf2 activator is preferably other than arsenic trioxide. Preferably, the Nrf2 activator is dimethyl fumarate, monomethyl hydrogen fumarate or bardoloxolone methyl.

83. Method of treating or preventing diabetes, such as type II diabetes, and its complications, such as arthritis, chronic kidney disease and syndrome X, comprising administration of a PPAR gamma agonist and an Nrf2 activator to a patient in need thereof, wherein said Nrf2 activator is capable of provoking or inducing a stimulated and/or increased nuclear translocation of Nrf2 protein and is:

a) selected from the group of Michael reaction acceptors, phenols, diphenols, chalcones, isothiocyanates, thiocarbamates, quinones, naphthoquinones and 1,2-dithiole-3-thiones; and b) contains less than 35 carbon atoms; and/or c) has a molecular weight of less than 600 g/mol; and/or d) contains no or not more than one or two fused or monocyclic 5- or 6-membered carbocyclic or heterocyclic rings having 1, 2 or 3 ring atoms selected from N, O or S.

In one embodiment of the foregoing method, the Nrf2 activator is preferably other than bardoxolone methyl and/or a corticosteroid. Preferably, the Nrf2 activator is dimethyl fumarate or monomethyl hydrogen fumarate.

84. Method of treating or preventing cardiovascular diseases, comprising administration of a PPAR gamma agonist and an Nrf2 activator to a patient in need thereof, wherein said Nrf2 activator is capable of provoking or inducing a stimulated and/or increased nuclear translocation of Nrf2 protein and is:

a) selected from the group of Michael reaction acceptors, phenols, diphenols, chalcones, isothiocyanates, thiocarbamates, quinones, naphthoquinones and 1,2-dithiole-3-thiones; and b) contains less than 35 carbon atoms; and/or c) has a molecular weight of less than 600 g/mol; and/or d) contains no or not more than one or two fused or monocyclic 5- or 6-membered carbocyclic or heterocyclic rings having 1, 2 or 3 ring atoms selected from N, O or S.

85. Method of treating or preventing respiratory diseases, such as asthma, chronic obstructive pulmonary disorder and fibrosis, comprising administration of a PPAR gamma agonist and an Nrf2 activator to a patient in need thereof, wherein said Nrf2 activator is capable of provoking or inducing a stimulated and/or increased nuclear translocation of Nrf2 protein and is:

a) selected from the group of Michael reaction acceptors, phenols, diphenols, chalcones, isothiocyanates, thiocarbamates, quinones, naphthoquinones and 1,2-dithiole-3-thiones; and b) contains less than 35 carbon atoms; and/or c) has a molecular weight of less than 600 g/mol; and/or d) contains no or not more than one or two fused or monocyclic 5- or 6-membered carbocyclic or heterocyclic rings having 1, 2 or 3 ring atoms selected from N, O or S.

In one embodiment of the foregoing method, the Nrf2 activator is preferably other than a corticosteroid. Preferably, the Nrf2 activator is dimethyl fumarate, monomethyl hydrogen fumarate or bardoloxolone methyl.

86. Method of treating or preventing graft rejection and/or necrosis, comprising administration of a PPAR gamma agonist and an Nrf2 activator to a patient in need thereof, wherein said Nrf2 activator is capable of provoking or inducing a stimulated and/or increased nuclear translocation of Nrf2 protein and is:

a) selected from the group of Michael reaction acceptors, phenols, diphenols, chalcones, isothiocyanates, thiocarbamates, quinones, naphthoquinones and 1,2-dithiole-3-thiones; and b) contains less than 35 carbon atoms; and/or c) has a molecular weight of less than 600 g/mol; and/or d) contains no or not more than one or two fused or monocyclic 5- or 6-membered carbocyclic or heterocyclic rings, having 1, 2 or 3 ring atoms selected from N, O or S.

87. Method of treating or preventing psoriasis, comprising administration of a PPAR agonist and an Nrf2 activator to a patient in need thereof, wherein said Nrf2 activator is capable of provoking or inducing a stimulated and/or increased nuclear translocation of Nrf2 protein and is:

a) selected from the group of Michael reaction acceptors, phenols, diphenols, chalcones, isothiocyanates, thiocarbamates, quinones, naphthoquinones and 1,2-dithiole-3-thiones; and b) contains less than 35 carbon atoms; and/or c) has a molecular weight of less than 600 g/mol; and/or d) contains no or not more than one or two fused or monocyclic 5- or 6-membered carbocyclic or heterocyclic rings having 1, 2 or 3 ring atoms selected from N, O or S.

In one embodiment of the foregoing method, no therapeutic amounts of hydroxyurea are co-administered to the patient. In another embodiment of the foregoing method, no therapeutic amounts of monomethyl hydrogen fumarate are co-administered to the patient. In another embodiment of the foregoing method, no therapeutic amounts of dimethyl fumarate are co-administered to the patient. In another embodiment of the foregoing method, the Nrf2 activator is bardoloxolone methyl. In another embodiment of the foregoing method, the PPAR agonist is other than pioglitazone, such as rosiglitazone.

88. Method of treating or preventing autoimmune and/or inflammatory diseases other than psoriasis, comprising administration of a PPAR agonist and dialkyl fumarate and/or monoalkyl hydrogen fumarate to a patient in need thereof.

89. Method of treating or preventing autoimmune and/or inflammatory diseases other than chronic kidney disease, comprising administration of a PPAR agonist and bardoxolone methyl to a patient in need thereof.

90. Method of treating or preventing cardiovascular diseases, respiratory disorders, graft rejection, cancer and diabetes and its complications, comprising administration of a PPAR agonist and dimethyl fumarate and/or monomethyl hydrogen fumarate to a patient in need thereof.

91. Method of treating or preventing autoimmune/inflammatory and cardiovascular diseases, respiratory disorders, graft rejection, cancer and diabetes and its complications, comprising administration of a PPAR agonist other than pioglitazone and dimethyl fumarate and/or monomethyl hydrogen fumarate to a patient in need thereof.

92. PPAR gamma agonist for use in combination with an Nrf2 activator in the treatment of an autoimmune and/or inflammatory disease.

93. PPAR gamma agonist for use in combination with an Nrf2 activator according to one or more of the foregoing embodiments and/or embodiment 92, characterized in that the Nrf2 activator is dimethyl fumarate.

94. PPAR gamma agonist for use in combination with an Nrf2 activator according to one or more of the foregoing embodiments and/or embodiment 92, characterized in that the Nrf2 activator is bardoxolone methyl.

95. PPAR gamma agonist for use in combination with an Nrf2 activator according to one of the foregoing embodiments, characterized in that the PPAR gamma agonist is pioglitazone.

96. PPAR gamma agonist for use in combination with an Nrf2 activator according to one of the foregoing embodiments, characterized in that the PPAR gamma agonist is selected from the group of rosiglitazone, troglitazone and ciglitazone.

97. PPAR gamma agonist for use in combination with an Nrf2 activator according to one of the foregoing embodiments, characterized in that the autoimmune and/or inflammatory disease is psoriasis.

98. PPAR gamma agonist for use in combination with an Nrf2 activator according to one of the foregoing embodiments, characterized in that the autoimmune and/or inflammatory disease is multiple sclerosis.

99. PPAR gamma agonist for use in combination with an Nrf2 activator according to one of the foregoing embodiments, characterized in that the autoimmune and/or inflammatory disease is ulcerative colitis.

100. PPAR gamma agonist for use in combination with an Nrf2 activator according to one of the foregoing embodiments, characterized in that the autoimmune and/or inflammatory disease is Crohn's disease.

101. PPAR gamma agonist for use in combination with an Nrf2 activator according to one of the foregoing embodiments, characterized in that the autoimmune and/or inflammatory disease is allopecia areata or cicatricial alopecia.

102. PPAR gamma agonist for use in combination with an Nrf2 activator according to one of the foregoing embodiments, characterized in that the autoimmune and/or inflammatory disease is diabetic nephropathy.

103. PPAR gamma agonist for use in combination with an Nrf2 activator according to one of the foregoing embodiments, characterized in that the autoimmune and/or inflammatory disease is myasthenia gravis.

104. A pharmaceutical composition comprising pioglitazone, dimethyl fumarate and optionally one or more excipients.

105. A pharmaceutical composition comprising dimethyl fumarate, a PPAR gamma agonist selected from rosiglitazone, troglitazone and ciglitazone, and optionally one or more excipients.

106. A pharmaceutical composition comprising bardoxolone methyl, a PPAR gamma agonist selected from pioglitazone, rosiglitazone, troglitazone and ciglitazone, and optionally one or more excipients.

107. Method of treating or preventing neurodegenerative diseases, comprising administration of a PPAR gamma agonist selected from the group of glitazones and a fumaric acid monoalkyl and/or dialkyl ester to a patient in need thereof.

108. Method according to one or more of the foregoing embodiments and/or embodiment 107, wherein the fumaric acid dialkyl ester is selected from dimethyl fumarate and diethyl fumarate and the fumaric acid monoalkyl ester is selected from monomethyl hydrogen fumarate and monoethyl hydrogen fumarate.

109. Method according to one or more of the foregoing embodiments and/or embodiment 107 or 108, wherein the PPAR gamma agonist glitazone is selected from pioglitazone and rosiglitazone.

110. Method according to one or more of the foregoing embodiments and/or embodiment 107, 108 or 109, wherein the neurodegenerative disease is multiple sclerosis.

111. A pharmaceutical composition comprising a PPAR gamma agonist selected from the group of glitazones, a fumaric acid monoalkyl and/or dialkyl ester and optionally one or more excipients.

112. A pharmaceutical composition according to one or more of the foregoing embodiments and/or embodiment 111, wherein the fumaric acid dialkyl ester is selected from dimethyl fumarate and diethyl fumarate and the fumaric acid monoalkyl ester is selected from monomethyl hydrogen fumarate and monoethyl hydrogen fumarate.

113. A pharmaceutical composition according to one or more of the foregoing embodiments and/or embodiment 111 or 112, wherein the PPAR gamma agonist glitazone is selected from pioglitazone and rosiglitazone.

114. Method of treating or preventing neurodegenerative diseases, comprising administration of a pharmaceutical composition according to one or more of the foregoing embodiments and/or embodiments 111, 112 or 113 to a patient in need thereof.

115. Method according to one or more of the foregoing embodiments and/or embodiment 114, wherein the neurodegenerative disease is multiple sclerosis.

116. A solid oral dosage form comprising a PPAR gamma agonist selected from the group of glitazones, a fumaric acid monoalkyl and/or dialkyl ester and optionally one or more excipients.

117. A solid oral dosage form according to one or more of the foregoing embodiments and/or embodiment 116, wherein the fumaric acid dialkyl ester is selected from dimethyl fumarate and diethyl fumarate and the fumaric acid monoalkyl ester is selected from monomethyl hydrogen fumarate and monoethyl hydrogen fumarate.

118. A solid oral dosage form according to one or more of the foregoing embodiments and/or embodiment 116 or 117, wherein the PPAR gamma agonist glitazone is selected from pioglitazone and rosiglitazone.

119. Method of treating or preventing neurodegenerative diseases, comprising oral administration of a solid oral dosage form according to one or more of the foregoing embodiments and/or embodiments 116, 117 or 118 to a patient in need thereof.

120. Method according to one or more of the foregoing embodiments and/or embodiment 119, wherein the neurodegenerative disease is multiple sclerosis.

121. Kit of parts comprising: a) a PPAR gamma agonist selected from the group of glitazones, b) a fumaric acid monoalkyl and/or dialkyl ester and optionally c) instructions for a dosage regimen.

122. Kit of parts according to one or more of the foregoing embodiments and/or embodiment 121, wherein the fumaric acid dialkyl ester is selected from dimethyl fumarate and diethyl fumarate and the fumaric acid monoalkyl ester is selected from monomethyl hydrogen fumarate and monoethyl hydrogen fumarate.

123. Kit of parts according to one or more of the foregoing embodiments and/or embodiment 121 or 122, wherein the PPAR gamma agonist glitazone is selected from pioglitazone and rosiglitazone.

124. A method of treatment of an autoimmune and/or inflammatory disorder comprising administration of a combination of a PPAR gamma agonist selected from the group of glitazones and a) an isolated Nrf2 activator selected from the group of fumaric acid esters, bardoxolone methyl (methyl 2-cyano-3,12-dioxooleana-1,9(11)dien-28-oate, CDDO-Me, RTA 402), ethyl 2-cyano-3,12-dioxooleana-1,9 (11)dien-28-oate, 2-cyano-3,12-dioxooleana-1,9(11)dien-28-oic acid (CDDO), 1[2-Cyano-3,12-dioxooleana-1,9(11)-dien-28-oyl]imidazole (CDDO-Im), 2-cyano-N-methyl-3,12-dioxooleana-1,9(11)-dien-28 amide (CDDO-methyl amide, CDDO-MA), [(±)-(4bS,8aR,10aS)-10a-ethynyl-4b,8,8-trimethyl-3,7-dioxo-3,4b,7,8,8a,9,10,10a-octahydrophenanthrene-2,6-dicarbonitrile](TBE-31), 2-cyano-3,12-dioxooleana-1,9(11)-dien-28-onitrile (TP-225), 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, or b) a pharmaceutical composition comprising said isolated Nrf2 activator, provided that if the autoimmune and/or inflammatory disorder is psoriasis, the PPAR agonist is pioglitazone and the Nrf2 activator is a fumaric acid ester, the treatment is not combined with hydroxyurea.

125. A method of treatment of an autoimmune and/or inflammatory disorder comprising administration of a combination of a PPAR gamma agonist selected from the group of glitazones and a) an isolated Nrf2 activator selected from the group of fumaric acid esters, 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, or b) a pharmaceutical composition comprising said isolated Nrf2 activator, provided that if the autoimmune and/or inflammatory disorder is psoriasis, the PPAR agonist is pioglitazone and the Nrf2 activator is a fumaric acid ester, the treatment is not combined with hydroxyurea.

126. A method of treatment according to the aforementioned embodiments, wherein the autoimmune and/or inflammatory disorder is selected from psoriasis, scleroderma, chronic kidney disease (CKD), neurodegenerative diseases, asthma, chronic obstructive pulmonary disorder (COPD), fibrosis, inflammatory arthritis disease and inflammatory bowel disease (IBD).

127. A method of treatment according to the aforementioned embodiment, wherein the autoimmune and/or inflammatory disorder is a neurodegenerative disease selected from multiple sclerosis, clinically isolated syndrome (CIS), amyotrophic lateral sclerosis, Alzheimer's disease, Huntington's disease, and Parkinson's disease.

128. A method for the reduction of inflammation in a patient, comprising administration of a combination of a PPAR gamma agonist selected from the group of glitazones and a) an isolated Nrf2 activator selected from the group of fumaric acid esters, bardoxolone methyl (methyl 2-cyano-3,12-dioxooleana-1,9(11)dien-28-oate, CDDO-Me, RTA 402), ethyl 2-cyano-3,12-dioxooleana-1,9(11)dien-28-oate, 2-cyano-3,12-dioxooleana-1,9(11)dien-28-oic acid (CDDO), 1 [2-Cyano-3,12-dioxooleana-1,9(11)-dien-28-oyl]imidazole (CDDO-Im), 2-cyano-N-methyl-3,12-dioxooleana-1,9(11)-dien-28 amide (CDDO-methyl amide, CDDO-MA), [(±)-(4bS,8aR,10aS)-10a-ethynyl-4b,8,8-trimethyl-3,7-dioxo-3,4b,7,8,8a,9,10,10a-octahydrophenanthrene-2,6-dicarbonitrile] (TBE-31), 2-cyano-3,12-dioxooleana-1,9(11)-dien-28-onitrile (TP-225), 3-tert-butyl-4- hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, or b) a pharmaceutical composition comprising said isolated Nrf2 activator, provided that if the inflammation is occurring with and/or is resulting from psoriasis, the PPAR agonist is pioglitazone and the Nrf2 activator is a fumaric acid ester, the treatment is not combined with hydroxyurea.

129. A method for the reduction of inflammation in a patient, comprising administration of a combination of a PPAR gamma agonist selected from the group of glitazones and a) an isolated Nrf2 activator selected from the group of fumaric acid esters, 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, or b) a pharmaceutical composition comprising said isolated Nrf2 activator, provided that if the inflammation is occurring with and/or is resulting from psoriasis, the PPAR agonist is pioglitazone and the Nrf2 activator is a fumaric acid ester, the treatment is not combined with hydroxyurea.

130. A method according to the aforementioned embodiments, wherein the inflammation is a chronic inflammation.

131. A method according to the aforementioned embodiments, wherein the PPAR gamma agonist glitazone is selected from pioglitazone and rosiglitazone.

132. A method according to the aforementioned embodiments, wherein the Nrf2 activator is a fumaric acid ester selected from dialkyl fumarate and monoalkyl fumarate.

133. A method according to the aforementioned embodiment, wherein the Nrf2 activator is dimethyl fumarate.

134. A pharmaceutical composition comprising a PPAR gamma agonist selected from the group of glitazones and an Nrf2 activator selected from the group of fumaric acid esters, bardoxolone methyl (methyl 2-cyano-3,12-dioxooleana-1,9(11)dien-28-oate, CDDO-Me, RTA 402), ethyl 2-cyano-3,12-dioxooleana-1,9(11)dien-28-oate, 2-cyano-3,12-dioxooleana-1,9(11)dien-28-oic acid (CDDO), 1 [2-Cyano-3,12-dioxooleana-1,9(11)-dien-28-oyl]imidazole (CDDO-Im), 2-cyano-N-methyl-3,12-dioxooleana-1,9(11)-dien-28 amide (CDDO-methyl amide, CDDO-MA), [(±)-(4bS,8aR,10aS)-10a-ethynyl-4b,8,8-trimethyl-3,7-dioxo-3,4b,7,8,8a,9,10,10a-octahydrophenanthrene-2,6-dicarbonitrile] (TBE-31), 2-cyano-3,12-dioxooleana-1,9(11)-dien-28-onitrile (TP-225), 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenylester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, and optionally one or more excipients.

135. A pharmaceutical composition comprising a PPAR gamma agonist selected from the group of glitazones and an Nrf2 activator selected from the group of fumaric acid esters, 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butyl quinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, and optionally one or more excipients.

136. A pharmaceutical composition according to the aforementioned embodiments, wherein the PPAR gamma agonist glitazone is selected from pioglitazone and rosiglitazone.

137. A pharmaceutical composition according to the aforementioned embodiments, wherein the Nrf2 activator is a fumaric acid ester selected from dialkyl fumarate and monoalkyl fumarate.

138. A pharmaceutical composition according to the aforementioned embodiment, wherein the Nrf2 activator is dimethyl fumarate.

139. A solid oral dosage form comprising the pharmaceutical composition according to the aforementioned embodiments.

140. A method of treatment of an autoimmune and/or inflammatory disorder comprising administration of a pharmaceutical composition according to one or more of the foregoing embodiments and/or embodiments 134, 135, 136, 137 or 138.

141. A method of treatment according to the aforementioned embodiment, wherein the autoimmune and/or inflammatory disorder is selected from psoriasis, scleroderma, chronic kidney disease (CKD), neurodegenerative diseases, asthma, chronic obstructive pulmonary disorder (COPD), fibrosis, inflammatory arthritis and inflammatory bowel disease (IBD).

142. A method of treatment according to the aforementioned embodiment, wherein the autoimmune and/or inflammatory disorder is a neurodegenerative disease selected from multiple sclerosis, clinically isolated syndrome (CIS), amyotrophic lateral sclerosis, Alzheimer's disease, Huntington's disease, and Parkinson's disease.

143. A method for the reduction of inflammation in a patient, comprising administration of a pharmaceutical composition according to one or more of the foregoing embodiments and/or embodiments 134, 135, 136, 137 or 138.

144. A method according to the aforementioned embodiment, wherein the inflammation is a chronic inflammation.

145. A kit of parts comprising: a) a PPAR gamma agonist selected from the group of glitazones, b) an Nrf2 activator selected from the group of fumaric acid esters, bardoxolone methyl (methyl 2-cyano-3,12-dioxooleana-1,9(11)dien-28-oate, CDDO-Me, RTA 402), ethyl 2-cyano-3,12-dioxooleana-1,9(11)dien-28-oate, 2-cyano-3,12-dioxooleana-1,9(11)dien-28-oic acid (CDDO), 1 [2-Cyano-3,12-dioxooleana-1,9(11)-dien-28-oyl]imidazole (CDDO-Im), 2-cyano-N-methyl-3,12-dioxooleana-1,9(11)-dien-28 amide (CDDO-methyl amide, CDDO-MA), [(±)-(4bS,8aR,10aS)-10a-ethynyl-4b,8,8-trimethyl-3,7-dioxo-3,4b, 7,8,8a,9,10, 10a-octahydrophenanthrene-2,6-dicarbonitrile] (TBE-31), 2-cyano-3,12-dioxooleana-1,9(11)-dien-28-onitrile (TP-225), 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, and optionally c) instructions for a dosing regimen.

146. A kit of parts comprising: a) a PPAR gamma agonist selected from the group of glitazones, b) an Nrf2 activator selected from the group of fumaric acid esters, 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, auranofin, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), sulfasalazine, 5-aminosalicylic acid (mesalamine), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents, and optionally c) instructions for a dosing regimen.

147. A kit of parts according to the aforementioned embodiments, wherein the PPAR gamma agonist glitazone is selected from pioglitazone and rosiglitazone.

148. A kit of parts according to the aforementioned embodiments, wherein the Nrf2 activator is a fumaric acid ester selected from dialkyl fumarate and monoalkyl fumarate.

149. A kit of parts according to the aforementioned embodiment, wherein the Nrf2 activator is dimethyl fumarate.

150. A method of treating multiple sclerosis or clinically isolated syndrome (CIS) comprising the administration of a pharmaceutical composition comprising a glitazone and a fumaric acid monoalkyl ester and/or fumaric acid dialkyl ester to a patient having multiple sclerosis or clinically isolated syndrome.

151. The method according to one or more of the foregoing embodiments and/or embodiment 150, wherein the fumaric acid dialkyl ester is selected from dimethyl fumarate or diethyl fumarate and the fumaric acid monoalkyl ester is selected from monomethyl hydrogen fumarate or monoethyl hydrogen fumarate.

152. The method according to one or more of the foregoing embodiments and/or embodiment 151, wherein the fumaric acid dialkyl ester is dimethyl fumarate.

153. The method according to one or more of the foregoing embodiments and/or embodiment 150, wherein the glitazone is pioglitazone or rosiglitazone.

154. The method according to one or more of the foregoing embodiments and/or embodiment 150, wherein said composition comprises a fumaric acid dialkyl ester selected from dimethyl fumarate or diethyl fumarate, the glitazone is pioglitazone or rosiglitazone and said pharmaceutical composition is a solid oral dosage form.

155. The method according to one or more of the foregoing embodiments and/or embodiment 154, wherein said fumaric acid dialkyl ester is dimethyl fumarate.

156. A pharmaceutical composition comprising a glitazone, a fumaric acid monoalkyl ester and/or fumaric acid dialkyl ester and, optionally, one or more excipients.

157. The pharmaceutical composition according to one or more of the foregoing embodiments and/or embodiment 156, wherein the fumaric acid dialkyl ester is selected from dimethyl fumarate or diethyl fumarate and the fumaric acid monoalkyl ester is selected from monomethyl hydrogen fumarate or monoethyl hydrogen fumarate.

158. The pharmaceutical composition according to one or more of the foregoing embodiments and/or embodiment 156, wherein the glitazone is pioglitazone or rosiglitazone.

159. The pharmaceutical composition according to one or more of the foregoing embodiments and/or embodiment 157, wherein the fumaric acid dialkyl ester is dimethyl fumarate.

160. The pharmaceutical composition according to one or more of the foregoing embodiments and/or embodiment 156, wherein said pharmaceutical composition comprises a solid oral dosage form.

161. The pharmaceutical composition according to one or more of the foregoing embodiments and/or embodiment 156, wherein the fumaric acid dialkyl ester is selected from dimethyl fumarate or diethyl fumarate, the fumaric acid monoalkyl ester is selected from monomethyl hydrogen fumarate or monoethyl hydrogen fumarate, the glitazone is pioglitazone or rosiglitazone and said pharmaceutical composition is an oral dosage form.

162. The pharmaceutical composition according to one or more of the foregoing embodiments and/or embodiment 161, wherein said fumaric acid dialkyl ester is dimethyl fumarate.

163. The method according to one or more of the foregoing embodiments and/or embodiment 150, wherein said patient has multiple sclerosis.

164. The method according to one or more of the foregoing embodiments and/or embodiment 150, wherein said patient has clinically isolated syndrome.

165. Method of treating or preventing an autoimmune and/or inflammatory disorder, comprising administration of a PPAR gamma agonist selected from the group of glitazones and a bardoxolone alkyl to a patient in need thereof.

166. Method according to one or more of the foregoing embodiments and/or embodiment 165, wherein the bardoxolone alkyl is bardoxolone methyl.

167. Method according to one or more of the foregoing embodiments and/or embodiment 165 or 166, wherein the PPAR gamma agonist glitazone is selected from pioglitazone and rosiglitazone.

168. Method according to one or more of the foregoing embodiments and/or embodiment 165, 166 or 167, wherein the autoimmune and/or inflammatory disorder is chronic kidney disease.

169. Method according to one or more of the foregoing embodiments and/or embodiment 165, 166 or 167, wherein the autoimmune and/or inflammatory disorder is multiple sclerosis.

170. A composition comprising: a) a compound selected from auranofin, sulfasalazine or 5-aminosalicylic acid (mesalamine) and b) a glitazone.

171. A composition comprising: a) a compound selected from auranofin, sulfasalazine or 5-aminosalicylic acid (mesalamine) and b) pioglitazone.

172. A composition comprising: a) a compound selected from auranofin, sulfasalazine or 5-aminosalicylic acid (mesalamine) and b) rosiglitazone.

173. A pharmaceutical composition comprising: a) a compound selected from auranofin, sulfasalazine or 5-aminosalicylic acid (mesalamine), b) a glitazone, such as pioglitazone or rosiglitazone, and optionally c) one or more excipients.

174. Method of treating rheumatoid arthritis, comprising administering the composition according to embodiments 170 to 173, preferably a composition comprising a) auranofin or sulfasalazine and b) a glitazone, to a patient.

175. Method of treating a condition selected from inflammatory bowel diseases, such as ulcerative colitis and Crohn's disease, comprising administering a composition according to embodiments 170 to 173, preferably a composition comprising sulfasalazine or 5-aminosalicylic acid (mesalamine) and a glitazone, to a patient.

In another embodiment of the present invention, the autoimmune and/or inflammatory disease is an oral cavity inflammation or throat inflammation, such as gingivitis, peridontitis or tonsillitis. In a preferred embodiment, such diseases are preferably treated by rinsing the oral cavity and/or throat with a solution or applying a gel or a cream comprising a PPAR gamma agonist, such as a glitazone, preferably pioglitazone or rosiglitazone, and an Nrf2 activator, such as sulforaphane, tert-butylhydroquinone and/or butylated hydroxyanisole or others mentioned herein, preferably 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, or 6-methylsulfinylhexyl isothiocyanate as well as alkyl and alkanoyl esters, alkyl ethers, stereoisomers, tautomers and salts of the aforementioned agents. The above solution or gel can be based on known conventional excipient formulations, such as aqueous formulation of the agents containing polyvinylpyrrolidone as an excipient. Moreover, the solution or gel may contain, in addition to the agents, antibacterials such as chlorhexidine, such as chlorhexidine gluconate, cetylpyridinium chloride, tin fluoride, hexetidine, benzoic acid and its salts, such as sodium benzoate, salicylates, such as methyl salicylate, benzalkonium chloride, methylparaben and/or domiphen bromide.

Therefore, preferred embodiments of the present invention are solutions and gels or creams containing a PPAR agonist and preferably a PPAR gamma agonist, such as a glitazone, preferably pioglitazone or rosiglitazone, and an Nrf2 activator, such as sulforaphane, tert-butylhydroquinone and/or butylated hydroxyanisole or others mentioned herein, in particular 3-tert-butyl-4-hydroxyanisole, 2-tert-butyl-4-hydroxyanisole (BHA), tert-butylquinone (tBQ), tert-butylhydroquinone (tBHQ), 3,5-di-tert-butyl-4-hydroxytoluene (BHT), 2,6-Di-tert-butyl-4-methylene-2,5-cyclohexadien-1-one (2,6-Di-tert-butylquinone methide, BHT-quinone methide), ethoxyquin, gallic acid esters, curcumin, resveratrol, menadione, cinnamic aldehyde, cinnamic acid esters, caffeic acid esters, cafestol, kahweol, lycopene, carnosol, sulforaphane, oltipraz, 5-(4-methoxy-phenyl)-1,2-dithiole-3-thione (ADT), 5-amino-2-hydroxy-benzoic acid 4-(5-thioxo-5H-[1,2]dithiol-3-yl)-phenyl ester (ATB-429), allicin, allylisothiocyanate, zerumbone, phenethyl isothiocyanate, benzyl isothiocyanate, and 6-methylsulfinylhexyl isothiocyanate as well as alkyl and alkanoyl esters, alkyl ethers, stereoisomers, tautomers and salts of the aforementioned agents. In a further preferred embodiment, each of the agents is employed in these solutions, gels or creams in an amount of at least 0.1%, preferably at least 0.5% or at least 1, 2 or 3% (w/w) of the total weight of the solution, cream or gel.

The role of reactive oxygen species and antioxidants in inflammatory diseases has been described in the Journal of Clinical Periodontology Volume 24, Issue 5, 1997, Pages 287-296.

Animal models for peridontitis and gingivitis are well known in the art, e.g., Journal of Biomedicine and Biotechnology Volume 2011, Article ID 754857, 8 pages, doi: 10.1155/2011/754857.

In another preferred embodiment of the present invention, the PPAR gamma agonist, such as pioglitazone or rosiglitazone, is administered with the Nrf2 activator capsaicin for the treatment of an autoimmune and/or inflammatory disorder such as psoriasis, psoriatic arthritis, and arthritis, such as rheumatoid arthritis. The combination can also be used for the treatment of pain, such as neuropathic pain. Combinations with capsaicin are preferably applied topically in the form of a cream, gel or patch. More preferably the invention relates to a cream, gel or patch comprising capsaicin and a PPAR gamma agonist, such as a glitazone, preferably pioglitazone or rosiglitazone.

The cream, gel or patch comprising capsaicin according to the invention provides advantageous results when topically applied in the animal models for psoriasis and rheumatoid arthritis as described herein. In these animal models, the cream, gel or patch comprising capsaicin and a PPAR gamma agonist, such as a glitazone, preferably pioglitazone or rosiglitazone, is applied to the joints or other areas of the skin where symptoms are present.

In another preferred embodiment, the Nrf2 activators cromolyn sodium or nedocromil are combined with a PPAR gamma agonist, such as a glitazone, preferably pioglitazone or rosiglitazone, in order to treat or prevent an autoimmune and/or inflammatory disease, such as asthma, allergies such as seasonal allergy or hay fever, COPD or allergic rhinitis. Preferably, combinations containing cromolyn sodium or any other salt thereof or nedocromil or its salt, such as the sodium salt, as an Nrf2 activator are combined with the PPAR agonist in a solution or gel or a cream or patch, specifically a solution for inhalation or an eyedrop solution, which comprises conventional excipients.

Pioglitazone can be used in its enantiomerically pure or enriched form, as disclosed in WO 2011015868 and WO2011098746, which is particularly advantageous for oral mouth rinses, oral gels, inhalation solutions, eyedrops and topical creams, gels or patches for the treatment of the skin.

Preferably, the PPAR agonist and the Nrf2 activator used in the present invention do not belong to the same chemical class of compounds, i.e., the Nrf2 activator preferably belongs to a different class of compounds than the PPAR agonist.

Solid oral dosage forms comprising the inventive combinations for use in treatment of inflammatory and/or autoimmune diseases are preferred. Solid oral dosage forms are well-known in the art and comprise powders, granules, lozenges, capsules and tablets, such as compressed tablets (CT), sugar-coated tablets (SCT), film-coated tablets (FCT), enteric-coated tablets (ECT), multiple compressed tablets (MCT), which are compressed tablets made by more than one compression cycle, layered tablets, prepared by compressing an additional tablet granulation on a previously compressed granulation, press-coated tablets, controlled-release tablets, effervescent tablets, compressed suppositories, buccal and sublingual tablets, molded tablets (tablet triturates, TT) and hypodermic tablets (HT). Most preferred are solid oral dosage forms that contain both agents together in a single pharmaceutical composition.

Also preferred is a composition comprising dimethyl fumarate, monomethyl fumarate, optionally in form of its zinc, magnesium and/or calcium salts, and a PPAR agonist. The use of this composition in the treatment of psoriasis is particularly preferred.

Also preferred is a PPAR gamma agonist for use in combination with an Nrf2 activator in the treatment of an autoimmune and/or inflammatory disease, according to any of the foregoing embodiments, characterized in that the treatment excludes or does not comprise the administration of hydroxyurea (hydroxycarbamid), particularly if the PPAR gamma agonist and the Nrf2 activator are not used or administered in admixture or in a single pharmaceutical formulation containing both agents together.

In one embodiment of the present invention, the autoimmune and/or inflammatory disorder treated according to the present invention is psoriasis and/or inflammation resulting from or occurring with psoriasis. Preferably, the inventive treatment combines a glitazone with dimethyl fumarate for treating psoriasis and/or inflammation resulting from or occurring with psoriasis. If in this case the glitazone is pioglitazone, particularly if it is not used or administered in admixture with the Nrf2 activator or in a single pharmaceutical formulation containing both agents together, the patient to be treated has preferably not received therapeutic amounts of hydroxyurea before the treatment according to the present invention, is not receiving hydroxyurea concomitantly with the treatment according to the present invention, and preferably neither thereafter, while pioglitazone, dimethyl fumarate or their metabolites are still present in the body. Thus, if the autoimmune and/or inflammatory disorder is psoriasis, the PPAR agonist is pioglitazone and the Nrf2 activator is a fumaric acid ester, the treatment is preferably not combined with hydroxyurea, particularly if the PPAR gamma agonist and the Nrf2 activator are not used or administered in admixture or in a single pharmaceutical formulation containing both agents together.

If the autoimmune and/or inflammatory disorder treated according to the present invention is psoriasis and/or inflammation resulting from or occurring with psoriasis, the glitazone is in one embodiment preferably other than pioglitzaone, such as rosiglitazone, or the Nrf2 activator is other than a fumaric acid ester.

Pioglitazone and rosiglitazone tablets are commercially available and can be used as such for the combination therapy according to the invention.

In one embodiment, the preferred tablets are film-coated tablets containing rosiglitazone maleate equivalent to rosiglitazone, 2 mg, 4 mg, or 8 mg, for oral administration, with the following inactive ingredients: hypromellose 2910, lactose monohydrate, magnesium stearate, microcrystalline cellulose, polyethylene glycol 3000, sodium starch glycolate, titanium dioxide, triacetin, and one or more of the following: synthetic red and yellow iron oxides and talc.

In one embodiment, the preferred tablets for oral administration contain 15 mg, 30 mg, or 45 mg of pioglitazone (as the base) formulated with the following excipients: lactose monohydrate NF, hydroxypropylcellulose NF, carboxymethylcellulose calcium NF, and magnesium stearate NF.

Other formulations can be obtained in analogy to U.S. Pat. No. 6,355,676, U.S. Pat. Nos. 7,976,853 and 6,403,121.

Throughout the specification, the term "no significant PPAR gamma agonistic activity" or "no significant PPAR gamma agonistic effect" means that at the therapeutically useful concentration of the Nrf2 activator, no therapeutically useful PPAR gamma activation can be obtained or measured.

Throughout the specification, the term "no significant effect on Nrf2", "no significantly activating effect on Nrf2" or "no significant effect on Nrf2 activity" means that at the therapeutically useful concentration of the PPAR gamma agonist, no therapeutically useful Nrf2 activation can be obtained or measured.

The terms "monoalkyl fumarate" and "monoalkyl hydrogen fumarate" are used synonymously, such as "monomethyl fumarate" and "monomethyl hydrogen fumarate".

EXAMPLES

Example 1

Preparation of Enteric-Coated Micro-Tablets in Capsules Containing 120.0 mg of Dimethyl Fumarate Following U.S. Pat. No. 7,320,999, 12,000 kg of dimethyl fumarate are crushed, mixed and homogenized by means of a sieve 800. Then an excipient mixture with the following composition is prepared: 17.50 kg of starch derivative (STA-RX® 1500), 0.30 kg of microcrystalline cellulose (Avicel® PH-101), 0.75 kg of PVP (Kollidon® 120), 4.00 kg of Primogel®, and 0.25 kg of colloidal silicic acid (Aerosil®). Dimethyl fumarate is added to the entire powder mixture, mixed, homogenized by means of a sieve 200, processed in the usual manner with a 2% aqueous solution of polyvinyl pyrrolidone (Kollidon® K25) to obtain a binder granulate and then mixed in the dry state with the outer phase. Said outer phase consists of 0.50 kg of Mg stearate and 1.50 kg of talcum.

The powder mixture is compressed in the usual manner into 10 mg micro-tablet cores.

To achieve resistance to gastric acid a solution of 2.250 kg of hydroxypropyl methylcellulose phthalate (HPMCP, Pharmacoat® HP 50) is dissolved in portions in a mixture of the following solvents: 13.00 L of acetone, 13.50 L of ethanol (94 wt. %, denatured with 2% of ketone) and 1.50 L of demineralized water. As a plasticizer, castor oil (0.240 kg) is added to the finished solution, which is applied in portions onto the micro-tablet cores in the customary manner.

After drying is completed, a suspension of the following composition is applied as a film coat in the same apparatus: 0.340 kg of talcum, 0.400 kg of titanium (VI) oxide (Kronos RN 56), 0.324 kg of colored lacquer (L red lacquer 86837), 4.800 kg of Eudragit E 12.5% and 0.120 kg of polyethylene glycol 6000, pH 11 XI in a solvent mixture of the following composition: 8.170 kg of 2-propanol, 0.200 kg of demineralized water and 0.600 kg of glycerine triacetate (Triacetin). This procedure resulted in enteric-coated micro-tablets.

Subsequently, the enteric-coated micro-tablets are filled into hard gelatine capsules and are sealed for use according to the invention.

Micro pellets can be obtained similarly according to U.S. Pat. No. 7,320,999.

Example 2

Preparation of Tablets Containing Pioglitazone and Dimethyl Fumarate in Separate Tablet Layers According to U.S. Pat. No. 8,071,130, a mixture of pioglitazone hydrochloride (99.2 g), croscarmellose sodium (13.2 g) and lactose (184.9 g) is granulated by spraying thereon 136.2 g of an aqueous solution of hydroxypropylcellulose (6.81 g) in a fluid bed granulator (manufactured by Powrex Corp., Model: LAB-1). The resulting granulated powder is then granulated by spraying a suspension obtained by dispersing lactose (36 g) in 148.6 g of an aqueous solution of hydroxypropylcellulose (7.59 g) thereon in a fluid bed granulator (manufactured by Powrex Corp., Model: LAB-1) to obtain pioglitazone hydrochloride-containing granulated powder coated with lactose. To a part (23.18 g) of the granulated powder thus obtained, croscarmellose sodium (0.728 g) and magnesium stearate (0.096 g) are added and mixed to obtain pioglitazone hydrochloride-containing mixed powder. The pioglitazone hydrochloride-containing mixed powder is compressed in the form of laminate with a powder obtained according to example 1, containing dimethyl fumarate, a starch derivative (STA-RX® 1500), microcrystalline cellulose (Avicel® PH 101), PVP (Kollidon® 120), Primogel®, and colloidal silicic acid (Aerosil®).

Example 3

According to U.S. Pat. No. 7,976,853, hydroxypropyl cellulose (26.4 g, Grade SSL, Nippon Soda Co., Ltd.) (viscosity of 5% aqueous solution at 20° C., 8 mPa·s), polyethylene glycol 6000 (1.32 g), titanium oxide (2.64 g) and pioglitazone hydrochloride (16.5 g) are dispersed in water (297 g) to give a coating solution. The enteric-coated micro-tablets obtained in example 1 are fed in a film coating equipment (Hicoater-Mini, Freund Industrial Co. Ltd.) and coated with the aforementioned coating solution to give a coated preparation. Subsequently, these enteric-coated micro-tablets, which are coated with pioglitazone hydrochloride, are filled into hard gelatine capsules and are sealed for use according to the present invention.

Alternatively, according to example 1, an enteric-coated tablet containing the desired amount of dimethyl fumarate can be obtained, followed by a coating with a pioglitazone formulation as described above. The tablets can be used as such for the combination treatment according to the invention.

Example 4

A mixture of pioglitazone hydrochloride (99.2 g), croscarmellose sodium (13.2 g) and lactose (184.9 g) is granulated by spraying thereon 136.2 g of an aqueous solution of hydroxypropylcellulose (6.81 g) in a fluid bed granulator (manufactured by Powrex Corp., Model: LAB-1). The resulting granulated powder is then granulated by spraying a suspension obtained by dispersing lactose (36 g) in 148.6 g of an aqueous solution of hydroxypropylcellulose (7.59 g) thereon in a fluid bed granulator (manufactured by Powrex Corp., Model: LAB-1) to obtain pioglitazone hydrochloride-containing granulated powder coated with lactose. A desired amount of the granulated powder thus obtained is filled into capsules containing dimethyl fumarate enteric-coated micro-tablets obtained according to example 1, which are thereafter sealed.

Example 5

A capsule is filled with a dispersion of 20 mg of amorphous bardoxolone methyl in methacrylic acid copolymer Type C, USP in a 4/6 weight ratio of bardoxolone methyl to methacrylic acid copolymer Type C, USP having the following composition, prepared according to US 2012/022156:

Amorphous bardoxolone methyl as 40% dispersion: 11.36%

SMCC (90LM, silicified microcrystalline cellulose, as listed in the FDA Inactive Ingredients Guide): 36.36% lactose monohydrate: 40.91% hydroxypropyl methylcellulose: 6.82% colloidal silicon dioxide: 0.91% magnesium stearate: 0.91% sodium lauryl sulfate: 2.73%.

In addition, the capsule is filled with an equivalent of 45 mg of pioglitazone in the form of its hydrochloride as a granulated powder coated with lactose obtained according to the first part of example 4. The capsule is thereafter sealed for use.

Alternatively, the bardoxolone methyl containing mixture and the pioglitazone containing mixture can be compressed into a tablet, preferably a layered tablet, wherein the formulations are arranged in a laminar manner. In one embodiment, an enteric coat is applied to the tablet.

General Experimental Protocols

If not mentioned otherwise, treatment in the following animal models consists of, or animals are treated with, dimethyl fumarate and pioglitazone in the form of its hydrochloride, which is dissolved or dispersed in 0.5% methylcellulose/0.1% Tween80 in distilled water and administered by oral gavage twice daily. Treatment groups are generally as follows: vehicle alone, dimethyl fumarate alone, pioglitazone alone or the combination of dimethyl fumarate and pioglitazone. The combination according to the invention results in an improved response to treatment over the vehicle and the respective agents alone.

The effect of the combinations according to the present invention in the treatment of cancer and preferably hematologic cancers such as CLL and AML can be found in Blood. 2006 Nov. 15; 108(10):3530-7 and Cancer Res Jun. 15, 2010 70; 4949.

Animal Model for Assessing the Therapeutic and Preventive Effect of the Combination of a PPAR Gamma Agonist and an Nrf2 Activator in Oral Cavity Inflammation and Throat Inflammation Including Gingivitis, Peridontitis, Tonsillites Specific pathogen-free C3H/HeN mice are infected according to J. Periodontol. 2000 July; 71(7):1167-73 and are treated daily by oral gavage according to the general example with pioglitatzone hydrochloride, sulforaphane or tert-butylhydroquinone or the combination of pioglitatzone hydrochloride and sulforaphane or pioglitazone hydrochloride and tert-butylhydroquinone. The treatment with the combinations results in prevention or delayed onset and reduced signs of inflammation compared to the individual agents and compared to non-treated animals. Similar qualitative results are obtained by applying the treatment by daily rinsing the mouths of the animals for 2 minutes with a solution of the agents.

Animal Model for Assessing the Therapeutic and Preventive Effect of the Combination of a PPAR Gamma Agonist and an Nrf2 Activator in Rheumatoid Arthritis Animals are prepared according to Wilder, R. L. 2001 (Streptococcal Cell Wall Arthritis) Current Protocols in Immunology. 26:15.10.1-15.10.12 and treated daily by oral gavage according to the general example with pioglitatzone hydrochloride, dimethyl fumarate or the combination of the agents. The treatment with the combination results in prevention or delayed onset and reduced signs of arthritis and inflammation compared to the individual agents and compared to non-treated animals.

Use of an Animal Model to Assess Effect in Treating Psoriasis

The severe combined immunodeficient (SCID) mouse model can be used to evaluate the efficacy of compounds for treating psoriasis in humans (Boehncke, Ernst Schering Res Found Workshop 2005, 50, 213-34; and Bhagavathula et al., J Pharmacol Expt 7 Therapeutics 2008, 324(3), 938-947).

SCID mice are used as tissue recipients. One biopsy for each normal or psoriatic volunteer is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples are obtained for microscopy. Epidermal thickness is measured. Tissue sections are stained with an antibody to the proliferation-associated antigen Ki-67 and with an anti-human CD3+ monoclonal antibody to detect human T lymphocytes in the transplanted tissue.

Sections are also probed with antibodies to c-myc and β-catenin. A positive response to treatment is reflected by a reduction in the average epidermal thickness of the psoriatic skin transplants. A positive response is also associated with reduced expression of Ki-67 in keratinocytes.

General EAE Animal Model for Assessing Therapeutic Effect of the Combination of a PPAR Gamma Agonist and an Nrf2 Activator for Treating Multiple Sclerosis Animals and EAE Induction Female C57BL/6 mice, 8-10 weeks old (Harlan Laboratories, Livermore, Calif.), are immunized subcutaneously in the flank and mid-scapular region with 200 µg of myelin oligodendrocyte glycoprotein peptide (MOG3S-Ss) (synthesized by Invitrogen) emulsified (1:1 volume ratio) with complete Freund's adjuvant (CFA) (containing 4 mg/nL *Mycobacterium tuberculosis*). Emulsion is prepared by the syringe-extrusion method with two glass Luer-Lok syringes connected by a 3-way stopcock. Mice are also given an intraperitoneal injection of 200 ng pertussis toxin (List Biological Laboratories, Inc., Campbell, Calif.) on the day of immunization and on day two post-immunization. Mice are weighed and examined daily for clinical signs of experimental autoimmune encephalomyelitis (EAE). Food and water are provided ad libitum and once animals start to show disease, food is provided on the cage bottom.

Clinical Evaluation

Mice are scored daily beginning on day 7 post-immunization. The clinical scoring scale is as follows (Miller and Karplus, Current Protocols in Immunology 2007, 15.1.1-15.1.18): 0=normal; 1=limp tail or hind limb weakness (defined by foot slips between bars of cage top while walking); 2=limp tail and hind limb weakness; 3=partial hind limb paralysis (defined as no weight bearing on hind limbs but can still move one or both hind limbs to some extent); 4=complete hind limb paralysis; 5=moribund state (includes forelimb paralysis) or death.

Animal Model for Assessing Therapeutic Effect of the Combination of a PPAR Gamma Agonist and an Nrf2 Activator for Treating Multiple Sclerosis Experiments are conducted on female mice aged 4-6 weeks belong to the C57BL/6 strain weighing 17-20 g. Experimental autoimmune encephalomyelitis (EAE) is actively induced using >95% pure synthetic myelin oligodendrocyte glycoprotein peptide 35-55 (MOG35-55, MEVGWYRSPFSRVVHLYRNGK, SEQ ID NO: 1). Each mouse is anesthetized and receives 200 µg of MOG peptide and 15 µg of Saponin extract from quillaja bark emulsified in 100 µL of phosphate-buffered saline. A 25 µL volume is injected subcutaneously over four flank areas. Mice are also intraperitoneally injected with 200 ng of pertussis toxin in 200 µL of PBS. A second, identical injection of pertussis toxin is given after 48 h.

Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hindlimbs); 2, unilateral partial hindlimb paralysis; 2.5, bilateral hindlimb paralysis; 3, complete bilateral hindlimb paralysis; 3.5, complete hindlimb paralysis and unilateral forelimb paralysis; 4, total paralysis of hindlimbs and forelimbs (Eugster et al., Eur J Immunol 2001, 31, 2302-2312).

Inflammation and demyelination are assessed by histology on sections from the CNS of EAE mice. Mice are sacrificed after 30 or 60 days and whole spinal cords are removed and placed in 0.32 M sucrose solution at 40° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then resuspended in PBS and counted. Cells at a density of about $3\times10^6$ cells/mL are incubated overnight with 20 µg/mL of MOG peptide. Supernatants from stimulated cells are assayed for IFN-γ protein levels using an appropriate mouse IFN-γ immunoassay system.

Use of an Animal Model to Assess Effect in Treating Inflammatory Bowel Disease

Animal models of inflammatory bowel disease are described by Jurjus et al, J

Pharmaocol Toxicol Methods 2004, 50, 81-92; Villegas et al, Int'l lmmunopharmacol 2003, 3, 1731-1741; and Murakami et al, Biochemical Pharmacol 2003, 66, 1253-1261. For example, the following protocol can be used to assess the effect of the combination according to the present invention for treating inflammatory bowel disease, Crohn's disease and colitis.

Female ICR mice are used. Mice are divided into treatment groups. Groups are given either water (control), 5% DSS in tap water at the beginning of the experiment to induce colitis, or treatment. After administering the treatment for 1 week, 5% DSS in tap water is also administered to the groups receiving treatment for 1 week. At the end of the experiment, all mice are killed and the large intestines are removed. Colonic mucosa samples are obtained and homogenized. Proinflammatory mediators (e.g., IL-1α, IL-1β, TNF-α, PGE2, and PGF2α) and protein concentrations are quantified. Each excised large intestine is histologically examined and the damage to the colon scored.

Clinical Trial for Assessing Effect in Treating Asthma

Adult subjects (nonsmokers) with stable mild-to-moderate asthma are enrolled (see, e.g., Van Schoor and Pauwels, Eur Respir J 2002, 19, 997-1002). A randomized, double-blind, placebo-controlled, two-period crossover design is used. Placebo, dimethyl fumarate alone, pioglitazone alone and a combination of dimethyl fumarate and pioglitazone are administered orally. The combination according to the invention results in an improved response to treatment over the vehicle and the agents alone.

Use of an Animal Model to Assess Effect in Treating Chronic Obstructive Pulmonary Disease An animal model using mice chronically exposed to cigarette smoke can be used for assessing efficacy in treating emphysema (see, e.g., Martorana et al., Am J Respir Crit Care Med 2005, 172, 848-835; and Cavarra et al., Am J Respir Crit Care Med 2001, 164, 886-890). Six-week old C57B1/6J male mice are used. In the acute study, the mice are exposed either to room air or to the smoke of five cigarettes for 20 minutes. In the chronic study, the mice are exposed to either room air or to the smoke of three cigarettes/day for 5 days/week for 7 months.

In the acute study, mice are divided into three groups. These groups are then divided into five subgroups of 10 mice each as follows: (1) no treatment/air-exposed; (2) no treatment/smoke-exposed; (3) the combination of dimethyl fumarate and pioglitazone plus smoke-exposed; (4) pioglitazone plus smoke-exposed; and (5) dimethyl fumarate plus smoke-exposed. In the first group, trolox equivalent antioxidant capacity is assessed at the end of the exposure in bronchoalveolar lavage fluid; in the second group, cytokines and chemokines are determined in bronchoalveolar lavage fluid using a commercial cytokine panel at 4 hours; and in the third group bronchoalveolar lavage fluid cell count is assessed at 24 hours.

Animal Models for Assessing Therapeutic Effect of the Combination of a PPAR Gamma Agonist and an Nrf2 Activator for Treating Parkinson's Disease MPTP Induced Neurotoxicity MPTP, or 1-methyl-4-phenyl-1,2,3,6-tetrahydropyridine, is a neurotoxin that produces a Parkinsonian syndrome in both man and experimental animals. Studies of the mechanism of MPTP neurotoxicity show that it involves the generation of a major metabolite, MPP+, formed by the activity of monoamine oxidase on MPTP. Inhibitors of monoamine oxidase block the neurotoxicity of MPTP in both mice and primates. The specificity of the neurotoxic effects of MPP+ for dopaminergic neurons appears to be due to the uptake of MPP+ by the synaptic dopamine transporter. Blockers of this transporter prevent MPP+ neurotoxicity. MPP+ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that MPP+ administered intrastriatally to rats produces significant depletion of ATP as well as increased lactate concentration confined to the striatum at the site of the injections. Compounds that enhance ATP production can protect against MPTP toxicity in mice.

Mice or rats are treated either with vehicle alone, dimethyl fumarate alone, pioglitazone alone or the combination of dimethyl fumarate and pioglitazone for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striata are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Haloperidol-Induced Hypolocomotion

The ability of a compound to reverse the behavioral depressant effects of dopamine antagonists, such as haloperidol, in rodents is considered a valid method for screening drugs with potential anti-Parkinsonian effects (Mandhane, et al., Eur. J. Pharmacol 1997, 328, 135-141). Hence, the ability of the treatment to block haloperidol-induced deficits in locomotor activity in mice can be used to assess both in vivo and potential anti-Parkinsonian efficacy.

Mice used in the experiments are housed in a controlled environment and allowed to acclimate before experimental use. One and one-half (1.5) hours before testing, mice are administered 0.2 mg/kg haloperidol, a dose that reduces baseline locomotor activity by at least 50%. Treatment is administered a suitably long prior to testing. The animals are then placed individually into clean, clear polycarbonate cages with flat perforated lids.

Horizontal locomotor activity is determined by placing the cages within a frame containing a 3×6 array of photocells interfaced to a computer to tabulate beam interrupts. Mice are left undisturbed to explore for 1 h, and the number of beam interruptions made during this period serves as an indicator of locomotor activity, which is compared with data for control animals for statistically significant differences.

6-Hydroxydopamine Animal Model

The neurochemical deficits seen in Parkinson's disease can be reproduced by local injection of the dopaminergic neurotoxin 6-hydroxydopamine (6-OHDA) into brain regions containing either the cell bodies or axonal fibers of the nigrostriatal neurons. By unilaterally lesioning the nigrostriatal pathway on only one side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimate before experimental use. Fifteen minutes prior to surgery, animals are given an intraperitoneal injection of the noradrenergic uptake inhibitor desipramine (25 mg/kg) to prevent damage to nondopamine neurons. Animals are then placed in an anesthetic chamber and anesthetized using a mixture of oxygen and isoflurane. Once unconscious, the animals are transferred to a stereotaxic frame, where anesthesia is maintained through a mask. The top of the head is shaved and sterilized using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to a position above the right medial forebrain bundle at −3.2 mm anterior posterior, −1.5 mm medial lateral from the bregma, and to a depth of 7.2 mm below the dura mater. Two minutes after lowering the cannula, 6-OHDA is infused at a rate of 0.5 µL/min over 4 min, to provide a final dose of 8 µg. The cannula is left in place for an additional 5 min to facilitate diffusion before being slowly withdrawn. The skin is then sutured shut, and the animal is removed from the sterereotaxic frame and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover around the edge of the bowl and extending to a height of 29 cm. To assess rotation, rats are placed in a cloth jacket attached to a spring tether connected to an optical rotameter positioned above the bowl, which assesses movement to the left or right either as partial(45°) or full(360°) rotations.

Treatment is given for a suitable period prior to testing. Animals are given a subcutaneous injection of a subthreshold dose of apomorphine, and are then placed in the harness. The number of rotations are recorded for one hour. The total number of full contralateral rotations during the hour test period serves as an index of anti-Parkinsonian drug efficacy.

Animal Model for Assessing Therapeutic Effect for Treating Alzheimer's Disease

Heterozygous transgenic mice expressing the Swedish AD mutant gene hAPPK670N, M671L (Tg2576; Hsiao, Learning & Memory 2001, 8, 301-308), are used as an animal model of Alzheimer's disease. Animals are housed under standard conditions with a 12:12 light/dark cycle and food and water available ad libitum. Beginning at 9 months of age, mice are divided into two groups. The groups of animals receive treatment over six weeks.

Behavioral testing is performed at each drug dose using the same sequence over two weeks in all experimental groups: (1) spatial reversal learning, (2) locomotion, (3) fear conditioning, and (4) shock sensitivity.

Acquisition of the spatial learning paradigm and reversal learning are tested during the first five days of test compound administration using a water T-maze as described in Bardgett et al., Brain Res Bull 2003, 60, 131-142. Mice are habituated to the water T-maze during days 1-3, and task acquisition begins on day 4. On day 4, mice are trained to find the escape platform in one choice arm of the maze until 6 to 8 correct choices are made on consecutive trials. The reversal learning phase is then conducted on day 5. During the reversal learning phase, mice are trained to find the escape platform in the choice arm opposite from the location of the escape platform on day 4. The same performance criteria and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The capacity of an animal for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial, 80 db, 2800 Hz tone foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the response of the animal to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined.

On day 12, the animals are tested to assess their sensitivity to the conditioning stimulus, i.e., foot shock. Following the last day of behavioral testing, animals are anesthetized and the brains removed, post-fixed overnight, and sections cut through the hippocampus. The sections are stained to image β-amyloid plaques.

Data is analyzed using appropriate statistical methods.

Animal Model for Assessing Therapeutic Effect for Treating Huntington's Disease

Neuroprotective Effects in a Transgenic Mouse Model of Huntington's Disease

Transgenic HD mice of the N171-82Q strain and non-transgenic littermates are treated from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice showing improved response to treatment with the combination of dimethyl fumarate and pioglitazone remain on the rotarod for a longer period of time and travel farther than mice administered vehicle or either agent alone.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease.

In this malonate model for Huntington's disease, treatment is administered at an appropriate dose, dosing interval, and route to male Sprague-Dawley rats. Treatment is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 μL of 3 μmol malonate are made into the left striatum at the level of the bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-triphenyltetrazolium chloride. Slices are stained in the dark at room temperature for 30 min and then removed and placed in 4% paraformaldehyde, pH 7.3. Lesions, noted by pale staining, are evaluated on the posterior surface of each section. The measurements are validated by comparison with measurements obtained on adjacent Nissl stained sections.

Animal Model for Assessing Therapeutic Effect for Treating Amyotrophic Lateral Sclerosis A murine model of SOD1 mutation-associated ALS has been developed in which mice express the human superoxide dismutase (SOD) mutation glycine-alanine at residue 93 (SOD1). These SOD1 mice exhibit a dominant gain of the adverse property of SOD, and develop motor neuron degeneration and dysfunction similar to that of human ALS. The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and, as the disease progresses, profound motor neuron loss. Studies are performed on transgenic mice overexpressing human Cu/Zn-SOD G93A mutations (B6S JL-TgN (SOD1-G93A) 1 Gur) and non-transgenic B6/SJL mice and their wild litter mates. Mice are housed on a 12-hr day/light cycle and (beginning at 45 d of age) allowed ad libitum access to either test compound-supplemented chow, or, as a control, regular formula cold press chow processed into identical pellets. Genotyping can be conducted at 21 days of age as described in Gurney et al., Science 1994, 264(5166), 1772-1775. The SOD1 mice are separated into groups and treatment is administered for a suitable period.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0—normal reflex of the hind limbs (animal will splay its hind limbs when lifted by its tail); 1—abnormal reflex of hind limbs (lack of splaying of hind limbs when animal is lifted by the tail); 2—abnormal reflex of limbs and evidence of paralysis; 3—lack of reflex and complete paralysis; and 4—inability to right when placed on the side in 30 seconds or found dead. The primary end point is survival with secondary end points of neurological score and body weight. Neurological score observations and body weight are made and recorded five days per week. Data analysis is performed using appropriate statistical methods. The rotarod test evaluates the ability of an animal to stay on a rotating dowel, allowing evaluation of motor coordination and proprioceptive sensitivity. The apparatus is a 3 cm diameter automated rod turning at, for example, 12 rounds per min. The rotarod test measures how long the mouse can maintain itself on the rod without falling. The test can be stopped after an arbitrary limit of 120 sec. Should the animal fall down before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 $cm^2$) situated above a plane support. The number of times the mice put their paws through the grid is counted and serves as a measure for motor coordination. The hanging test evaluates the ability of an animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mouse. The sciatic nerve is stimulated with a single 0.2 msec pulse at supramaximal intensity (12.9 mA). The amplitude (mV) and the latency of the response (ms) are measured. The amplitude is indicative of the number of active motor units, while distal latency reflects motor nerve conduction velocity. The effect of the combinations according to the present invention can also be evaluated using biomarker analysis. To assess the regulation of protein biomarkers in SOD1 mice during the onset of motor impairment, samples of lumbar spinal cord (protein extracts) are applied to ProteinChip arrays with varying surface chemical/biochemical properties and analyzed, for example, by surface enhanced laser desorption/ionization or time of flight mass spectrometry. Then, using integrated protein mass profile analysis methods, data is used to compare protein expression profiles of the various treatment groups. Analysis can be performed using appropriate statistical methods.

Animal Model for Assessing Therapeutic Effect in Myasthenia Gravis

Induction and clinical evaluation of EAMG are according to International Immunology, Vol. 10, No. 9, pp. 1359-1365.

B6 and μMT mice are immunized s.c. along the shoulders and back with 20 μg AChR with CFA in a total volume of 100 μl, and boosted twice at monthly intervals with 20 μg of AChR in CFA s.c. at four sites on the shoulders and thighs. The mice are observed every other day in a blinded fashion for signs of muscle weakness characteristic of EAMG. The clinical symptoms are graded between 0 and 3 (4): 0, no definite muscle weakness; 1, normal strength at rest but weak with chin on the floor and inability to raise the head after exercise consisting of 20 consecutive paw grips; 2, as grade 1 and weakness at rest; and 3, moribund, dehydrated and paralyzed. Clinical EAMG is confirmed by injection of neostigmine bromide and atropine sulfate. The mice are grouped and treatment is administered for a suitable period before testing.

Animal Model for Assessing the Therapeutic Effect in Alopecia

The Dundee experimental bald rat (DEBR) and the C3H/HeJ mouse are well-established animal models for alopecia areata and can be used for the study of genetic aspects, pathogenesis and therapy of the disease. In C3H/HeJ mice alopecia areata can be experimentally induced by grafting lesional skin from an affected mouse to a histocompatible recipient, which offers the possibility to study the influence of various factors on the development of the disease. The mice are grouped and treatment is administered for a suitable period before testing.

General Experimental Protocol

Treatment in the following animal models consists of dimethyl fumarate dissolved or dispersed in 0.5% Hydroxypropylmethylcellulose (HPMC) K4 M/0.25% Tween 20 and pioglitazone dissolved or dispersed in kleptose in distilled water. Treatments were administered by oral gavage once or twice daily. Treatment groups were generally as follows: appropriate vehicles, dimethyl fumarate, pioglitazone and the combination of dimethyl fumarate and pioglitazone. The combination according to the invention results in an improved response to treatment over the vehicle and the respective agents alone.

EAE Animal Model for Assessing Therapeutic Effect of the Combination of the PPAR Gamma Agonist and Nrf2 Activator for Treating Multiple Sclerosis Female C57BL/6 mice between 7-8 weeks old are ordered (Janvier (France) or Charles River) and used between 9-11 weeks after an acclimatization period. Experimental autoimmune encephalomyelitis (EAE) is actively induced using >95% pure synthetic myelin oligodendrocyte glycoprotein peptide 35-55 (MOG35-55, Met-Glu-Val-Gly-Trp-Tyr-Arg-Ser-Pro-Phe-Ser-Arg-Val-Val-Hi s-Leu-Tyr-Arg-Asn-Gly-Lys (SEQ ID NO: 1), Ref SC1272, NeoMPS). Each mouse is anesthetized and receives a subcutaneous injection of 100 μl of Complete Freund's Adjuvant (Ref 263810, Difco) emulsion containing 200 of MOG35-55 and 250 μg of dried and killed *M. tuberculosis* H37 Ra (Ref 231141, Difco) into the lower back. The emulsion is prepared by the syringe method with two syringes connected through a Luer-Lok tube. Mice also receive an intra-peritoneal injection of 300 ng of pertussis toxin (Ref BML-G100, Enzo Lifescience) diluted in 200 μl PBS. Pertussis toxin injection is repeated 48 hours later. Mice are weighed and examined daily for clinical signs of EAE. Food and water are provided ad libitum.

Clinical Evaluation

Animals were assessed for neurological deficits (clinical score) and weighed daily. The clinical scoring scale is as follows; 0=no signs; 0.5=distal limp tail; 1=complete tail paralysis; 1.5=hind limb weakness; 2=unilateral partial hind limb paralysis; 2.5=bilateral partial hind limb paralysis; 3=complete bilateral hind limb paralysis; 3.5=fore limb weakness and complete bilateral hind limb paralysis; 4=quadriplegia/moribund; 5=death from EAE.

Results: Assessment of Treatment with Dimethyl Fumarate in Combination with Pioglitazone in the Form of its Hydrochloride Forty female C57BL/6 mice aged 8-9 weeks were immunized according to the EAE protocol described in the Methods section. Mice were sorted into 4 different treatment groups (n=10) and received treatment with HPMC 0.5%/Tween20 0.25% (vehicle for dimethyl fumarate) b.i.d. plus Kleptose 20% (vehicle for pioglitazone) q.d., dimethyl fumarate 60 mg/kg b.i.d. plus Kleptose 20% q.d., pioglitazone 10 mg/kg q.d. plus HPMC 0.5%/Tween20 0.25% b.i.d. or dimethyl fumarate 60 mg/kg b.i.d. plus pioglitazone 10 mg/kg q.d. For simplicity, the vehicle treatments were not mentioned in graph legends and the groups above were named as control, dimethyl fumarate 60 mg/kg bid, pioglitazone 10 mg/kg q.d. and dimethyl fumarate+pioglitazone, respectively. Drug treatment started at day 0 post-immunization. As shown in FIG. 1A, immunization of C57BL/6 mice with MOG35-55 induces locomotor disability with the clinical signs arising around day 9 post-immunization.

The effect of the combination (dimethyl fumarate+pioglitazone) treatment significantly reduced average daily clinical scores (FIG. 1A). The combination efficacy was more pronounced and statistically different from the effect of individual treatments. Suppression of inflammation-induced cachexia acts as a reliable marker of treatment benefit. Combination treatment (dimethyl fumarate+pioglitazone) treatment significantly improved body weight in comparison to vehicle or single drug treatments (FIG. 1B).

The effect of drug treatment on the prevalence of disease is analysed in FIG. 2. The onset of disease is defined at the point each mouse first exhibits a clinical score ≥1. FIG. 2A depicts a Kaplan-Meier analysis showing that control group mice start developing EAE from day 9 with complete susceptibility by day 14 post-immunization. The combination treatment with dimethyl fumarate+pioglitazone shifted the EAE onset curve. Not all animals treated with the drug combination developed signs of disease until the termination of the experiment, i.e., day 22 post-immunization. The effect of the combination treatment was statistically different not only in comparison with the control group, but also in comparison with each of the drugs dosed alone. FIG. 2B is a different representation of the same data. On average, mice treated with vehicle, dimethyl fumarate or pioglitazone alone indistinctly exhibited the first clinical signs of disease around day 12-13 post-immunization, whereas in the combination group the average onset of EAE was around day 17 post-immunization. The effect of the combination treatment was again statistically different from and more potent than the other treated groups. This data shows that combination treatment results in a synergistic treatment effect which is not observed with individual treatments.

Gastrointestinal changes including hemorrhage are known side effects of dimethyl fumarate treatment. Combination treatment and dimethyl fumarate treatment alone resulted in similar hyperplasia of the macrovilosity of the stomach. There was no worsening of symptoms with combination treatment. Representative images of the stomachs of mice chronically treated for 22 days with dimethyl fumarate, pioglitazone or their vehicles are shown in FIG. 3 to demonstrate some of these observations. Importantly, the synergistic efficacy discussed in the previous paragraphs was not associated with increased gastrointestinal adverse events.

Figure 1:
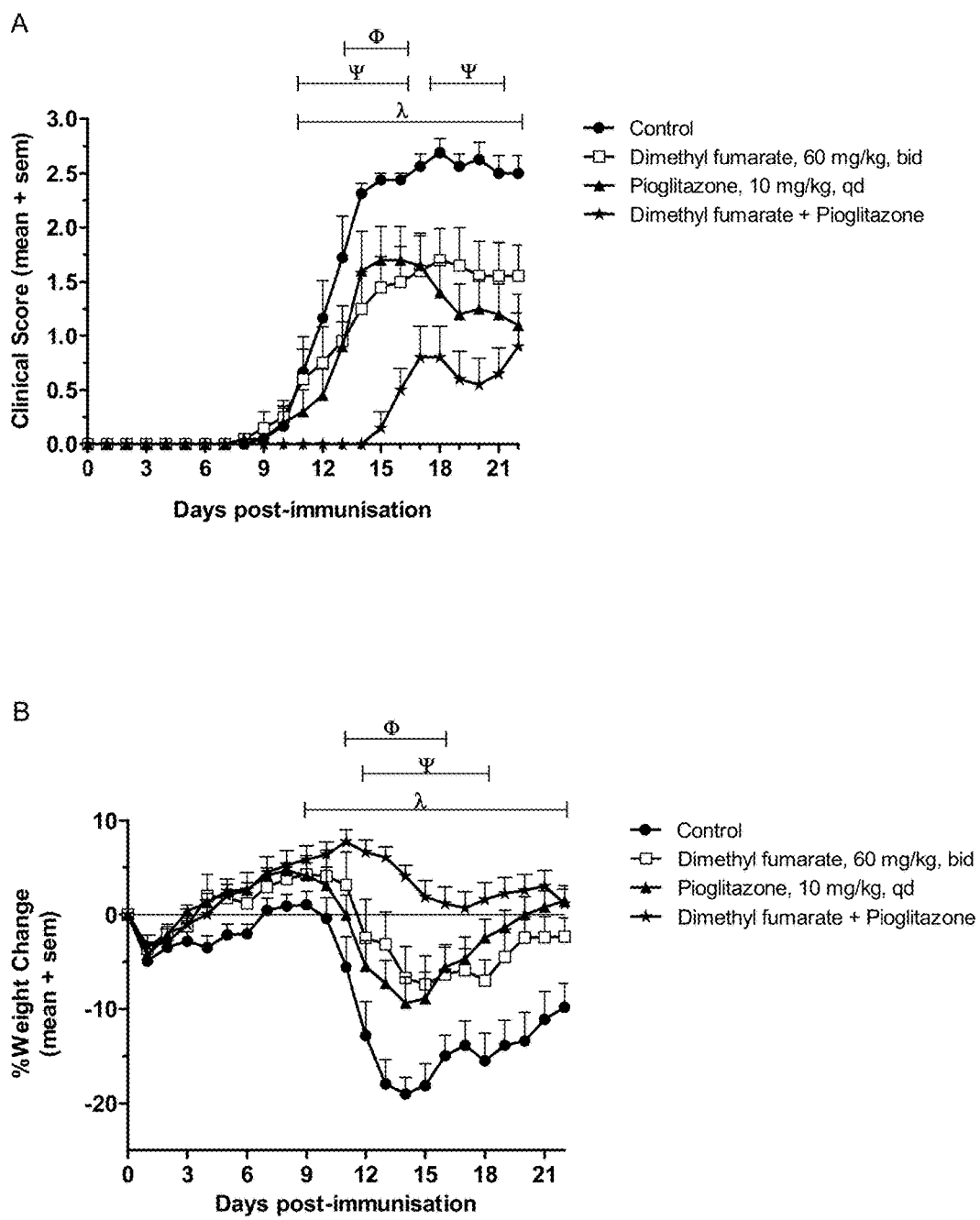
FIG. 1: Combination treatment with dimethyl fumarate+pioglitazone is significantly more efficacious than each individual drug as stand-alone treatments or treatment with vehicle on mean clinical scores and also on body weight changes associated with disease. Average clinical scores (A) and percentage body weight changes (B) of MOG35-55 mice treated with vehicle, dimethyl fumarate, pioglitazone or a combination of both drugs from day 0 post-immunization. Kruskal-Wallis (non-parametric ANOVA) with Dunn's multiple test correction was applied in A and Student's t-test in B. Horizontal bars represent P<0.05 where λ compares combination treatment versus vehicle, Ψ combination treatment versus dimethyl fumarate and Φ combination treatment versus pioglitazone.
Figure 2:
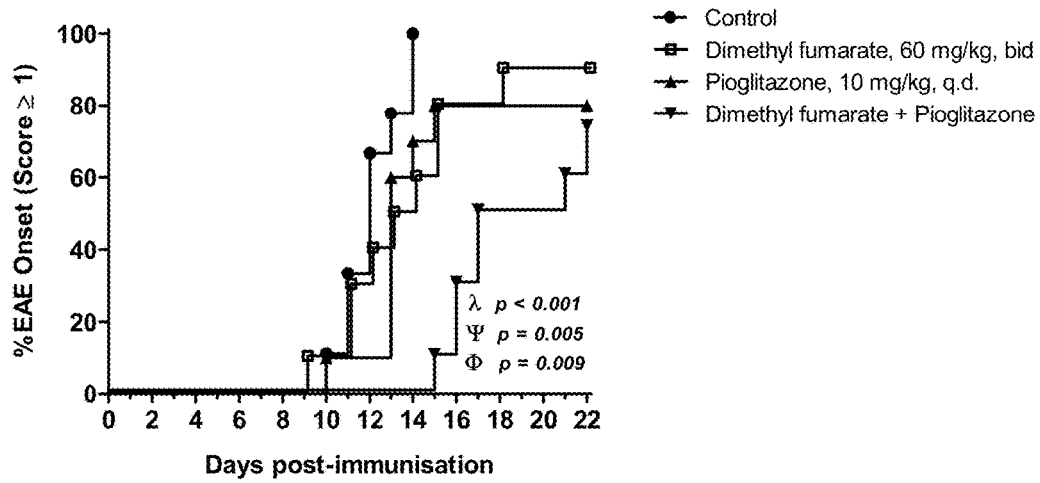
FIG. 2: Combination treatment with dimethyl fumarate+pioglitazone causes a delay in the onset of disease in comparison with each individual drug as stand-alone treatments or treatment with vehicle. Kaplan-Meier analysis of the disease prevalence curves (A) and average day of onset of disease (B) of MOG35-55 mice treated with vehicle, dimethyl fumarate, pioglitazone or a combination of both drugs from day 0 post-immunization. The onset of disease was defined as the day mice first exhibit a clinical score ≥1. Gehan-Breslow-Wilcoxon test was applied in A and Kruskal-Wallis followed by Dunn's multiple test correction in B. Horizontal bars represent P<0.05 where λ compares combination treatment versus vehicle, W combination treatment versus dimethyl fumarate and Φ combination treatment versus pioglitazone.
Figure 2:
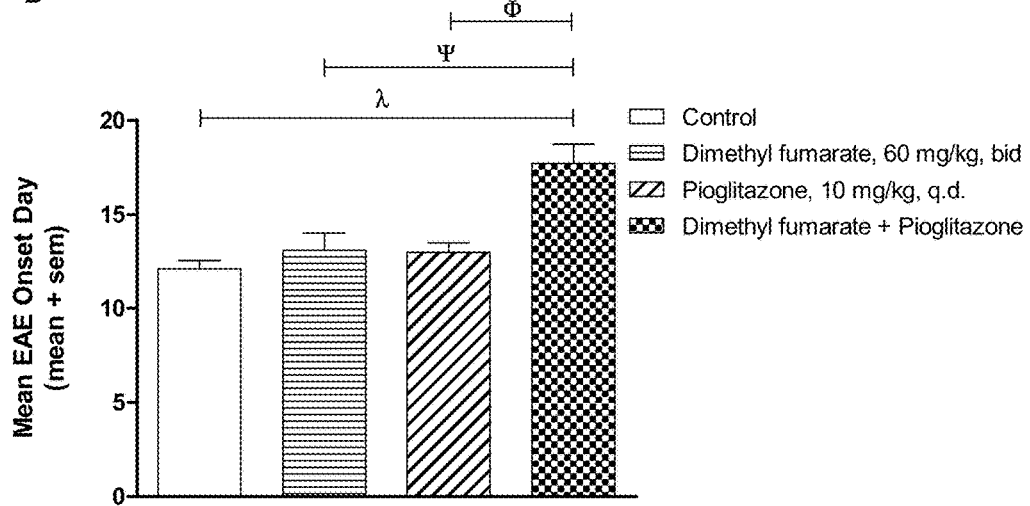
Figure 3A:
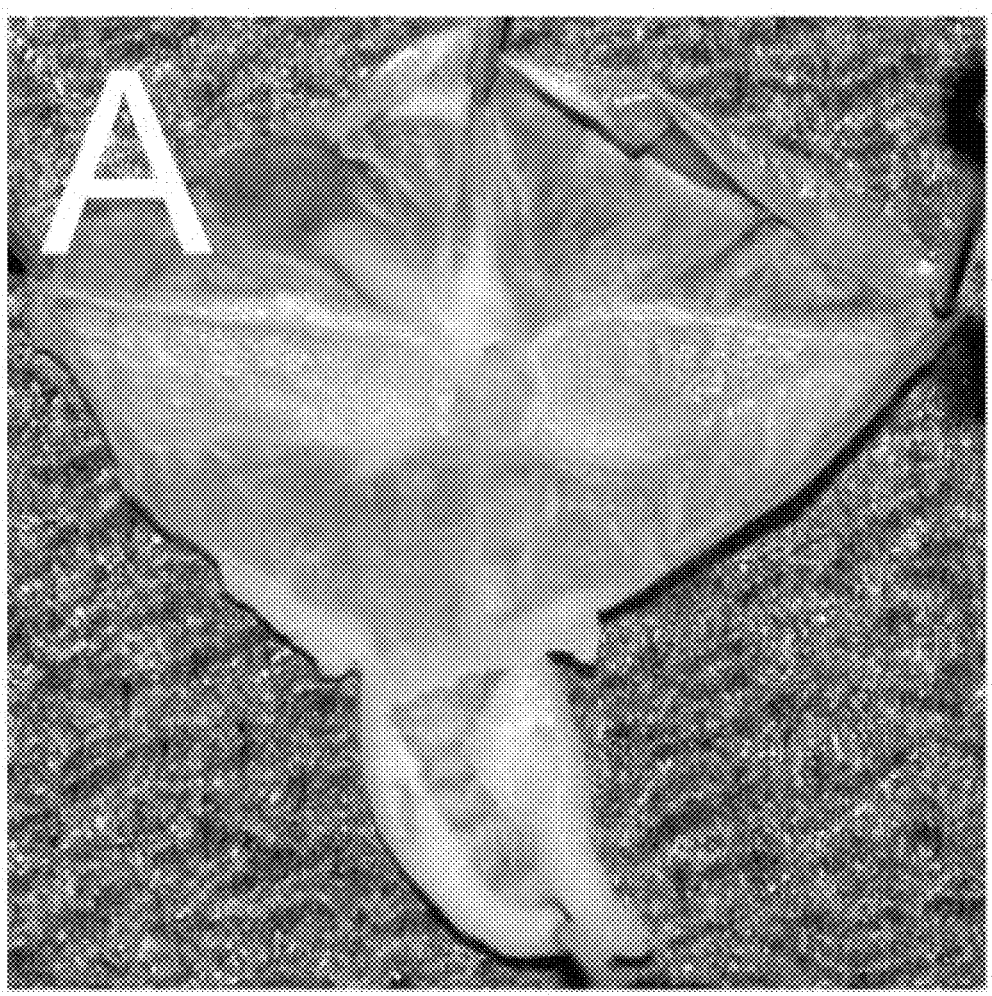
FIG. 3: Alteration in the macroscopical appearance of the stomachs of mice chronically treated with dimethyl fumarate, but not with pioglitazone or vehicle. Forty C57BL/6 mice immunized with MOG35-55 and treated by oral gavage for 22 days with a combination of HPMC0.5%/Tween20 0.25% b.i.d. plus Kleptose 20% q.d. (A, FIG. 3A), dimethyl fumarate 60 mg/kg b.i.d. plus Kleptose 20% q.d. (B), pioglitazone 10 mg/kg q.d. plus HPMC 0.5%/Tween20 0.25% b.i.d. (C, FIG. 3C) or dimethyl fumarate 60 mg/kg b.i.d. plus pioglitazone 10 mg/kg q.d. (D, FIG. 3D). An additional group of five mice were sham-immunized (emulsion without MOG35-55) and treated with HPMC0.5%/Tween20 0.25% b.i.d. plus Kleptose 20% q.d. (E, FIG. 3E). Throughout the length of the experiment three mice were either sacrificed due to humane end-points or succumbed to disease. The forty-two remaining animals were euthanized under pentobarbital terminal anesthesia, the right atrium of the heart was incised and mice were perfused with 4% paraformaldehyde through the left ventricle. The stomach of each mouse was dissected by a transection of the proximal segment of the esophagus and the duodenum then cut open via a longitudinal incision through the longest possible axis linking the remaining stretch of duodenum and the fundus. Each piece was washed with phosphate buffered saline and open-mounted. The images shown are from one representative mouse from each group. Note the normal appearance of stomachs of all groups of mice that were not exposed to dimethyl fumarate (A, C, E, FIGS. 3A, 3C, 3E, respectively) and the seemingly pathological increase in macrovilosity of the stomachs of groups B and D that were treated with dimethyl fumarate as stand-alone or combination treatment with pioglitazone, respectively, giving them a thickened and rugose appearance (FIGS. 3B and 3D, respectively).
Figure 3B:
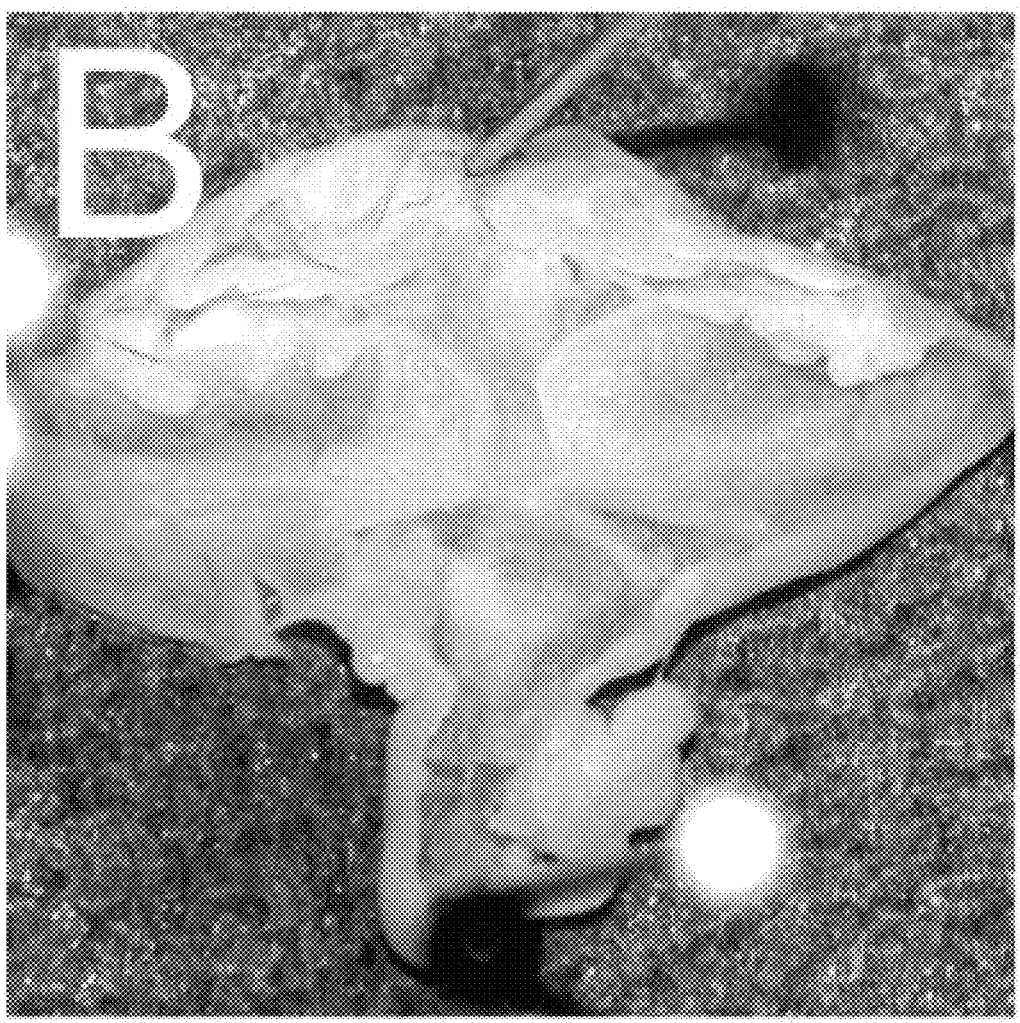
Figure 3C:
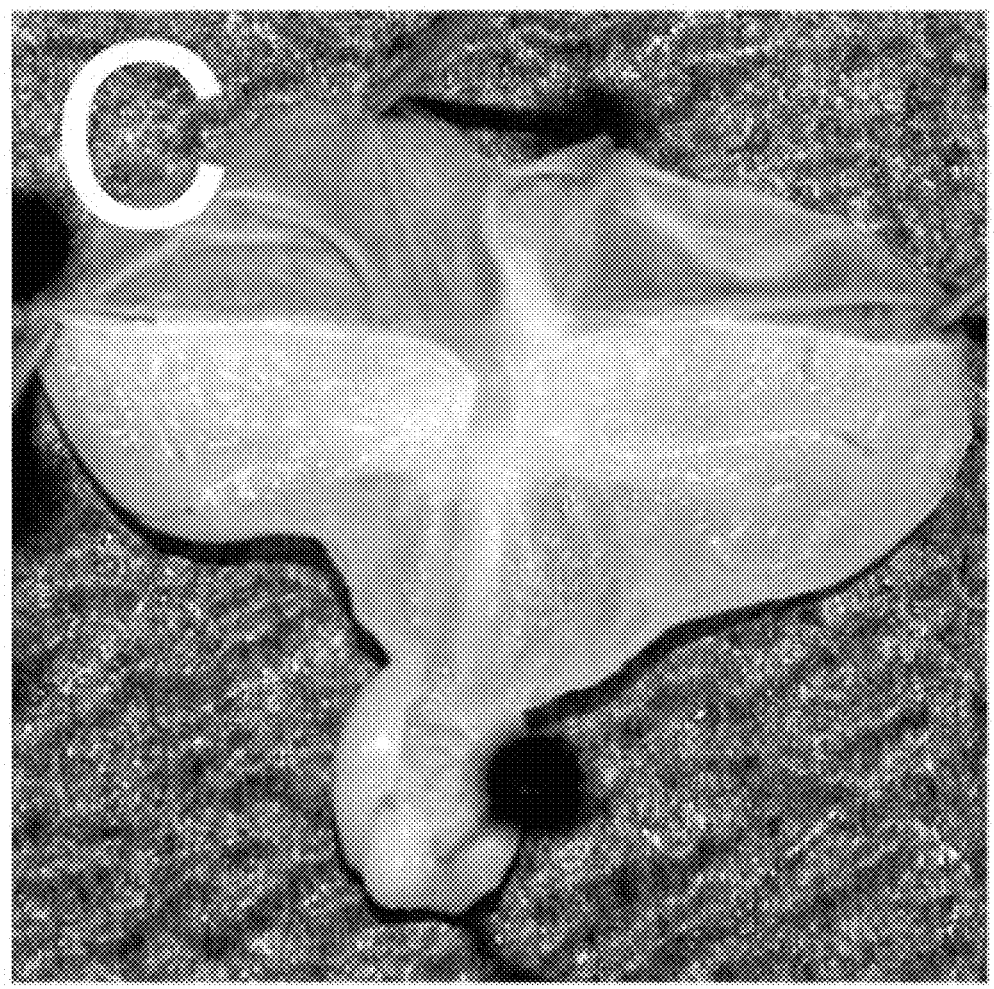
Figure 3D:
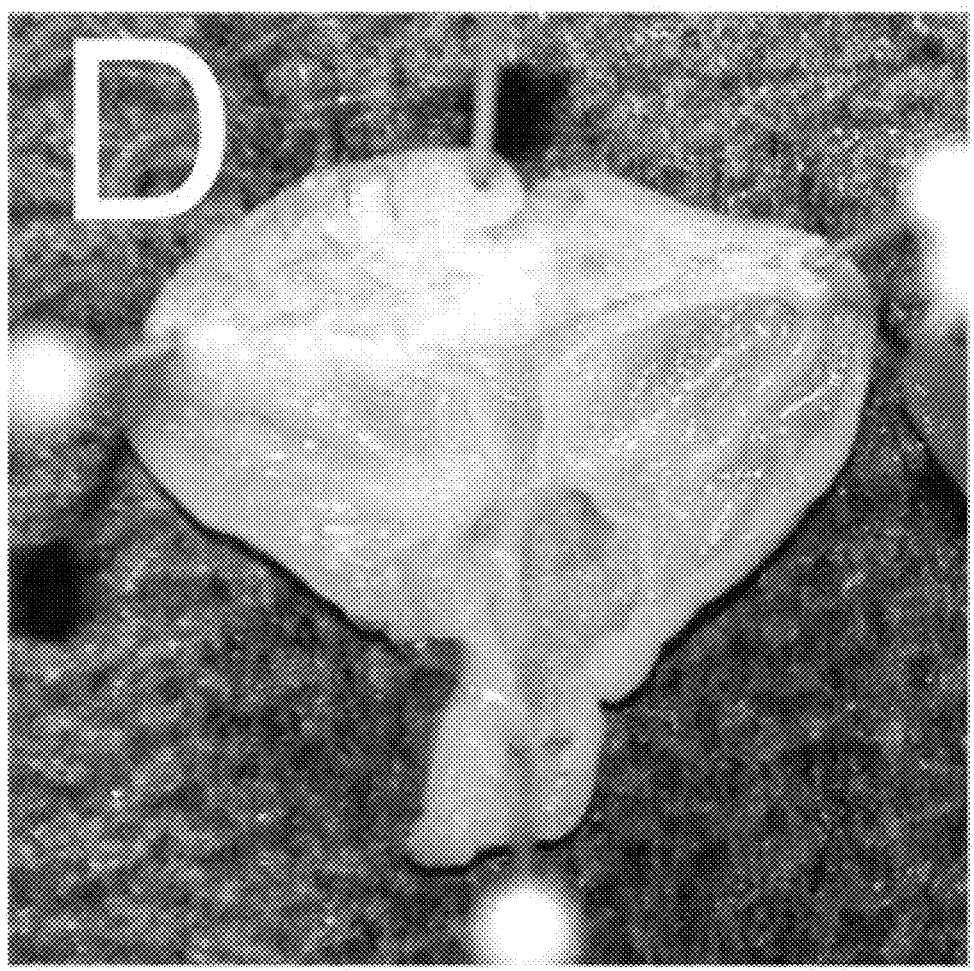
Figure 3E:
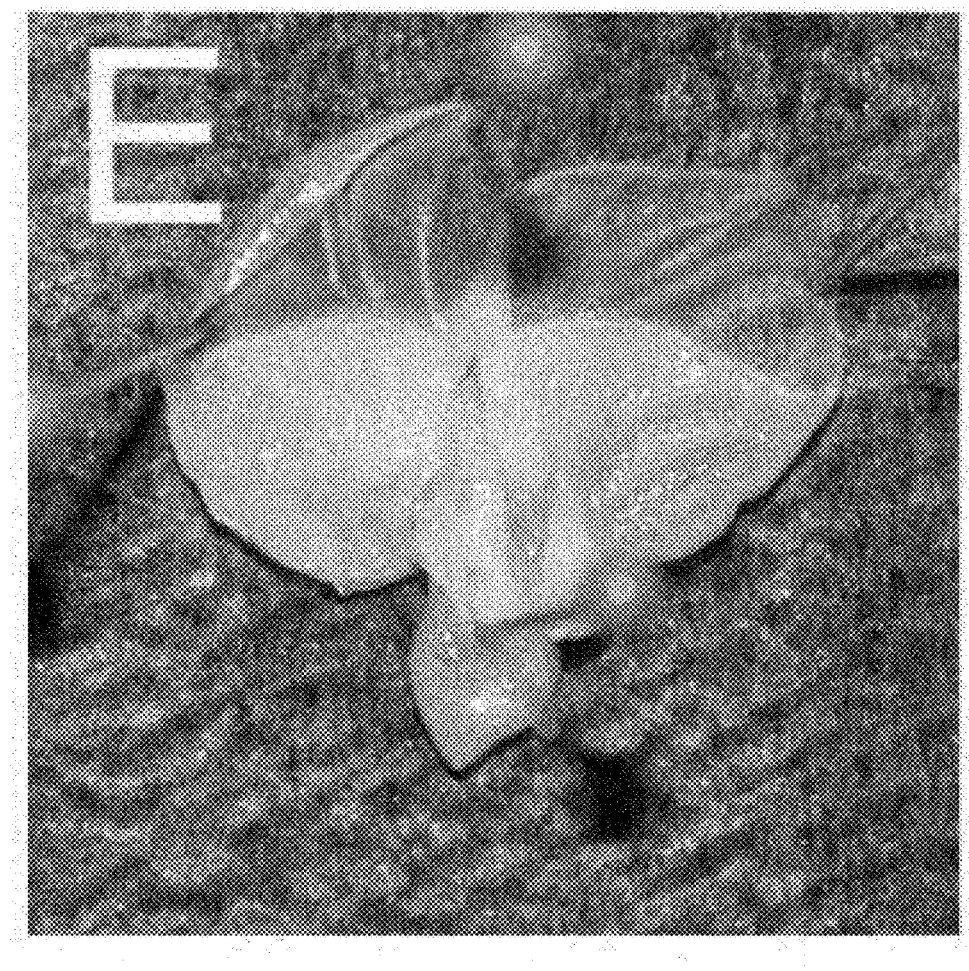

I claim:

1. A method of alleviating multiple sclerosis or a clinical symptom thereof or delaying the onset of multiple sclerosis or a clinical symptom thereof in a patient, comprising the co-administration of therapeutically effective amounts of an Nrf2 activator selected from the fumaric acid esters and salts thereof and a PPAR gamma agonist selected from glitazones and salt forms thereof to said patient.

2. The method according to claim 1, wherein the glitazone is selected from the group of pioglitazone and its salt forms and rosiglitazone and its salt forms.

3. The method according to claim 1, wherein the glitazone is pioglitazone.

4. The method according to claim 1, wherein the glitazone is pioglitazone hydrochloride.

5. The method according to claim 1, wherein the Nrf2 activator is selected from the group of monoalkyl fumarates and dialkyl fumarates.

6. The method according to claim 1, wherein the Nrf2 activator is selected from the group of monomethyl fumarate, dimethyl fumarate, monoethyl fumarate and diethyl fumarate.

7. The method according to claim 1, wherein the PPAR gamma agonist is rosiglitazone.

8. The method according to claim 1, wherein the PPAR gamma agonist is rosiglitazone maleate.

9. The method according to claim 1, wherein said co-administration is an oral administration.

* * * * *

UNITED STATES PATENT AND TRADEMARK OFFICE
CERTIFICATE OF CORRECTION

PATENT NO. : 10,426,763 B2
APPLICATION NO. : 15/356766
DATED : October 1, 2019
INVENTOR(S) : Bjoern Colin Kahrs Page 1 of 1

It is certified that error appears in the above-identified patent and that said Letters Patent is hereby corrected as shown below:

In the Specification

Column 1,
Line 32, "while PPAR is" should read --while PPARδ is--.

Column 2,
Line 60, "Prothymosin a," should read --Prothymosin α,--.

Column 4,
Line 19, "Nilsson andller," should read --Nilsson and Müller,--.

Column 15,
Line 9, "zerumb one," should read --zerumbone,--.
Line 18, "3-naphthoflavone," should read --β-naphthoflavone,--.
Line 29, "MCES," should read --MCE5,--.

Column 16,
Line 24, "[(±)-(4b 5,8aR,10aS)-10a-ethynyl-4b," should read
--[(±)-(4bS,8aR,10aS)-10a-ethynyl-4b,--.

Column 63,
Line 53, "containing 200 of" should read --containing 200 μg of--.

Column 65,
Line 55, "Ψ combination" should read --Ψ combination--.

Signed and Sealed this
Sixteenth Day of June, 2020

Andrei Iancu
*Director of the United States Patent and Trademark Office*